US008609111B2

(12) United States Patent
Ambrosino et al.

(10) Patent No.: US 8,609,111 B2
(45) Date of Patent: Dec. 17, 2013

(54) ANTIBODIES AGAINST CLOSTRIDIUM DIFFICILE TOXINS AND USES THEREOF

(75) Inventors: Donna M. Ambrosino, Jamaica Plain, MA (US); Gregory J. Babcock, Marlborough, MA (US); Teresa Broering, Brookline, MA (US); Robert Graziano, Frenchtown, NJ (US); Hector Javier Hernandez, Canton, MA (US); Israel Lowy, Dobbs Ferry, NY (US); Robert Mandell, Collins, IA (US); Deborah Molrine, Newton, MA (US); William D. Thomas, Jr., Dedham, MA (US); Hui-Fen Zhang, Bridgewater, NJ (US)

(73) Assignees: University of Massachusetts, Boston, MA (US); Medarex, L.L.C., Princeton, NJ (US)

( * ) Notice: Subject to any disclaimer, the term of this patent is extended or adjusted under 35 U.S.C. 154(b) by 0 days.

(21) Appl. No.: 13/490,757

(22) Filed: Jun. 7, 2012

(65) Prior Publication Data

US 2012/0288508 A1   Nov. 15, 2012

Related U.S. Application Data

(60) Continuation of application No. 12/533,501, filed on Jul. 31, 2009, now Pat. No. 8,236,311, which is a division of application No. 11/051,453, filed on Feb. 4, 2005, now Pat. No. 7,625,559.

(60) Provisional application No. 60/542,357, filed on Feb. 6, 2004, provisional application No. 60/613,854, filed on Sep. 28, 2004.

(51) Int. Cl.
| *A61K 39/08* | (2006.01) |
| *A61K 39/00* | (2006.01) |
| *A61K 39/395* | (2006.01) |
| *A61K 39/02* | (2006.01) |
| *A61K 39/38* | (2006.01) |
| *A61B 5/055* | (2006.01) |
| *C07H 21/02* | (2006.01) |

(52) U.S. Cl.
USPC ............... 424/239.1; 424/184.1; 424/139.1; 424/141.1; 424/130.1; 424/9.34; 424/234.1; 424/178.1; 424/236.1; 424/247.1; 536/23.1

(58) Field of Classification Search
None
See application file for complete search history.

(56) References Cited

U.S. PATENT DOCUMENTS

| 4,879,218 A | 11/1989 | Wilkins et al. |
| 5,231,003 A | 7/1993 | Coughlin et al. |
| 5,545,806 A | 8/1996 | Lonberg et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,814,477 A | 9/1998 | Williams et al. |
| 6,214,341 B1 | 4/2001 | Thomas, Jr. et al. |
| 6,573,003 B2 | 6/2003 | Williams et al. |
| 6,667,035 B1 | 12/2003 | Von Eichel-Streiber et al. |
| 6,733,760 B1 | 5/2004 | Wilkins et al. |
| 7,151,159 B2 | 12/2006 | Von Eichel-Streiber et al. |
| 7,625,559 B2 | 12/2009 | Ambrosino et al. |

FOREIGN PATENT DOCUMENTS

| AU | 746859 B2 | 3/1999 |
| WO | 92/03918 A1 | 3/1992 |
| WO | 93/12232 A1 | 6/1993 |
| WO | 94/13264 A1 | 6/1994 |
| WO | 94/24155 A1 | 10/1994 |
| WO | 94/25585 A1 | 11/1994 |
| WO | 96/12802 A1 | 5/1996 |
| WO | 98/24884 A1 | 6/1998 |
| WO | 99/12971 A2 | 3/1999 |
| WO | 99/20304 A1 | 4/1999 |
| WO | 01/53353 A2 | 7/2001 |
| WO | 01/92340 A2 | 12/2001 |
| WO | 03/079750 A2 | 10/2003 |
| WO | 03/092630 A2 | 11/2003 |

OTHER PUBLICATIONS

Aboud, Worood et al., "Pseudomembranous colitis," Gastrointest Endosc., vol. 52(2):234 (2000).
Adler, S. et al., "Costs of low-temperature plasma sterilization compared with other sterilization methods," Journal of Hospital Infection, vol. 40(2):125-134 (1998).
Aktories, K. et al., "Rho GTPases as targets of bacterial protein toxins," Biol. Chem., vol. 381(5-6):421-426 (2000).
Aldeen, William E. et al., "Comparison of the TOX A/B test to a cell culture cytotoxicity assay for the detection of *Clostridium difficile* in stools," Diagnosis Microbiology and Infectious Disease, vol. 36(4):211-213 (2000).
Alfa, Michelle J. et al., "Characterization of a toxin A-negative, toxin B-positive strain of *Clostridium difficile* responsible for a nosocomial outbreak of *Clostridium difficile*-associated diarrhea," Journal of Clinical Microbiology, vol. 38(7):2706-2714 (2000).
Anderson, Robert J. et al., "Evidence for Rho protein regulation of renal tubular epithelial cell function," Kidney International, vol. 58(5):1996-2006 (2000).
Aronsson, B. et al., "Diagnosis and epidemiology of *Clostridium difficile* enterocolitis in Sweden," Journal of Antimicrobial Chemotherapy vol. 14(Suppl D):85-95 (1984).
Aronsson, Bo et al., "Enzyme-linked immunosorbent assay (ELISA) for antibodies to *Clostridium difficile* toxins in patients with pseudomembranous colitis and antibiotic-associated diarrhoea," Journal of Immunological Methods, vol. 60(3):341-350 (1983).

(Continued)

Primary Examiner — Vanessa L Ford
Assistant Examiner — Lakia Tongue
(74) Attorney, Agent, or Firm — Nelson Mullins Riley & Scarborough LLP; Jane E. Remillard, Esq.; Jill Gorny Sloper, Esq.

(57) ABSTRACT

Antibodies that specifically bind to toxins of *C. difficile*, antigen binding portions thereof, and methods of making and using the antibodies and antigen binding portions thereof are provided herein.

30 Claims, 35 Drawing Sheets

(56) References Cited

OTHER PUBLICATIONS

Bacon, Alfred E. III et al., "Immunoglobulin G directed against toxins A and B of *Clostridium difficile* the general population and patients with antibiotic-associated diarrhea," Diagn. Microbiol. Infect. Dis., vol. 18(4):205-209 (1994).
Barbut, Frederic et al., "Antimicrobial susceptibilies and serogroups of clinical strains of *Clostridium difficile* isolated in France in 1991 and 1997," Antimicrobial Agents and Chemotherapy, vol. 43(11):2607-2611 (1999).
Barroso, Lisa A. et al., "Mutagenesis of the *Clostridium difficile* toxin B gene and effect of cytotoxic activity," Microbial Pathogenesis, vol. 16:297-303 (1994).
Barroso, L.A. et al., "Nucleotide sequence of *Clostridium difficile* toxin B gene," Nucleic Acids Research, vol. 18 (13):4004 (1990).
Barth, Holger et al., "Low pH-induced formation of ion channels by *Clostridium difficile* toxin B in target cells," The Journal of Biological Chemistry, vol. 276(14):10670-10676 (2001).
Bartlett, John G. et al., "Antibiotic-associated *Pseudomembranous colitis* due to toxin-producing clostridia," N. Engl. J. Med., vol. 298(10):531-534 (1978).
Bartlett, John G. et al. "Antibiotic-induced lethal enterocolitis in hamsters: studies with eleven agents and evidence to support the pathogenic role of toxin-producing Clostridia," Am. J. Vet. Res., vol. 39(9):1525-1530 (1978).
Bartlett, John G. et al., "Colitis induced by *Clostridium difficile*," Reviews of Infectious Diseases, vol. 1(2):370-378 (1979).
Bartlett, John G. et al., "Comparison of five regimens for treatment of experimental clindamycin-associated colitis," The Journal of Infectious Diseases, vol. 138(1):81-86 (1978).
Bartlett, John G, "Treatment of antibiotic-associated *Pseudomembranous colitis*," Reviews of Infectious Diseases, vol. 6(Suppl 1):S235-S241 (1984).
Berdoz, Jose et al., "In vitro comparison of the antigen-binding and stability properties of the various molecular forms of IgA antibodies assembled and produced in CHO cells," Proc. Natl. Acad. Sci. USA. vol. 96(6):3029-3034 (1999).
Berneman, Armand et al., "The specificity patterns of human immunoglobulin G antibodies in serum differ from those in autologous secretions," Infection and Immunity, vol. 66(9):4163-4168 (1998).
Bongaerts, Ger P.A. et al., "Role of toxins A and B in the pathogenesis of *Clostridium difficile* disease," Microbial Pathogenesis, vol. 17(1):1-12 (1994).
Boquet, Patrice, "Bacterial toxins inhibiting or activating small GTP-binding proteins," Ann. N.Y. Acad. Sci., vol. 886:83-90 (1999).
Borody, T.J., "'Flora Power'—fecal bacteria cure chronic C. difficile diarrhea," Am. J. Gastroenterol., vol. 95 (11):3028-3029 (2000).
Borriello, S.P. et al., "*Clostridium difficile*—a spectrum of virulence and analysis of putative virulence determinants in the hamster model of antibiotic-associated colitis," J. Med. Microbiol., vol. 24(1):53-64 (1987).
Borriello, S.P. et al., "*Clostridium difficile* infections of the gut: the unanswered questions," Journal of Antimicrobial Chemotherapy, vol. 41(Suppl C):67-69 (1998).
Borriello, S.P., "Pathogenesis of *Clostridium difficile* infection," Journal of Antimicrobial Chemotherapy, vol. 41 (Supp) C):13-19 (1998).
Bowie, James U. et al., "Deciphering the Message in Protein Sequences: Tolerance to Amino Acid Substitutions," Science, vol. 247:1306-1310 (1990).
Busch, Christian et al., "Involvement of a conserved tryptophan residue in the UDP-glucose binding of large clostridial cytotoxin glycosyltransferases," The Journal of Biological Chemistry, vol. 275(18): 13228-13234 (2000).
Calderon, Gloria M. et al., "Effects of toxin A from *Clostridium difficile* on mast cell activation and survival," Infection and Immunity, vol. 66(6):2755-2761 (1998).
Castagliuolo, Ignazio et al., "A receptor decoy inhibits the enterotoxic effects of *Clostridium difficile* toxin A in rat ileum," Gastroenterology, vol. 111(2):433-438 (1996).
Castagliuolo, Ignazio et al., "*Clostridium difficile* toxin a stimulates macrophage-inflammatory protein-2 production in intestinal rat ntestinal epithelial cells," The Journal of Immunology, vol. 160(12): 6039-6045 (1998).
Castagliuolo, Ignazio et al., "IL-11 inhibits *Clostridium difficile* toxin A enterotoxicity in rat ileum," Am. J. Physiol., vol. 273(2 Pt 1):G333-G341 (1997).
Castagliuolo, Ignazio et al., "*Saccharomyces boulardii* protease inhibits the effects of *Clostridium difficile* toxins A and B in human colonic mucosa," Infection and Immunity, vol. 67(1):302-307 (1999).
Cerquetti, Marina et al., "Characterization of surface layer proteins from different *Clostridium difficile* clinical isolates," Microbial Pathogenesis, vol. 28(6):363-372 (2000).
Chang, Te-Wen et al., "Clindamycin-induced enterocolitis in hamsters as a model of *Pseudomembranous colitis* in patients," Infection and Immunity, vol. 20(2):526-529 (1978).
Chang, Te-Wen et al., "Cytotoxicity assay in antibiotic-associated colitis," The Journal of Infectious Diseases, vol. 140(5):765-770 (1979).
Chang, Te-Wen et al., "Neutralization of Clostridium difficile toxin by *Clostridium sordellii* antitoxins," Infection and Immunity, vol. 22(2):418-422 (1978).
Chaves-Olarte, Esteban et al., "A novel cytotoxin from *Clostridium difficile* serogroup F is a functional hybrid between two other large clostridial cytotoxins," The Journal of Biological Chemistry, vol. 274(16): 11046-11052 (1999).
Chaves-Olarte, Esteban et al., "Toxins A and B from *Clostridium difficile* differ with respect to enzymatic potencies, cellular substrate specificities, and surface binding to cultured cells," J. Clin. Invest, vol. 100(7):1734-1741 (1997).
Ciesla, William P. Jr. et al., "*Clostridium difficile* toxins A and B are cation-dependent UDP-glucose hydrolases with differing catalytic activities," The Journal of Biological Chemistry, vol. 273(26):16021-16026 (1998).
Clabots, Connie R. et al., "Acquisition of *Clostridium difficile* by hospitalized patients: evidence for colonized new admissions as a source of infection," The Journal of Infectious Diseases, vol. 166(3):561-567 (1992).
Cohen, Stuart H. et al., "Analysis of the pathogenicity locus in *Clostridium difficile* strains," The Journal of Infectious Diseases, vol. 181(2):659-663 (2000).
Cohen, Stuart H. et al. "Isolation of a toxin B-deficient mutant strain of *Clostridium difficile* in a case of recurrent *C. difficile*-associated diarrhea," Clinical Infectious Diseases, vol. 26(2):410-412 (1998).
Cooke, Deborsah L. et al., "Nonspecific binding of *Clostridium difficile* toxin A to murine immunoglobulins occurs via the fab component," Infection and Immunity, vol., 66(5):1981-1984 (1988).
Corthier, G. et al., "Protection against experimental *Pseudomembranous colitis* in gnotobiotic mice by use of monoclonal antibodies against *Clostridium difficile* toxin A," Infect. Immun., vol. 59(3):1192-1195 (1991).
Czuprynski, Charles J. et al., "*Pseudomembranous colitis* in *Clostridium difficile*-monoassociated rats," Infection and Immunity, vol. 39(3):1368-1376 (1983).
Dallas, S.D. et al., "Binding of *Clostridium difficile* toxin A to human milk secretory component," J. Med. Microbiol., vol. 47(10):879-888 (1998).
De Girolami, P.C. et al., "Multicenter evaluation of a new enzyme immunoassay for detection of *Clostridium difficile* enterotoxin A," J. Clin. Microbiol., vol. 30(5):1085-1088 (1992).
De Lalla, F. et al., "Third generation cephalosporins as a risk factor for *Clostridium difficile*-associated disease: a four-year survey in a general hospital," J. Antimicrob. Chemother., vol. 23(4):623-631 (1989).
Deng, Xiao K. et al., "Recombinant Single-Chain Variable Fragment Antibodies Directed against *Clostridium difficle* Toxin B Produced by Use of an Optimized Phage Display System," Clinical and Diagnostic Laboratory Immunology, vol. 10(4):587-595 (2003).
Korhonen, Hannu et al., "Bovine milk antibodies for health," Br. J. Nutr., vol. 84(Suppl. 1):S135-S146 (2000).

(56) References Cited

OTHER PUBLICATIONS

Kotloff, Karen L. et al., "Safety and immunogenicity of increasing doses of a *Clostridium difficile* toxoid vaccine administered to healthy adults," Infect. Immun., vol. 69(2):988-995 (2001).
Krah, David L., "Assays for antibodies to varicella-zoster virus," Infect. Dis. Clin. North Am., vol. 10(3):507-527 (1996).
Kroker, P.B. et al., "Clostridium difficile infection, hospital geography and time-space clustering," QJM, vol. 94 (4):223-225 (2001).
Kurtz, Caroline B. et al., "GT160-246, a toxin binding polymer for treatment of *Clostridium difficile* colitis," Antimicrob. Agents Chemother., vol. 45(8):2340-2347 (2001).
Lamm, Michael E., "Interaction of antigens and antibodies at mucosal surfaces," Annu. Rev. Microbiol., vol. 51:311-340 (1997).
Landry, Marie L. et al., "Comparison of fluorescent-antibody-to-membrane-antigen test, indirect immunofluorescence assay, and a commercial enzyme-linked immunosorbent assay for determination of antibody to varicella-zoster virus," J. Clin. Microbiol., vol. 25(5):832-835 (1987).
Leung, Donald Y.M. et al., "Treatment with intravenously administered gamma globulin of chronic relapsing colitis induced by *Clostridium difficile* toxin," J. Pediatr, vol. 118:633-637 (1991).
Libby, Jeffrey M. et al., "Effects of the two toxins of *Clostridium difficile* in antibiotic-associated cecitis in hamsters," Infect. Immun., vol. 36(2):822-829 (1982).
Limaye, Ajit P. et al., "*Pseudomembranous colitis* caused by a toxin A(-) B(+) strain of *Clostridium difficile*," J. Clin. Microbiol., vol. 38(4):1696-1697 (2000).
Lyerly, David M. et al., "Effects of *Clostridium difficile* toxins given intragastrically to animals," Infect. Immun., vol. 47 (2):349-352 (1985).
Lyerly, David M. et al., "Monoclonal and specific polyclonal antibodies for immunoassay of *Clostridium difficile* toxin A," J. Clin. Microbiol., vol. 21(1):12-14 (1985).
Lyerly, David M. et al., "Passive immunization of hamsters against disease caused by *Clostridium difficile* by use of bovine immunoglobulin G concentrate," Infect. Immun., vol. 59(6):2215-2218 (1991).
Madan, Elio et al., "Stool caproic acid for screening of *Clostridium difficile*," Am. J. Clin. Pathol., vol. 89(4):525-527 (1988).
Mahida, Y.R. et al., "Effect of *Clostridium difficile* toxin A on human colonic lamina propria cells: early loss of macrophages followed by T-cell apoptosis," Infect. Immun., vol. 66(11):5462-5469 (1998).
Mahida, Y.R. et al., "Effect of *Clostridium difficile* toxin A on human intestinal epithelial cells: induction of interleukin 8 production and apoptosis after cell detachment," Gut, vol. 38(3):337-347 (1996).
Mahida, Y.R. et al., "Migration of human intestinal lamina propria lymphocytes, macrophages and eosinophils following the loss of surface epithelial cells," Clin. Exp. Immunol., vol. 109(2):377-386 (1997).
Mani, Nagraj et al., "Regulation of toxin synthesis in *Clostridium difficile* by an alternative RNA polymerase sigma factor," Proc. Natl. Acad. Sci. USA, vol. 98(10):5844-5849 (2001).
Massol, Philippe et al., "Fc receptor-mediated phagocytosis requires CDC42 and Rac1," EMBO J., vol. 17 (21):6219-6229 (1998).
Mattsson, Jens G. et al., "MPS1: a small, evolutionarily conserved zinc finger protein from the protozoan *Toxoplasma gondii*," FEMS Microbiol. Lett., vol. 180(2):235-239 (1999).
Mayfield, Jennie L. et al., "Environmental control to reduce transmission of *Clostridium difficile*," Clin. Infect. Dis., vol. 31(4):995-1000 (2000).
McFarland, Lynne V. et al., "Correlation of immunoblot type, enterotoxin production, and cytotoxin production with clinical manifestations of *Clostridium difficile* infection in a cohort of hospitalized patients," Infect. Immun., vol. 59 (7):2456-2462 (1991).
McFarland, Lynne V. et al., "Nosocomial acquisition of *Clostridium difficile* infection," N. Engl. J. Med., vol. 320 (4):204-210 (1989).
McFarland, Lynne V. et al., "Risk factors for *Clostridium difficile* carriage and *C. difficile*-associated diarrhea in a cohort of hospitalized patients," J. Infect. Dis., vol. 162(3):678-684 (1990).
McGhee, Jerry R. et al., "The mucosal immune system: from fundamental concepts to vaccine development," Vaccine, vol. 10(2):75-88 (1992).
Miller, P. David et al., "Macrophage-dependent stimulation of T cell-depleted spleen cells by *Clostridium difficile* toxin A and calcium ionophore," Cell. Immunol., vol. 126(1):155-163 (1990).
Moncrief, J. Scott et al., "Genetic characterization of toxin A-negative, toxin B-positive *Clostridium difficile* isolates by PCR," J. Clin. Microbiol., vol. 38(8):3072-3075 (2000).
Moncrief, J. Scott et al., "Genetics of *Clostridium difficile* toxins," Curr. Top. Microbiol. Immunol., vol. 250:35-54 (2000).
Moore, Ronda et al., "*C. difficile* toxin A increases intestinal permeability and induces Cl- secretion," Am. J. Physiol., vol. 259(2 Pt. 1):G165-G172 (1990).
Muller, Frank et al., "Monoclonal Antibodies Specific for *Clostridium difficile* Toxin B and Their Use in Immunoassays," Journal of Clinical Microbiology, vol. 30(6):1544-1550 (1992).
Mulligan, Maury Ellis et al., "Elevated levels of serum immunoglobulins in asymptomatic carriers of *Clostridium difficile*," Clin. Infect. Dis., vol. 16(Suppl. 4):S239-S244 (1993).
Mylonakis, Eleftherios et al., "*Clostridium difficile*—Associated diarrhea: A review," Arch. Intern. Med., vol. 161 (4):525-533 (2001).
Nusrat, A. et al., "*Clostridium difficile* toxins disrupt epithelial barrier function by altering membrane microdomain localization of tight junction proteins," Infect. Immun., vol. 69(3):1329-1336 (2001).
Ohguchi, Kenji et al., "Effects of *Clostridium difficile* toxin A and toxin B on phospholipase D activation in human promyelocytic leukemic HL60 cells," Infect. Immun., vol. 64(11):4433-4437 (1996).
Pavliakova, Danka et al., "*Clostridium difficile* recombinant toxin A repeating units as a carrier protein for conjugate vaccines: studies of pneumococcal type 14, *Escherichia coli* K1, and *Shigella flexneri* type 2a polysaccharides in mice," Infect. Immun., vol. 68(4):2161-2166 (2000).
Peakman, Timothy C. et al., "Comparison of expression of a humanized monoclonal antibody in mouse NSO myeloma cells and Chinese hamster ovary cells," Hum. Antibodies Hybridomas, vol. 5(1-2):65-74 (1994).
Pochapin, Mark, "The effect of probiotics on *Clostridium difficile* diarrhea," Am. J. Gastroenterol, vol. 95(1 Suppl.): S11-S13 (2000).
Pothoulakis, C. et al., "*Clostridium difficile* cytotoxin inhibits protein synthesis in fibroblasts and intestinal mucosa," Gastroenterology, vol. 91(5):1147-1153 (1986).
Pothoulakis, Charalabos et al., "*Clostridium difficile* toxin A stimulates intracellular calcium release and chemotactic response in human granulocytes," J. Clin. Invest, vol. 81(6):1741-1745 (1988).
Pothoulakis, Charalabos, "Effects of *Clostridium difficile* toxins on epithelial cell barrier," Ann. N.Y. Acad. Sci., vol. 915:347-356 (2000).
Pothoulakis, Charalabos et al., "Microbes and microbial toxins: paradigms for microbial-mucosal interactions II. The integrated response of the intestine to *Clostridium difficile* toxins," Am. J. Physiol. Gastrointest. Liver Physiol., vol. 280(2):G178-G183 (2001).
Pothoulakis, Charalabos et al., "Purification and properties of *Clostridium difficile* cytotoxin B," J. Biol. Chem., vol. 261(3):1316-1321 (1986).
Qa'Dan, Maen et al., "pH-induced conformational changes in *Clostridium difficile* toxin B," Infect. Immun., vol. 68 (5):2470-2474 (2000).
Qamar, Amir et al., "*Saccharomyces boulardii* stimulates intestinal immunoglobulin a immune response to *Clostridium difficile* toxin A in mice," Infect. Immun., vol. 69(4):2762-2765 (2001).
Reeve, Reeve, "Two statistical methods for estimating relative potency of bioassays," BioPharm, vol. 13(7)54-60 (2000).
Riegler, Martin et al., "*Clostridium difficile* toxin B is more potent than toxin a in damaging human colonic epithelium in vitro," J. Clin. Invest., vol. 95(5):2004-2011 (1995).
Rolland, Rosalind M. et al., "Five spontaneous deaths associated with *Clostridium difficile* in a colony of cotton-top tamarins (*Saguinus oedipus*)," Lab. Anim. Sci., vol. 47(5):472-476 (1997).
Rupnik, Maja et al., "Comparison of toxinotyping and PCR ribotyping of *Clostridium difficile* strains and description of novel toxinotypes," Microbiology, vol. 147(Pt. 2):439-447 (2001).

(56) References Cited

OTHER PUBLICATIONS

Ryan, Eeward T. et al., "Protective immunity against *Clostridium difficile* toxin A induced by oral immunization with a live, attenuated *Vibrio cholerae* vector strain," Infect. Immun., vol. 65(7):2941-2949 (1997).
Salcedo, J. et al., "Intravenous immunoglobulin therapy for severe *Clostridium difficile* colitis," Gut, vol. 41 (3):366-370 (1997).
Sambol, Susan P. et al., "Infection of hamsters with epidemiologically important strains of *Clostridium difficile*," J. Infect. Dis., vol. 183(12):1760-1766 (2001).
Sambol, Susan P. et al., "Toxin gene analysis of a variant strain of *Clostridium difficile* that causes human clinical disease," Infect. Immun., vol. 68(10):5480-5487 (2000).
Samore, M.H., "Epidemiology of nosocomial clostridium difficile diarrhoea," J. Hosp. Infect., vol. 43(Suppl.):S183-S190 (1999).
Sauerborn, Markus, "The C-terminal ligand-binding domain of *Clostridium difficile* toxin A (TcdA) abrogates TcdA-specific binding to cells and prevents mouse lethality," FEMS Microbiol. Lett., vol. 155(1):45-54 (1997).
Saville, William J. et al., "Necrotizing enterocolitis in horses: a retrospective study," J. Vet. Intern. Med., vol. 10 (4):265-270 (1996).
Seffernick, Jennifer L. et al., "Melamine Deaminase and Atrazine Chlorohydrolase: 98 Percent Identical but Functionally Different," Journal of Bacteriology, vol. 183(8):2405-2410 (2001).
Siffert, Jean-Claude et al., "Effects of *Clostridium difficile* toxin B on human monocytes and macrophages: possible relationship with cytoskeletal rearrangement," Infect. Immun., vol. 61(3):1082-1090 (1993).
Smith, J.A. et al., "*Clostridium difficile* toxin a binding to human intestinal epithelial cells," J. Med. Microbiol., vol. 46 (11):953-958 (1997).
Souza, M.H.L.P. et al., "The involvement of macrophage-derived tumour necrosis factor and lipoxygenase products on the neutrophil recruitment induced by *Clostridium difficile* toxin B," Immunology, vol. 91(2):281-288 (1997).
Spencer, Robert C., "Clinical impact and associated costs of *Clostridium difficile*-associated disease," J. Antimicrob. Chemother., vol. 41(Suppl. C):5-12 (1998).
Spyres, Lea M. et al., "Mutational Analysis of the Enzymatic Domain of *Clostridium difficile* Toxin B Reveals Novel Inhibitors of the Wild-Type Toxin," Infection and Immunity, vol. 71(6):3294-3301 (2003).
Stubbe, Hiltrud et al., "Polymeric IgA is superior to monomeric IgA and IgG carrying the same variable domain in preventing Clostridium difficile toxin a damaging of T84 monolayers," J. Immunol., vol. 164(4):1952-1960 (2000).
Surawicz, Christina M. et al., "The search for a better treatment for recurrent *Clostridium difficile* disease: use of high-dose vancomycin combined with *Saccharomyces boulardii*," Clin. Infect. Dis., vol. 31(4):1012-1017 (2000).
Teasley, David G. et al., "Prospective randomised trial of metronidazole versus vancomycin for Clostridium-difficileassociated diarrhoea and colitis," Lancet, vol. 2(8358):1043-1046 (1983).
Thelestam, M. et al., "Cytotoxic effects of the Clostridium difficile toxins," Curr. Top. Microbiol. Immunol., vol. 250:85-96 (2000).
Thelestam, M. et al., "Interaction of cytopathogenic toxin from Clostridium difficile with cells in tissue culture," Scand. J. Infect. Dis. Suppl., (Suppl. 22):16-29 (1980).
Thielman, Nathan M., "Antibiotic-associated colitis," Mandell, Douglas, and Bennett's Principles and Practice of Infectious Diseases, 5th Edition, Mandell, G. (Ed.), Churchill Livingstone, Philadelphia, Chapter 84, pp. 1111-1126 (2000).
Tjellstrom, B. et al., "Oral immunoglobulin a supplement in treatment of Clostridium difficile enteritis," Lancet, vol. 341(8846):701-702 (1993).
Toothaker, Roger D. et al., "Prevention of clindamycin-induced mortality in hamsters by Saccharomyces boulardii," Antimicrob. Agents Chemother., vol. 26(4):552-556 (1984).

Torres, J. F. et al., "Antigenicity of amino-acid sequences from Clostridium difficile toxin B," J. Med. Microbiol., vol. 44:464-474 (1996).
Torres, Javier F. et al., "Evaluation of formalin-inactivated *Clostridium difficile* vaccines administered by parenteral and mucosal routes of immunization in hamsters," Infect. Immun., vol. 63(12):4619-4627 (1995).
Triadafilopoulos, George et al., "Differential effects of Clostridium difficile toxins a and B on rabbit ileum," Gastroenterology, vol. 93(2):273-279 (1987).
Viscidi, R. et al., "Serum antibody response to toxins A and B of *Clostridium difficile*," J. Infect. Dis., vol. 148 (1):93-100 (1983).
Walev, Iwan et al., "Delivery of proteins into living cells by reversible membrane permeabilization with streptolysin-O," Proc. Natl. Acad. Sci. USA, vol. 98(6):3185-3190 (2001).
Waligora, Anne-Judith et al., "*Clostridium difficile* cell attachment is modified by environmental factors," Appl. Environ. Microbiol., vol. 65(9):4234-4238 (1999).
Ward, Stephen J. et al., "Local and systemic neutralizing antibody responses induced by intranasal immunization with the nontoxic binding domain of toxin A from *Clostridium difficile*," Infect. Immun., vol. 67(10):5124-5132 (1999).
Ward, Stephen J. et al., "Immunogenicity of a Salmonella typhimurium aroA aroD vaccine expressing a nontoxic domain of *Clostridium difficile* toxin A," Infect. Immun., vol. 67(5):2145-2152 (1999).
Warny, M. et al., "Bovine immunoglobulin concentrate-clostridium difficile retains C difficile toxin neutralising activity after passage through the human stomach and small intestine," Gut, vol. 44(2):212-217 (1999).
Warny, M. et al., "Gamma globulin administration in relapsing *Clostridium difficile*-induced *Pseudomembranous colitis* with a defective antibody response to toxin A," Acta Clin Belg., vol. 50(1):36-39 (1995).
Warny, Michel et al., "Human antibody response to *Clostridium difficile* toxin A in relation to clinical course of infection," Infect. Immum, vol. 62(2):384-389 (1994).
Wedel, Nancy et al., "Ultrastructural effects of *Clostridium difficile* toxin B on smooth muscle cells and fibroblasts," Exp. Cell Res., vol. 148(2):413-422 (1983).
Wilcox, M. et al., "Role of antibody response in outcome of antibiotic-associated diarrhoea," Lancet, vol. 357 (9251):158-159 (2001).
Wistrom, Johan et al., "Frequency of antibiotic-associated diarrhoea in 2462 antibiotic-treated hospitalized patients: a prospective study," J. Antimicrob. Chemother., vol. 47(1):43-50 (2001).
Xia, Y. et al., "*Clostridium difficile* toxin A excites enteric neurones and suppresses sympathetic neurotransmission in the guinea pig," Gut, vol. 46(4):481-486 (2000).
International Search Report for Application No. PCT/US2005/003725, 8 pages, dated Feb. 6, 2004.
Dipersio, J.R. et al., "Development of a rapid enzyme immunoassay for *Clostridium difficile* toxin a and its use in the diagnosis of *C. difficile*-associated disease," J. Clin. Microbiol., vol. 29(12):2724-2730 (1991).
Doern, Gary V. et al., "Laboratory diagnosis of *Clostridium difficile*-associated gastrointestinal disease: comparison of a monoclonal antibody enzyme immunoassay for toxins A and B with a monoclonal antibody enzyme immunoassay for toxin a only and two cytotoxicity assays," J. Clin. Microbiol., vol. 30(8):2042-2046 (1992).
Donta, Sam T. et al., "Effects of *Clostridium difficile* toxin on tissue-cultured cells," J. Infect. Dis., vol. 141(2):218-222 (1980).
El-Gammal, Ayman et al., "Evaluation of the clinical usefulness of *C. difficile* toxin testing in hospitalized patients with diarrhea," Diagn. Microbiol. Infect. Dis., vol. 36(3):169-173 (2000).
Enad, Deborah et al., "Is *Clostridium difficile* a pathogen in the newborn intensive care unit? a prospective evaluation," J. Perinatol., vol. 17(5):355-359 (1997).
Farrell, R.J. et al., "Pathogenesis and clinical manifestations of *Clostridium difficile* diarrhea and colitis," Curr. Top. Microbiol. Immunol., vol. 250:109-125 (2000).
Faust, Charles et al., "The enzymatic domain of *Clostridium difficile* toxin a is located within its N-terminal region," Biochem. Biophys. Res. Commun., vol. 251(1):100-105 (1998).

(56) References Cited

OTHER PUBLICATIONS

Fekety, Robert et al., "Treatment of antibiotic-associated *Clostridium difficile* colitis with oral vancomycin: comparison of two dosage regimens," Am. J. Med., vol. 86(1):15-19 (1989).
Feltis, Brad A. et al., "Clostridium difficile toxins A and B can alter epithelial permeability and promote bacterial paracellular migration through HT-29 enterocytes," Shock, vol. 14(6):629-634 (2000).
Feltis, Brad Allen et al., "*Clostridium difficile* toxins may augment bacterial penetration of intestinal epithelium," Arch. Surg., vol. 134(11):1235-1241 (1999).
Fernie, D.S. et al., "Active and passive immunization to protect against antibiotic associated caecitis in hamsters," Dev. Biol. Stand., vol. 53:325-332 (1983).
Fiorentini, Carla et al., "Clostridium difficile toxin B induces apoptosis in intestinal cultured cells," Infect. Immun., vol. 66(6):2660-2665 (1998).
Fishwild, Dianne M. et al., "High-avidity human IgG kappa monoclonal antibodies from a novel strain of minilocus transgenic mice," Nat. Biotechnol., vol. 14(7):845-851 (1996).
Frey, Steven M et al., "Localization of Two Epitopes Recognized by Monoclonal Antibody PCG-4 on *Clostridium difficile* Toxin A," Infection and Immunity, vol. 60(6):2488-2492 (1992).
Frost, F. et al., "Estimated incidence of *Clostridium difficile* infection," Emerg. Infect. Dis., vol. 5(2):303-304 (1999).
Genth, Harald et al., "Monoglucosylation of RhoA at threonine 37 blocks cytosol-membrane cycling," J. Biol. Chem., vol. 274(41):29050-29056 (1999).
Genth, Harald et al., "New method to generate enzymatically deficient Clostridium difficile toxin B as an antigen for immunization," Infect. Immun., vol. 68(3):1094-1101 (2000).
Gerding, Dale N. et al., "*Clostridium difficile*-associated diarrhea and colitis," Infect. Control Hosp. Epidemiol., vol. 16(8):459-477 (1995).
Gerding, D.N., "Treatment of *Clostridium difficile*-associated diarrhea and colitis," Curr. Top. Microbiol. Immunol., vol. 250:127-139 (2000).
Giannasca, Paul J. et al., "Serum antitoxin antibodies mediate systemic and mucosal protection from *Clostridium difficile* disease in hamsters," Infect. Immun., vol. 67(2):527-538 (1999).
Gilbert, Richard J. et al., "Effect of purified *Clostridium difficile* toxins on intestinal smooth muscle. I. Toxin A," Am. J. Physiol., vol. 256(4 Pt 1):G759-G766 (1989).
Gilbert, Richard J. et al., "Effect of purified *Clostridium difficile* toxins on intestinal smooth muscle. II. Toxin B," Am. J. Physiol., vol. 256(4 Pt 1):G767-G772 (1989).
Gorbach, S.L., "Antibiotics and Clostridium difficile," N. Engl. J. Med., vol. 341(22): 1690-1691 (1999).
Gotz, Vincent P. et al., "Medical management of antimicrobial-associated diarrhea and colitis," Pharmacotherapy, vol. 2(2):100-109 (1982).
Greenspan, Neil S. et al., "Defining epitopes: It's not as easy as it seems," Nature Biotechnology, vol. 17:936-937 (1999).
Guerrant, Richard L. et al., "How intestinal bacteria cause disease," J. Infect. Dis., vol. 179 (Suppl. 2):S331-S337 (1999).
He, D. et al., "*Clostridium difficile* toxin A causes early damage to mitochondria in cultured cells," Gastroenterology, vol. 119(1):139-150 (2000).
Hirschhorn, Lisa R. et al., "Epidemiology of community-acquired *Clostridium difficile*-associated diarrhea," J. Infect. Dis., vol. 169(1):127-133 (1994).

Hofmann, Fred et al., "*Chimeric clostridial* cytotoxins: identification of the N-terminal region involved in protein substrate recognition," Infect. Immun., vol. 66(3):1076-1081 (1998).
Hofmann, Fred et al., "Localization of the glucosyltransferase activity of *Clostridium difficile* toxin B to the N-terminal part of the holotoxin," J. Biol. Chem., vol. 272(17):11074-11078 (1997).
Johnson, Stuart et al., "*Clostridium difficile*—associated diarrhea," Clin. Infect. Dis., vol. 26(5):1027-1034 (1998).
Johnson, Stuart et al., "Epidemics of diarrhea caused by a clindamycin-resistant strain of *Clostridium difficile* in four hospitals," N. Engl. J. Med., vol. 341(22):1645-1651 (1999).
Johnson, Stuart et al., "Nosocomial *Clostridium difficile* colonisation and disease," Lancet, vol. 336(8707):97-100 (1990).
Johnson, Stuart et al., "Selective neutralization of a bacterial enterotoxin by serum immunoglobulin A in response to mucosal disease," Infect. Immun., vol. 63(8):3166-3173 (1995).
Johnson, Stuart et al., "Systemic and mucosal antibody responses to toxin A in patients infected with *Clostridium difficile*," J. Infect. Dis., vol. 166(6):1287-1294 (1992).
Johnson, Stuart et al., "Treatment of asymptomatic *Clostridium difficile* carriers (fecal excretors) with vancomycin or metronidazole. A randomized, placebo-controlled trial," Ann. Intern. Med., vol. 117(4):297-302 (1992).
Just, I. et al., "Glucosylation of Rho proteins by *Clostridium difficile* toxin B," Nature, vol. 375(6531):500-503 (1995).
Just, I. et al., "Large clostridial cytotoxins as tools in cell biology," Curr. Top. Microbiol. Immunol., vol. 250:97-107 (2000).
Just, I. et al., "Molecular mode of action of the large clostridial cytotoxins," Curr. Top. Microbiol. Immunol., vol. 250:55-83 (2000).
Karasawa, Tadahiro et al., "Laboratory diagnosis of toxigenic *Clostridium difficile* by polymerase chain reaction: presence of toxin genes and their stable expression in toxigenic isolates from Japanese individuals," J. Gastroenterol., vol. 34(1):41-45 (1999).
Karlsson, Sture et al., "Suppression of toxin production in *Clostridium difficile* VPI 10463 by amino acids," Microbiology, vol. 145( Pt. 7):1683-1693 (1999).
Kato, Haru et al., "Deletions in the repeating sequences of the toxin A gene of toxin A-negative, toxin B-positive *Clostridium difficile* strains," FEMS Microbiol. Lett., vol. 175(2):197-203 (1999).
Kawamoto, Satomi et al., "*Pseudomembranous colitis*: spectrum of imaging findings with clinical and pathologic correlation," Radiographics, vol. 19(4):887-897 (1999).
Kelley, Brian D. et al., "Demonstrating process robustness for chromatographic purification of a recombinant protein," BioPharm, vol. 10:36-47 (1997).
Kelly, Ciaran P. et al., "Clostridium difficile infection," Annu. Rev. Med., vol. 49:375-390 (1998).
Kelly, Ciaran P., "Immune response to *Clostridium difficile* infection," Eur. J. Gastroenterol. Hepatol., vol. 8 (11):1048-1053 (1996).
Kim, Pyeung-Hyeun et al., "Immunization of adult hamsters against *Clostridium difficile*-associated ileocecitis and transfer of protection to infant hamsters," Infect. Immun., vol. 55(12):2984-2992 (1987).
Kink, John A. et al., "Antibodies to recombinant *Clostridium difficile* toxins A and B are an effective treatment and prevent relapse of *C. difficile*-associated disease in a hamster model of infection," Infect. Immun., vol. 66(5):2018-2025 (1998).
Klingler, Paul J. et al., "*Clostridium difficile* infection: risk factors, medical and surgical management," Dig. Dis., vol. 18(3):147-160 (2000).
Knoop, Floyd C. et al., "*Clostridium difficile*: clinical disease and diagnosis," Clin. Microbiol. Rev., vol. 6(3):251-265 (1993).

FIG. 1

Amino Acid Sequences of Monoclonal Anti-Toxin A Antibodies Variable Light Chain Regions (L) and Variable Heavy Chain Regions (H)

| Clone | chain | | Amino Acid Sequence | SEQ ID NO: (SEQ ID NO: without leader sequence) |
|---|---|---|---|---|
| 3D8 | L | I | mdmmvpaqllgllllwfpgsrcDIQMTQSPSSVSASVGDRVTITCRASQGISSWLAWYQHKPGKAPKLLIYAASSLQSGVPSRFSGSGSGTDFTLTISSLQPEDFATYYCQQANSFPWTFGQGTKVEIK | SEQ ID NO:43 (SEQ ID NO:4) |
| | | II | mdmrvlaqllglllcfpgarcDIQMTQSPSSLSASVGDRVTITCRASQGISSWLAWYQQKPEKAPKSLIYAASSLQSGVPSRFSGSGSGTDFTLTISSLQPEDFATYYCQQYNSYPWTFGQGTKVEIK | SEQ ID NO:44 (SEQ ID NO:30) |
| | | III | mdmrvpaqllgllllwlpgarcVIWMTQSPSLLSASTGDRVTISCRMSQGISSYLAWYQQKPGKAPELLIYAASTLQSGVPSRFSGSGSGTDFTLTISSLQPEDFATYYCQQYNSYPWTFGQGTKVEIK | SEQ ID NO:45 (SEQ ID NO:31) |
| | | IV | mdmmvpaqllgllllwfpgsrcDIQMTQSPSSVSASVGDRVTITCRASQGISSWLAWYQHKPGKAPKLLIYAASSLQSGVPSRFSGSGSGTDFTLTISSLQPEDFATYYCQQYNSYPWTFGQGTKVEIK | SEQ ID NO:46 (SEQ ID NO:32) |
| | | V | mdmrvpaqllglllcfpgarcDIQMTQSPSSVSASVGDRVTITCRASQGISSWLAWYQQKPEKAPKSLIYAASSLQSGVPSRFSGSGSGTDFTLTISSLQPEDFATYYCQQYNSYPWTFGQGTKVEIK | SEQ ID NO:47 (SEQ ID NO:33) |
| | | VI | mdmrvlaqllglllcfpgarcDIQMTQSLSSLSASVGDRVTITCRASQGISSWLAWYQQKPEKAPKSLIYAASSLQSGVPSRFSGSGSGTDFTLTISSLQPEDFATYYCQQANSFPWTFGQGTKVEIK | SEQ ID NO:48 (SEQ ID NO:34) |
| | H | | mefglswvflvallrgvqcQVQLVESGGGVVQPGRSLRLSCAASGFSFSNYGMIHWVRQAPGKGLEWVALIWYDGSNEDYTDSVKGRFTISRDNSKNTLYLQMNSLRAEDTAVYYCARWGMVRGVIDVFDIWGQGTVVTVSS | SEQ ID NO:49 (SEQ ID NO:1) |
| 1B11 | L | | meapaqllflllwlpdttgEIVLTQSPATLSLSPGERATLSCRASQSVSSYLAWYQQKPGQAPRLLIYDASNRATGIPARFSGSGSGTDFTLTISSLEPEDFAVYYCQQRSNWSQFTFGPGTKVDIK | SEQ ID NO:50 (SEQ ID NO:5) |
| | H | | mefglswvflvallrgvqcQMQLVESGGGVVQPGRSLRLSCEASGFSFNSYGMIHWVRQAPGKGLEWVSVIWASGNKKYYIESVEGRFTISRDNSKNTLYLQMNSLRAEDTAVYYCARANFDYWGQGTLVTVSS | SEQ ID NO:51 (SEQ ID NO:2) |
| 33.3H2 | L | | mdmrvlaqllglllcfpgarcDIQMTQSPSSLSASVGDRVTITCRASQGISSWLAWYQQKPEKAPKSLIYAASSLQSGVPSRFSGSGSGTDFTLTISSLQPEDFATYYCQQYKSYPVTFGGGTKVEIK | SEQ ID NO:52 (SEQ ID NO:6) |
| | H | | mefglswvflvallrgvqcQVQLVESGGGVVQPGRSLRLSCAASGFTFNKYGMHWVRQAPGKGLEWVAVIWYDGTNKYYADSMKGRFTISRDNSKNMLYLQMNSLRAEDTAVYYCARDPPTANYWGQGTLVTVSS | SEQ ID NO:53 (SEQ ID NO:3) |

FIG. 2A

Anti-Toxin A 3D8 VK Sequences

```
V-segment:    L19
J-segment:    JK1
```

```
         D   I   Q   M   T   Q   S   P   S   S   V   S   A   S   V   G   D   R
  1     GAC ATC CAG ATC ACC CAG TCT CCA TCT TCC GTG TCT GCA TCT GTA GGA GAC AGA
                                        CDR1
                                        ~~~~~~~~~~~~~~~~~~~~~~~~~~~~~~~~
         V   T   I   T   C   R   A   S   Q   G   I   S   S   W   L   A   W   Y
 55     GTC ACC ATC ACT TGT CGG GCG AGT CAG GGT ATT AGC AGC TGG TTA GCC TGG TAT
                                                                    CDR2
                                                                    ~~~~~~~~~~~~~~~~~~~
         Q   H   K   P   G   K   A   P   K   L   L   I   Y   A   A   S   S   L
109     CAG CAT AAA CCA GGG AAA GCC CCT AAG CTC CTG ATC TAT GCT GCA TCC AGT TTG

CDR2
        ~~~~~~~~
         Q   S   G   V   P   S   R   F   S   G   S   G   S   G   T   D   F   T
163     CAA AGT GGG GTC CCA TCA AGG TTC AGC GGC AGT GGA TCT GGG ACA GAT TTC ACT
                                                                            CDR3
                                                                            ~~~~~~~~
         L   T   I   S   S   L   Q   P   E   D   F   A   T   Y   Y   C   Q   Q
217     CTC ACC ATC AGC AGC CTG CAG CCT GAA GAT TTT GCA ACT TAC TAT TGT CAA CAG

CDR3
        ~~~~~~~~~~~~~~~~~~~~~~~~~~~~~~~~~
         A   N   S   F   P   W   T   F   G   Q   G   T   K   V   E   I   K
271     GCT AAT AGT TTC CCT TGG ACG TTC GGC CAA GGG ACC AAG GTG AAA ATC AAA
```

→ JK1

Amino acid sequence = SEQ ID NO:4
Nucleic acid sequence = SEQ ID NO:35

FIG. 2B

Anti-Toxin A 3D8 VH Sequences

V-segment: VH3-33
D-segment: D3-10
J-segment: JH3b

```
      Q   V   Q   L   V   E   S   G   G   G   V   V   Q   P   G   R   S   L
  1   CAG GTG CAG CTG GTG GAG TCT GGG GGA GGC GTG GTC CAG CCT GGC AGG TCC CTG
                                                                CDR1
                                                      ~~~~~~~~~~~~~~~~~~~~
      R   L   S   C   A   A   S   G   F   S   F   S   N   Y   G   M   H   W
 55   AGA CTC TCC TGT GCG GCG TCT GGA TTC AGC TTC AGT AAC TAT GGC ATG CAC TGG
                                                                    CDR2
                                                          ~~~~~~~~~~~~~~~~~~
      V   R   Q   A   P   G   K   G   L   E   W   V   A   L   I   W   Y   D
109   GTC CGC CAG GCT CCA GGC AAG GGG CTG GAG TGG GTG GCA CTT ATA TGG TAT GAT
                 CDR2
      ~~~~~~~~~~~~~~~~~~~~~~~~~~~~~~~~~~~~~~~~~~~~~~~~~
      G   S   N   E   D   Y   T   D   S   V   K   G   R   F   T   I   S   R
163   GGA AGT AAT GAG GAC TAT ACA GAC TCC GTG AAG GGC CGA TTC ACC ATC TCC AGA

D   N   S   K   N   T   L   Y   L   Q   M   N   S   L   R   A   E   D
217   GAC AAT TCC AAG AAC ACG CTG TAT CTG CAA ATG AAC AGC CTG AGA GCC GAG GAC
                                                              CDR3
                                                  ~~~~~~~~~~~~~~~~~~~~~~~~~
      T   A   V   Y   Y   C   A   R   W   G   M   V   R   G   V   I   D   V
271   ACG GCT GTG TAT TAC TGT GCG AGA TGG GGG ATG GTT CGG GGA GTT ATG GAT GTT
                                              |    D3-10/DXP'1        |
                                                                       └→ JH3b
         CDR3
      ~~~~~~~~~~~~
      F   D   I   W   G   Q   G   T   V   V   T   V   S   S
325   TTT GAT ATC TGG GGC CAA GGG ACA GTG GTC ACC GTC TCT TCA
``` amino acid sequence=SEQ ID NO:1
nucleic acid sequence=SEQ ID NO:38

FIG. 3A

Anti-Toxin A 1B11 VK Sequences

```
V-segment:  L6
J-segment:  JK3
```

|     | E | I | V | L | T | Q | S | P | A | T | L | S | L | S | P | G | E | R |
|-----|---|---|---|---|---|---|---|---|---|---|---|---|---|---|---|---|---|---|
| 1   | GAA | ATT | GTG | TTG | ACA | CAG | TCT | CCA | GCC | ACC | CTG | TCT | TTG | TCT | CCA | GGG | GAA | AGA |

CDR1

|     | A | T | L | S | C | R | A | S | Q | S | V | S | S | Y | L | A | W | Y |
|-----|---|---|---|---|---|---|---|---|---|---|---|---|---|---|---|---|---|---|
| 55  | GCC | ACC | CTC | TCC | TGC | AGG | GCC | AGT | CAG | AGT | GTT | AGC | AGC | TAC | TTA | GCC | TGG | TAC |

CDR2

|     | Q | Q | K | P | G | Q | A | P | R | L | L | I | Y | D | A | S | N | R |
|-----|---|---|---|---|---|---|---|---|---|---|---|---|---|---|---|---|---|---|
| 109 | CAA | CAG | AAA | CCT | GGC | CAG | GCT | CCC | AGG | CTC | CTC | ATC | TAT | GAT | GCA | TCC | AAC | AGG |

CDR2

|     | A | T | G | I | P | A | R | F | S | G | S | G | S | G | T | D | F | T |
|-----|---|---|---|---|---|---|---|---|---|---|---|---|---|---|---|---|---|---|
| 163 | GCC | ACT | GGC | ATC | CCA | GCC | AGG | TTC | AGT | GGC | AGT | GGG | TCT | GGG | ACA | GAC | TTC | ACT |

CDR3

|     | L | T | I | S | S | L | E | P | E | D | F | A | V | Y | Y | C | Q | Q |
|-----|---|---|---|---|---|---|---|---|---|---|---|---|---|---|---|---|---|---|
| 217 | CTC | ACC | ATC | AGC | AGC | CTA | GAG | CCT | GAA | GAT | TTT | GCA | GTT | TAT | TAC | TGT | CAG | CAG |

CDR3

|     | R | S | N | W | S | Q | F | T | F | G | P | G | T | K | V | D | I | K |
|-----|---|---|---|---|---|---|---|---|---|---|---|---|---|---|---|---|---|---|
| 271 | CGT | AGC | AAC | TGG | TCT | CAA | TTC | ACT | TTC | GGC | CCT | GGG | ACC | AAA | GTG | GAT | ATC | AAA |

JK3

Amino acid sequence = SEQ ID NO:5
Nucleic acid sequence = SEQ ID NO:36

FIG. 3B

Anti-Toxin A 1B11 VH Sequences

```
V-segment:  VH3-33
D-segment:  unknown
J-segment:  JH4b
```

```
        Q   M   Q   L   V   E   S   G   G   G   V   V   Q   P   G   R   S   L
1       CAG ATG CAG CTG GTG GAG TCT GGG GGC GGC GTG GTC CAG CCT GGG AGG TCC CTG

CDR1
                                                                    ~~~~~~~~~~~~~~~~~
        R   L   S   C   E   A   S   G   F   S   F   N   S   Y   G   M   H   W
55      AGA CTC TCC TGT GAA GCG TCT GGA TTC TCC TTC AAT AGC TAT GGC ATG CAC TGG

CDR2
                                                                    ~~~~~~~~~~~~~~~~
        V   R   Q   A   P   G   K   G   L   E   W   V   S   V   I   W   A   S
109     GTC CGC CAG GCT CCA GGC AAG GGG CTG GAG TGG GTG TCA GTC ATA TGG GCC AGT

CDR2
        ~~~~~~~~~~~~~~~~~~~~~~~~~~~~~~~~~~~~~~~~~~~~~~~~~~~
        G   N   K   K   Y   Y   I   E   S   V   E   G   R   F   T   I   S   R
163     GGA AAT AAG AAA TAT TAT ATA GAA TCC GTG GAG GGC CGA TTC ACC ATC TCC AGA

D   N   S   K   N   T   L   Y   L   Q   M   N   S   L   R   A   E   D
217     GAC AAT TCC AAG AAC ACG CTG TAT CTG CAA ATG AAC AGC CTG AGA GCC GAG GAC

CDR3
                                                    ~~~~~~~~~~~~~~~~~~~~~
        T   A   V   Y   Y   C   A   R   A   N   F   D   Y   W   G   Q   G   T
271     ACG GCT GTG TAT TAC TGT GCG AGA GCC AAT TTT GAC TAC TGG GGC CAG GGA ACC
                                                    └──→ JH4b

L   V   T   V   S   S
325     CTG GTC ACC GTC TCC TCA
```

Amino acid sequence = SEQ ID NO:2
Nucleic acid sequence = SEQ ID NO:39

FIG. 4A

Anti-Toxin A 33.3H2 VK Sequences

V-segment: L15
J-segment: JK4

```
        D    I    Q    M    T    Q    S    P    S    S    L    S    A    S    V    G    D    R
  1     GAC  ATC  CAG  ATG  ACC  CAG  TCT  CCA  TCC  TCA  CTG  TCT  GCA  TCT  GTA  GGA  GAC  AGA
                                              CDR1
                                     ~~~~~~~~~~~~~~~~~~~~~~~~~~~~~~~~~~~~~~~~~~~~~~~~
        V    T    I    T    C    R    A    S    Q    G    I    S    S    W    L    A    W    Y
 55     GTC  ACC  ATC  ACT  TGT  CGG  GCG  AGT  CAG  GGT  ATT  AGC  AGC  TGG  TTA  GCC  TGG  TAT
                                                                                         CDR2
                                                                                ~~~~~~~~~~~~~~~
        Q    Q    K    P    E    K    A    P    K    S    L    I    Y    A    A    S    S    L
109     CAG  CAG  AAA  CCA  GAG  AAA  GCC  CCT  AAG  TCC  CTG  ATC  TAT  GCT  GCA  TCC  AGT  TTG

CDR2
        ~~~~~~~~~~
        Q    S    G    V    P    S    R    F    S    G    S    G    S    G    T    D    F    T
163     CAA  AGT  GGG  GTC  CCA  TCA  AGG  TTC  AGC  GGC  AGT  GGA  TCT  GGG  ACA  GAT  TTC  ACT
                                                                                         CDR3
                                                                                       ~~~~~~~~
        L    T    I    S    S    L    Q    P    E    D    F    A    T    Y    Y    C    Q    Q
217     CTC  ACC  ATC  AGC  AGC  CTG  CAG  CCT  GAA  GAT  TTT  GCA  ACT  TAT  TAC  TGC  CAA  CAG

CDR3
        ~~~~~~~~~~~~~~~~~~~~~~~~~~
        Y    K    S    Y    P    V    T    F    G    G    G    T    K    V    E    I    K
271     TAT  AAG  AGT  TAC  CCG  GTC  ACT  TTC  GGC  GGA  GGG  ACC  AAG  GTG  GAG  ATC  AAA
                              └──► JK4
```

Amino acid sequence = SEQ ID NO:6
Nucleic acid sequence = SEQ ID NO:37

FIG. 4B

Anti-Toxin A 33.3H2 VH Sequences

```
V-segment:  VH3-33
D-segment:  Unknown
J-segment:  JH4b
```

```
        Q   V   Q   L   V   E   S   G   G   G   V   V   Q   P   G   R   S   L
  1     CAG GTG CAG CTG GTG GAG TCT GGG GGA GGC GTG GTC CAG CCT GGC AGG TCC CTG

CDR 1
                                                        ~~~~~~~~~~~~~~~~~~~~~
        R   L   S   C   A   A   S   G   F   T   F   N   K   Y   G   M   H   W
  55    AGA CTC TCC TGT GCA GCG TCT GGA TTC ACC TTC AAT AAA TAT GGC ATG CAC TGG

CDR 2
                                                        ~~~~~~~~~~~~~~~~~~~~~
        V   R   Q   A   P   G   K   G   L   E   W   V   A   V   I   W   Y   D
  109   GTC CGC CAG GCT CCA GGC AAG GGG CTG GAG TGG GTG GCA GTT ATA TGG TAT GAT

CDR 2
        ~~~~~~~~~~~~~~~~~~~~~~~~~~~~~~~~~~~~~~~~~~~~~
        G   T   N   K   Y   Y   A   D   S   M   K   G   R   F   T   I   S   R
  163   GGA ACT AAT AAA TAC TAT GCA GAC TCC ATG AAG GGC CGA TTC ACC ATC TCC AGA

D   N   S   K   N   M   L   Y   L   Q   M   N   S   L   R   A   E   D
  217   GAC AAT TCC AAG AAT ATG CTG TAT CTG CAA ATG AAC AGC CTA AGA GCC GAG GAC

CDR 3
                                                        ~~~~~~~~~~~~~~~~~~~~~
        T   A   V   Y   Y   C   A   R   D   P   P   T   A   N   Y   W   G   Q
  271   ACG GCT GTG TAT TAC TGT GCG AGA GAT CCC CCC ACT GCT AAC TAC TGG GGC CAG
                                                                  ↳ JH4b

G   T   L   V   T   V   S   S
  325   GGA ACC CTG GTC ACC GTC TCC TCA
```

Amino acid sequence = SEQ ID NO:3
Nucleic acid sequence = SEQ ID NO:40

Neutralization of TxA Cytotoxicity against IMR-90 Cells

♦ 1B11
■ 3D8
▲ 3H2
✳ toxin A only

Toxin A Concentration (µg/ml)

CPE Score

FIG. 6B

Neutralization of TxA Cytotoxicity against T-84 Cells

♦ 1B11
■ 3D8
▲ 3H2
✕ ToxA alone

Toxin A Concentration (pg/ml)

CPE Score

Fragment 1 - Enzymatic

- 1-659  +
- 1-540  +
- 1-415  −
- 1-290  −
- 1-165 (from last expt.)  −

1B11 epitope = AA 415-540.

FIG. 8B

Fragment 2 - Unknown

- 660-1255  +
- 660-1146  +
- 660-1033  +
- 660-920  −
- 660-807  −

3H2 epitope = AA 920-1033

FIG. 9

Summary of mouse protection from Toxin A lethality by 1B11, 3D8, and 3H2.

| TxA lot # (dose) | Control (Synagis) | 3D8 % survival (dose*) | 3H2 % survival (dose*) | 1B11, % survival (dose*) |
|---|---|---|---|---|
| 0100005 (100 ng) | 10 | 80 | | 50 |
| 0100005 (100 ng) | 40 | 100 | | |
| 0100005 (100 ng) | 0 | | 100 | |
| 0100005 (100 ng) | 50 | | 100 | |
| 0100005 (100 ng) | 10 | 10-50 (250, 50, 10) | 60 (50) | 0-60 (250, 50, 10) |
| 1002047 (500 ng) | 30 | 10-80 (250, 25, 2.5) | 20-40 (250, 25, 2.5) | 0-30 (250, 25, 2.5) |
| 1002047 (300 ng) | 20 | 40, 30 (500, 50) | 90, 30 (150, 15) | 40, 20 (500, 50) |
| 1002047 (100 ng) | 30 | 80, 70 (250, 25) | 90, 80 (250, 25) | |
| 1002047 (100 ng) | 30 | 30, 40 (250, 25) | 100, 80 (250, 25) | |
| 1002047 (100 ng) | 25 | 50, 10, 10 (100, 10, 1) | 90, 40, 10 (100, 10, 1) | 10, 10, 30 (100, 10, 1) |
| 1002047 (100 ng) | 15 | 50, 50, 20 (100, 10, 1) | 90, 60, 60 (100, 10, 1) | |
| 1002047 (100 ng) | 15 | 60, 60, 40*** (100, 10, 1) | | |

*HuMAb dose was 250 μg unless otherwize noted
** HuMAbs were injected 24 hours prior to challenge
*** expressed from CHO cells

FIG. 17

Hamster Immunization with Toxin B fragment 4 / Relapse
Protection (Survival) Experiment — no treatment (6)
— Vancomycin (20)
— Vancomycin +3D8 (19)

FIG. 18

Hamster Immunization with Toxin B fragment 4 / Relapse Protection Experiment (illness)

FIG. 22

*C. difficile* Toxin A Amino Acid Sequence
(See also GenBank® GI No:98593, Acc. No:A37052)

```
MSLISKEELIKLAYSIRPRENEYKTILTNLDEYNKLTTNNNENKYLQLKKLNESIDVFMNKY
KTSSRNRALSNLKKDILKEVILIKNSNTSPVEKNLHFVWIGGEVSDIALEYIKQWADINAEY
NIKLWYDSEAFLVNTLKKAIVESSTTEALQLLEEEIQNPQFDNMKFYKKRMEFIYDRQKRFI
NYYKSQINKPTVPTIDDIIKSHLVSEYNRDETVLESYRTNSLRKINSNHGIDIRANSLFTEQ
ELLNIYSQELLNRGNLAAASDIVRLLALKNFGGVYLDVDMLPGIHSDLFKTISRPSSIGLDR
WEMIKLEAIMKYKKYINNYTSENFDKLDQQLKDNFKLIIESKSEKSEIFSKLENLNVSDLEI
KIAFALGSVINQALISKQGSYLTNLVIEQVKNRYQFLNQHLNPAIESDNNFTDTTKIFHDSL
FNSATAENSMFLTKIAPYLQVGFMPEARSTISLSGPGAYASAYYDFINLQENTIEKTLKASD
LIEFKFPENNLSQLTEQEINSLWSFDQASAKYQFEKYVRDYTGGSLSEDNGVDFNKNTALDK
NYLLNNKIPSNNVEEAGSKNYVHYIIQLQGDDISYEATCNLFSKNPKNSIIIQRNMNESAKS
YFLSDDGESILELNKYRIPERLKNKEKVKVTFIGHGKDEFNTSEFARLSVDSLSNEISSFLD
TIKLDISPKNVEVNLLGCNMFSYDFNVEETYPGKLLLSIMDKITSTLPDVNKNSITIGANQY
EVRINSEGRKELLAHSGKWINKEEAIMSDLSSKEYIFFDSIDNKLKAKSKNIPGLASISEDI
KTLLLDASVSPDTKFILNNLKLNIESSIGDYIYYEKLEPVKNIIHNSIDDLIDEFNLLENVS
DELYELKKLNNLDEKYLISFEDISKNNSTYSVRFINKSNGESVYVETEKEIFSKYSEHITKE
ISTIKNSIITDVNGNLLDNIQLDHTSQVNTLNAAFFIQSLIDYSSNKDVLNDLSTSVKVQLY
AQLFSTGLNTIYDSIQLVNLISNAVNDTINVLPTITEGIPIVSTILDGINLGAAIKELLDEH
DPLLKKELEAKVGVLAINMSLSIAATVASIVGIGAEVTIFLLPIAGTSAGIPSLVNNELILH
DKATSVVNYFNHLSESKKYGPLKTEDDKILVPIDDLVISEIDFNNNSIKLGTCNILAMEGGS
GHTVTGNIDHFFSSPSISSHIPSLSIYSAIGIETENLDFSKKIMMLPNAPSRVFWWETGAVP
GLRSLENDGTRLLDSIRDLYPGKFYWRFYAFFDYAITTLKPVYEDTNIKIKLDKDTRNFIMP
TITTNEIRNKLSYSFDGAGGTYSLLLSSYPISTNINLSKDDLWIFNIDNEVREISIENGTIK
KGKLIKDVLSKIDINKNKLIIGNQTIDFSGDIDNKDRYIFLTCELDDKISLIIEINLVAKSY
SLLLSGDKNYLISNLSNTIEKINTLGLDSKNIAYNYTDESNNKYFGAISKTSQKSIIHYKKD
SKNILEFYNDSTLEFNSKDFIAEDINVFMKDDINTITGKYYVDNNTDKSIDFSISLVSKNQV
KVNGLYLNESVYSSYLDFVKNSDGHHNTSNFMNLFLDNISFWKLFGFENINFVIDKYFTLVG
KTNLGYVEFICDNNKNIDIYFGEWKTSSSKSTIFSGNGRNVVVEPIYNPDTGEDISTSLDFS
YEPLYGIDRYINKVLIAPDLYTSLININTNYYSNEYYPEIIVLNPNTFHKKVNINLDSSSFE
YKWSTEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIEFNLVTGWQTINGK
KYYFDINTGAALTSYKIINGKHFYFNNDGVMQLGVFKGPDGFEYFAPANTQNNNIEGQAIVY
QSKFLTLNGKKYYFDNNSKAVTGWRIINNEKYYFNPNNAIAAVGLQVIDNNKYYFNPDTAII
SKGWQTVNGSRYYFDTDTAIAFNGYKTIDGKHFYFDSDCVVKIGVFSTSNGFEYFAPANTYN
NNIEGQAIVYQSKFLTLNGKKYYFDNNSKAVTGWQTIDSKKYYFNTNTAEAATGWQTIDGKK
YYFNTNTAEAATGWQTIDGKKYYFNTNTAIASTGYTIINGKHFYFNTDGIMQIGVFKGPNGF
EYFAPANTDANNIEGQAILYQNEFLTLNGKKYYFGSDSKAVTGWRIINNKKYYFNPNNAIAA
IHLCTINNDKYYFSYDGILQNGYITIERNNFYFDANNESKMVTGVFKGPNGFEYFAPANTHN
NNIEGQAIVYQNKFLTLNGKKYYFDNDSKAVTGWQTIDGKKYYFNLNTAEAATGWQTIDGKK
YYFNLNTAEAATGWQTIDGKKYYFNTNTFIASTGYTSINGKHFYFNTDGIMQIGVFKGPNGF
EYFAPANTDANNIEGQAILYQNKFLTLNGKKYYFGSDSKAVTGLRTIDGKKYYFNTNTAVAV
TGWQTINGKKYYFNTNTSIASTGYTIISGKHFYFNTDGIMQIGVFKGPDGFEYFAPANTDAN
NIEGQAIRYQNRFLYLHDNIYYFGNNSKAATGWVTIDGNRYYFEPNTAMGANGYKTIDNKNF
YFRNGLPQIGVFKGSNGFEYFAPANTDANNIEGQAIRYQNRFLHLLGKIYYFGNNSKAVTGW
QTINGKVYYFMPDTAMAAAGGLFEIDGVIYFFGVDGVKAPGIYG        (SEQ ID NO:41)
```

FIG. 23

*C. difficile* Toxin B Amino Acid Sequence
(See also GenBank® GI No: 7476000, Acc. No: S70172)

```
MSLVNRKQLEKMANVRFRVQEDEYVAILDALEEYHNMSENTVVEKYLKLKDINSLTDTYIDT
YKKSGRNKALKKFKEYLVIEILELKNSNLTPVEKNLHFIWIGGQINDTAINYINQWKDVNSD
YNVNVFYDSNAFLINTLKKTIIESASNDTLESFRENLNDPEFNHTAFFRKRMQIIYDKQQNF
INYYKAQKEENPDLIIDDIVKTYLSNEYSKDIDELNAYIEESLNKVTENSGNDVRNFEEFKT
GEVFNLYEQESVERWNLAGASDILRVAILKNIGGVYLDVDMLPGIHPDLFKDINKPDSVKTA
VDWEEMQLEAIMKHKEYIPEYTSKHFDTLDEEVQSSFESVLASKSDKSEIFLPLGDIEVSPL
EVKIAFAKGSIINQALISAKDSYCSDLLIKQIQNRYKLLNDTLGPIISQGNDFNTTMNNFGE
SLGAIANEENISFIAKIGSYLRVGFYPEANTTITLSGPTIYAGAYKDLLTFKEMSIDTSILS
SELRNFEFPKVNISQATEQEKNSLWQFNEERAKIQFEEYKKNYFEGALGEDDNLDFSQNTVT
DKEYLLEKISSSTKSSEGGYVHYIVQLQGDKISYEAACNLFAKNPYDSILFQRNIEDSEVAY
YYNPTDSEIQEIDKYRIPDRISDRPKIKLTFIGHGKAEFNTDIFAGLDVDSLSSEIETAIGL
AKEDISPKSIEINLLGCNMFSYSVNVEETYPGKLLLRVKDKVSELMPSMSQDSIIVSANQYE
VRINSEGRRELLDHSGEWINKEESIIKDISSKEYISFNPKENKIIVKSKNLPELSTLLQEIR
NNSNSSDIELEEKVMLAECEINVISNIETQVVEERIEEAKSLTSDSINYIKNEFKLIESISE
ALCDLKQQNELEDSHFISFEDISETDEGFSIRFINKETGESIFVETEKTIFSEYANHITEEI
SKIKGTIFDTVNGKLVKKVNLDTTHEVNTLNAAFFIQSLIEYNSSKESLSNLSVAMKVQVYA
QLFSTGLNTITDAAKVVELVSTALDETIDLLPTLSEGLPIIATIIDGVSLGAAIKELSETSD
PLLRQEIEAKIGIMAVNLTTATTAIITSSLGIASGFSILLVPLAGISAGIPSLVNNELVLRD
KATKVVDYFKHVSLVETEGVFTLLDDKVMMQQDDLVISEIDFNNNSIVLGKCEIWRMEGGSG
HTVTDDIDHFFSAPSITYREPHLSIYDVLEVQKEELDLSKDLMVLPNAPNRVFAWETGWTPG
LRSLENDGTKLLDRIRDNYEGEFYWRYFAFIADALITTLKPRYEDTNIRINLDSNTRSFIVP
IITTEYIREKLSYSFYGSGGTYALPLSQYNMGINIELSESDVWIIDVDNVVRDVTIESDKIK
KGDLIEGILSTLSIEENKIILNSHEINFSGEVNGSNGFVSLTFSILEGINAIIEVDLLSKSY
KLLISGELKILMLNSNHIQQKIDYIGFNSELQKNIPYSFVDSEGKENGFINGSTKEGLFVSE
LPDVVLISKVYMDDSKPSFGYYSNNLKDVKVITKDNVNILTGYYLKDDIKISLSLTLQDEKT
IKLNSVHLDESGVAEILKFMNRKGSTNTSDSLMSFLESMNIKSIFVNFLQSNIKFILDANFI
ISGTTSIGQFEFICDENNNIQPYFIKFNTLETNYTLYVGNRQNMIVEPNYDLDDSGDISSTV
INFSQKYLYGIDSCVNKVVISPNIYTDEINITPVYETNNTYPEVIVLDANYINEKINVNIND
LSIRYVWSNDGNDFILMSTSEENKVSQVKIRFVNVFKDKTLANKLSFNFSDKQDVPVSEIIL
SFTPSYYEDGLIGYDLGLVSLYNEKFYINNFGMMVSGLIYINDSLYYFKPPVNNLITGFVTV
GDDKYYFNPINGGAASIGETIIDDKNYYFNQSGVLQTGVFSTEDGFKYFAPANTLDENLEGE
AIDFTGKLIIDENIYYFEDNYRGAVEWKELDGEMHYFSPETGKAFKGLNQIGDDKYYFNSDG
VMQKGFVSINDNKHYFDDSGVMKVGYTEIDGKHFYFAENGEMQIGVFNTEDGFKYFAHHNED
LGNEEGEEISYSGILNFNNKIYYFDDSFTAVVGWKDLEDGSKYYFDEDTAEAYIGLSLINDG
QYYFNDDGIMQVGFVTINDKVFYFSDSGIIESGVQNIDDNYFYIDDNGIVQIGVFDTSDGYK
YFAPANTVNDNIYGQAVEYSGLVRVGEDVYYFGETYTIETGWIYDMENESDKYYFVPETKKA
CKGINLIDDIKYYFDEKGIMRTGLISFENNNYYFNENGEIQFGYINIEDKMFYFGEDGVMQI
GVFNTPDGFKYFAHQNTLDENFEGESINYTGWLGLDEKRYYFTDEYIAATGSVIIDGEEYYF
DPDTAQLVISE
```

Neutralization of Toxin B Cytotoxicity against IMR-90 Cells
Using 2A11, 124-152 or 1G10

Anti-CDTox B 124-152 VH

Fig. 28

V segment: 5-51
D segment: 7-27
J segment: JH3b

```
      E   V   Q   L   V   Q   S   G   A   E   V   K   K   S   G   E   S   L
  1 GAG GTG CAG CTG GTG CAG TCT GGA GCA GAG GTG AAA AAG TCC GGG GAG TCT CTG
                                                          CDR1  SEQ ID NO:62 (aa) 63 (nt)
                                                          ~~~~~~~~~~~~~~~~~~~~
      K   I   S   C   K   G   S   G   Y   S   F   T   S   Y   W   I   G   W
 55 AAG ATC TCC TGT AAG GGT TCT GGA TAC AGC TTT ACC AGC TAC TGG ATC GGC TGG
                                                                       CDR2
      V   R   Q   M   P   G   K   G   L   E   W   M   G   I   F   Y   P   G
109 GTG CGC CAG ATG CCC GGG AAG GGC CTG GAG TGG ATG GGG ATC TTC TAT CCT GGT
                  CDR2   SEQ ID NO:64 (aa) 65 (nt)
      ~~~~~~~~~~~~~~~~~~~~~~~~~~~~~~~~~
      D   S   S   T   R   Y   S   P   S   F   Q   G   Q   V   T   I   S   A
163 GAC TCT AGT ACC AGA TAC AGC CCG TCC TTC CAA GGC CAG GTC ACC ATC TCA GCC

D   K   S   V   N   T   A   Y   L   Q   W   S   S   L   K   A   S   D
217 GAC AAG TCC GTC AAC ACC GCC TAC CTG CAG TGG AGC AGC CTG AAG GCC TCG GAC
                                                          CDR3   SEQ ID NO:66 (aa) 67 (nt)
                                                          ~~~~~~~~~~~~~~~~~~~~
      T   A   M   Y   Y   C   A   R   R   R   N   W   G   N   A   F   D   I
271 ACC GCC ATG TAT TAC TGT GCG AGA CGT CGA AAC TGG GGA AAT GCT TTT GAT ATC

W   G   Q   G   T   M   V   T   V   S   S    SEQ ID NO:54
325 TGG GGC CAA GGG ACA ATG GTC ACC GTC TCT TCA    SEQ ID NO:55
```

>CDTox B, 124-152, VH-NT with leader SEQ ID NO:57
ATGGGGTCAACCGCCATCCTCGCCCTCCTCCTGGCTGTTCTCCAAGGAGTCTGTGCCGAGCTCCA
GCTGGTGCAGTCTGGAGCAGAGGTGAAAAAGTCCGGGGAGTCTCTGAAGATCTCCTGTAAGGGTT
CTGGATACAGCTTTACCAGCTACTGGATCGGCTGGGTGCGCCAGATGCCCGGGAAGGGCCTGGAG
TGGATGGGGATCTTCTATCCTGGTGACTCTAGTACCAGATACAGCCCGTCCTTCCAAGGCCAGGT
CACCATCTCAGCCGACAAGTCCGTCAACACCGCCTACCTGCAGTGGAGCAGCCTGAAGGCCTCGG
ACACCGCCATGTATTACTGTGCGAGACGTCGAAACTGGGGAAATGCTTTTGATATCTGGGGCCAA
GGGACAATGGTCACCGTCTCTTCA >CDTox B, 124-152, VH-AA with leader SEQ ID NO:56
MGSTAILALLLAVLQGVCAEVQLVQSGAEVKKSGESL

Fig. 29

Anti-CDTox B 124-152 VK

V segment:    A27
    J segment:    JK1

SEQ ID NO:58

```
          E   I   V   L   T   Q   S   P   G   T   L   S   L   S   P   G   E   R
      1  GAA ATT GTG TTG ACG CAG TCT CCA GGC ACC CTG TCT TTG TCT CCA GGG GAA AGA
SEQ ID NO:59
                                              CDR1    SEQ ID NO:68 (aa) 69 (nt)
                                              ~~~~~~~~~~~~~~~~~~~~~~~~~~~~~~~~~~
          A   T   L   S   C   R   A   S   Q   S   V   S   S   S   Y   L   A   W
     55  GCC ACC CTC TCC TGC AGG GCC AGT CAG AGT GTT AGC AGC AGC TAC TTA GCC TGG
                                                                     CDR2
                                                                     ~~~~~~~~~~~
          Y   Q   Q   K   P   G   Q   A   P   R   L   L   I   Y   G   A   S   S
    109  TAC CAG CAG AAA CCT GGC CAG GCT CCC AGG CTC CTC ATC TAT GGT GCA TCC AGC

CDR2    SEQ ID NO:70 (aa) 71 (nt)
          ~~~~~~~~~~~
          R   A   T   G   I   P   D   R   F   S   G   S   G   S   G   T   D   F
    163  AGG GCC ACT GGC ATC CCA GAC AGG TTC AGT GGC AGT GGG TCT GGG ACA GAC TTC
                                                                            CDR3
                                                                            ~~~
          T   L   T   I   S   R   L   E   P   E   D   F   A   V   Y   Y   C   Q
    217  ACT CTC ACC ATC AGC AGA CTG GAG CCT GAA GAT TTT GCA GTG TAT TAC TGT CAG
               CDR3    SEQ ID NO:72 (aa) 73 (nt)
          ~~~~~~~~~~~~~~~~~~~~~~~~~~~~~~~~~~~~~
          Q   Y   G   S   S   T   W   T   F   G   Q   G   T   K   V   E   I   K
    271  CAG TAT GGT ACC TCA ACG TGG ACG TTC GGC CAA GGG ACC AAG GTG GAA ATC AAA
```

>CDTox B, 124-152, VK-NT with leader    SEQ ID NO:61
ATGGAAACCCCAGCGCAGCTTCTCTTCCTCCTGCTACTCTGGCTCCCAGATACCACCGGAGAAAT
TGTGTTGACGCAGTCTCCAGGCACCCTGTCTTTGTCTCCAGGGGAAAGAGCCACCCTCTCCTGCA
GGGCCAGTCAGAGTGTTAGCAGCAGCTACTTAGCCTGGTACCAGCAGAAACCTGGCCAGGCTCCC
AGGCTCCTCATCTATGGTGCATCCAGCAGGGCCACTGGCATCCCAGACAGGTTCAGTGGCAGTGG
GTCTGGGACAGACTTCACTCTCACCATCAGCAGACTGGAGCCTGAAGATTTTGCAGTGTATTACT
GTCAGCAGTATGGTAGCTCAACGTGGACGTTCGGCCAAGGGACCAAGGTGGAAATCAAA >CDTox B, 124-152, VK-AA with leader    SEQ ID NO:60
METPAQLLFLLLLWLPDTTGEIVLTQSPGTLSLSPGERATLSCRASQSVSSSYLAWYQQKPGQA
PRLLIYGASSRATGIPDRFSGSGSGTDFTLTISRLEPEDFAVYYCQQYGSSTWTFGQGTKVEIK

Fig. 30

```
Anti-CDTox B 124-152 VH region

SEQ ID NO:75
                                                              CDR1
5-51 germline  E V Q L V Q S G A E V K K P G E S L K I S C K G S G Y S F T S Y W I G W
124-152 VH     - - - - - - - - - - - S - - - - - - - - - - - - - - - - - - - - - - -

SEQ ID NO:76
                                            CDR2
5-51 germline  V R Q M P G K G L E W M G I I Y P G D S D T R Y S P S F Q G Q V T I S A
124-152 VH     - - - - - - - - - - - - - F - - - - - S - - - - - - - - - - - - - - -

SEQ ID NO:77
                                                        CDR3
5-51 germline  D K S I S T A Y L Q W S S L K A S D T A M Y Y C A R
JH3b germline                                                        A F D I
124-152 VH     - - - V N - - - - - - - - - - - - - - - - - - - - R R N W G N - - - -

JH3b germline  W G Q G T M V T V S S    SEQ ID NO:74
124-152 VH     - - - - - - - - - - -    (JH3b)
```

Fig. 31

Anti-CDTox B 124-152 VK region

```
                                                                CDR1      SEQ ID NO:78
A27 germline    E I V L T Q S P G T L S L S P G E R A T L S C R A S Q S V S S S Y L A W
124-152 VK      - - - - - - - - - - - - - - - - - - - - - - - - - - - - - - - - - - -

CDR2
A27 germline    Y Q Q K P G Q A P R L L I Y G A S S R A T G I P D R F S G S G S G T D F
124-152 VK      - - - - - - - - - - - - - - - - - - - - - - - - - - - - - - - - - - -

SEQ ID NO:80
                                                       CDR3
A27 germline    T L T I S R L E P E D F A V Y Y C Q Q Y G S S P       SEQ ID NO:79
JK1 germline                                                    W T  F G Q G T K V E I K
124-152 VK      - - - - - - - - - - - - - - - - - - - - - - - T - - - - - - - - - - -
(JK1)
```

FIG. 32

Mab 124-152 binds to the C-terminus of *C. difficile* Toxin B (TcdB)

amino acid residues: 1 — 592 | 593 — 1184 | 1185 — 1776 | 1777 — 2366 aa (Receptor binding domain)

124-152 binding

ANTIBODIES AGAINST CLOSTRIDIUM DIFFICILE TOXINS AND USES THEREOF

RELATED INFORMATION

The application is a continuation of U.S. patent application Ser. No. 12/533,501, filed on Jul. 31, 2009, now allowed, which is a divisional application of U.S. patent application Ser. No. 11/051,453, filed on Feb. 4, 2005, now U.S. Pat. No. 7,625,559, which claims priority to U.S. provisional patent application No. 60/542,357, filed on Feb. 6, 2004, and U.S. provisional patent application No. 60/613,854, filed on Sep. 28, 2004, the entire contents both of which are hereby incorporated by reference.

The contents of any patents, patent applications, and references cited throughout this specification are hereby incorporated by reference in their entireties.

BACKGROUND OF THE INVENTION

*Clostridium difficile* (*C. difficile*) is a gram-positive bacterium that causes gastrointestinal disease in humans. *C. difficile* is the most common cause of infectious diarrhea in hospital patients, and is one of the most common nosocomial infections overall (Kelly et al., *New Eng. J. Med.*, 330:257-62, 1994). In fact, disease associated with this pathogen may afflict as many as three million hospitalized patients per year in the United States (McFarland et al., *New Eng. J. Med.*, 320:204-10, 1989; Johnson et al., *Lancet*, 336:97-100, 1990).

Treatment with antibiotics such as ampicillin, amoxicillin, cephalosporins, and clindamycin that disrupt normal intestinal flora can allow colonization of the gut with *C. difficile* and lead to *C. difficile* disease (Kelly and Lamont, *Annu. Rev. Med.*, 49:375-90, 1998). The onset of *C. difficile* disease typically occurs four to nine days after antibiotic treatment begins, but can also occur after discontinuation of antibiotic therapy. *C. difficile* can produce symptoms ranging from mild to severe diarrhea and colitis, including pseudomembranous colitis (PMC), a severe form of colitis characterized by abdominal pain, watery diarrhea, and systemic illness (e.g., fever, nausea). Relapsing disease can occur in up to 20% of patients treated for a first episode of disease, and those who relapse are at a greater risk for additional relapses (Kelly and Lamont, *Annu. Rev. Med.*, 49:375-90, 1998).

*C. difficile* disease is believed to be caused by the actions of two exotoxins, toxin A and toxin B, on gut epithelium. Both toxins are high molecular weight proteins (280-300 kDa) that catalyze covalent modification of Rho proteins, small GTP-binding proteins involved in actin polymerization, in host cells. Modification of Rho proteins by the toxins inactivates them, leading to depolymerization of actin filaments and cell death. Both toxins are lethal to mice when injected parenterally (Kelly and Lamont, *Annu. Rev. Med.*, 49:375-90, 1998).

*C. difficile* disease can be diagnosed by assays that detect the presence or activity of toxin A or toxin B in stool samples, e.g., enzyme immunoassays. Cytotoxin assays can be used to detect toxin activity. To perform a cytotoxin assay, stool is filtered to remove bacteria, and the cytopathic effects of toxins on cultured cells are determined (Merz et al., *J. Clin. Microbiol.*, 32:1142-47, 1994).

*C. difficile* treatment is complicated by the fact that antibiotics trigger *C. difficile* associated disease. Nevertheless, antibiotics are the primary treatment option at present. Antibiotics least likely to cause *C. difficile* associated disease such as vancomycin and metronidazole are frequently used. Vancomycin resistance evolving in other microorganisms is a cause for concern in using this antibiotic for treatment, as it is the only effective treatment for infection with other microorganisms (Gerding, *Curr. Top. Microbiol. Immunol.*, 250:127-39, 2000). Probiotic approaches, in which a subject is administered non-pathogenic microorganisms that presumably compete for niches with the pathogenic bacteria, are also used. For example, treatment with a combination of vancomycin and *Saccharomyces boulardii* has been reported (McFarland et al., *JAMA*, 271(24):1913-8, 1994. Erratum in: *JAMA*, 272(7):518, 1994).

Vaccines have been developed that protect animals from lethal challenge in infectious models of disease (Torres et al., *Infect. Immun.* 63(12):4619-27, 1995). In addition, polyclonal antibodies have been shown to protect hamsters from disease when administered by injection or feeding (Giannasca et al., *Infect. Immun.* 67(2):527-38, 1999; Kink and Williams, *Infect. Immun.*, 66(5):2018-25, 1998). Murine monoclonal antibodies have been isolated that bind to *C. difficile* toxins and neutralize their activities in vivo and in vitro (Corthier et al., *Infect. Immun.*, 59(3):1192-5, 1991). There are some reports that human polyclonal antibodies containing toxin neutralizing antibodies can prevent *C. difficile* relapse (Salcedo et al., *Gut.*, 41(3):366-70, 1997). Antibody response against toxin A has been correlated with disease outcome, indicating the efficacy of humoral responses in controlling infection. Individuals with robust toxin A ELISA responses had less severe disease compared to individuals with low toxin A antibody levels (Kyne et al., *Lancet*, 357 (9251):189-93, 2001).

The individual role of toxin A and toxin B in disease pathogenesis, and the role of anti-toxin antibodies in protection from *C. difficile* disease are controversial and may depend on the host. In humans, the anti-toxin A antibody response has been correlated to disease outcome, suggesting a requirement for anti-toxin A response for protection. This observation is in contrast with reports of disease-causing *C. difficile* organisms that express only toxin B, implying that toxin B can contribute to disease in humans. These toxin A-negative strains can also cause disease in hamsters (Sambol et al., *J. Infect. Dis.*, 183(12):1760-6, 2001).

SUMMARY OF THE INVENTION

This invention is based, in part, on the discovery that administration of antibodies against *C. difficile* toxin A to a subject can protect the subject from relapse of *C. difficile*-mediated disease in vivo. Administration of antibodies to one or both of toxin A and toxin B can prevent primary *C. difficile*-mediated disease. High affinity antibodies against *C. difficile* toxins can be produced, e.g., in mice, such as transgenic mice expressing human immunoglobulin gene segments. These antibodies can neutralize toxin cytotoxicity in vitro, and neutralize toxin enterotoxicity in vivo. Antibodies that recognize toxin A and/or toxin B can inhibit and protect from disease in vivo.

In one aspect, the invention features isolated human monoclonal antibodies or antigen binding portions thereof that specifically bind to an exotoxin of *Clostridium difficile* (*C. difficile*). In certain embodiments, the antibodies or antigen binding portions thereof specifically bind to *C. difficile* toxin A (toxin A). In other embodiments, the antibody or antigen binding portions thereof specifically bind to *C. difficile* toxin B (toxin B). In other embodiments, the antibodies or antigen binding portions thereof specifically bind to both toxin A and toxin B.

In certain embodiments, the antibodies or antigen binding portions thereof neutralize toxin A in vitro, inhibit binding of toxin A to mammalian cells, and/or inhibit *C. difficile*-mediated disease in vivo.

In various embodiments, the antibodies or antigen binding portions thereof have one or more of the following characteristics: when administered to a mouse, they protect the mouse against administration of a *C. difficile* toxin in an amount that would be fatal to a control mouse not administered the antibody; protect from or inhibit *C. difficile*-mediated colitis, antibiotic-associated colitis, or pseudomembranous colitis (PMC) in a subject; protect from or inhibit diarrhea in a subject; and/or inhibit relapse of *C. difficile*-mediated disease.

The antibodies or antigen binding portions thereof can specifically bind to an epitope within the N-terminal half of toxin A, e.g., an epitope between amino acids 1-1256 of toxin A. In other embodiments, the antibodies or antigen binding portions thereof specifically bind to an epitope within the C-terminal receptor binding domain of toxin A, e.g., an epitope between amino acids 1852-2710 of toxin A, or an epitope between amino acids 659-1852, e.g., an epitope within amino acid residues 900-1852, 900-1200, or 920-1033 of toxin A. In other embodiments, the antibodies or antigen binding portions thereof specifically bind an epitope within amino acids 1-600, 400-600, or 415-540 of toxin A. Other particular antibodies or antigen binding portions thereof, can specifically bind to an epitope within amino acid residues 1-100, 100-200, 200-300, 300-400, 400-500, 500-600, 600-700, 700-800, 900-1000, 1100-1200, 1200-1300, 1300-1400, 1400-1500, 1500-1600, 1600-1700, 1800-1900, 1900-200, 2100-2200 or 2200-2300, 2300-2400, 2400-2500, 2500-2600, 2600-2710 of toxin A, or any interval, portion or range thereof.

In certain embodiments, the antibodies or antigen binding portions thereof specifically bind to toxin A with a $K_D$ of less than about $20 \times 10^{-6}$ M. In a particular embodiment, the antibody, or antigen binding portion thereof, specifically binds to toxin A with a $K_D$ of less than about $10 \times 10^{-7}$ M, less than about $10 \times 10^{-8}$ M, less than about $10 \times 10^{-9}$ M, or less than about $10 \times 10^{-10}$ M. In other particular embodiments, the antibody, or antigen binding portion thereof, specifically binds to toxin A with a $K_D$ of less than about $50 \times 10^{-10}$ M, less than about $20 \times 10^{-10}$ M, less than about $15 \times 10^{-10}$ M, less than about $8 \times 10^{-10}$ M, or less than about $5 \times 10^{-10}$ M.

In various other embodiments, the antibodies or antigen binding portions thereof include a variable heavy chain region including an amino acid sequence at least 80%, 85%, 90%, 95%, 98%, 99%, or more identical to a variable heavy chain region amino acid sequence of the antibody produced by clone 3D8 (SEQ ID NO:1), 1B11 (SEQ ID NO:2), or 3H2 (SEQ ID NO:3).

In certain embodiments, the antibodies or antigen binding portions thereof include a variable light chain region comprising an amino acid sequence at least 80%, 85%, 90%, 95%, 98%, 99%, or more identical to a variable light chain region amino acid sequence of the antibody produced by clone 3D8 (SEQ ID NO:4), 1B 11 (SEQ ID NO:5), or 3H2 (SEQ ID NO:6).

In certain embodiments, the antibodies or antigen binding portions thereof each include both a variable heavy chain region including an amino acid sequence at least 80%, 85%, 90%, 95%, 98%, 99%, or more identical to a variable heavy chain region amino acid sequence of the antibody produced by clone 3D8 (SEQ ID NO:1), 1B11 (SEQ ID NO:2), or 3H2 (SEQ ID NO:3), and a variable light chain region including an amino acid sequence at least 80%, 85%, 90%, 95%, 98%, 99%, or more identical to a variable light chain amino acid sequence of clone 3D8 (SEQ ID NO:4), 1B 11 (SEQ ID NO:5), or 3H2 (SEQ ID NO:6).

In various embodiments, the antibodies or antigen binding portions thereof specifically bind to an epitope that overlaps with an epitope bound by an antibody produced by clone 3D8, 1B11, or 3H2 and/or compete for binding to toxin A with an antibody produced by clone 3D8, 1B11, or 3H2.

A variable heavy chain region of the antibodies or antigen binding portions thereof can include one or more complementarity determining regions (CDRs) that are at least 80%, 85%, 90%, 95%, or 99%, or more identical to a CDR of the antibody produced by clone 3D8 (SEQ ID NOs:7-9), 1B11 (SEQ ID NOs:10-12), or 3H2 (SEQ ID NOs:13-15) (also shown in Table 1).

A variable light chain region of the antibodies or antigen binding portions thereof can include one or more CDRs that are at least 80%, 85%, 90%, 95%, or 99%, or more identical to a CDR of a variable light chain region of the antibody produced by clone 3D8 (SEQ ID NOs:16-18), 1B11 (SEQ ID NOs:19-21), or 3H2 (SEQ ID NOs:22-24) (also shown in Table 2).

A variable heavy chain region of the antibodies or antigen binding portions thereof can include one or more complementarity determining regions (CDRs) that are at least 80%, 85%, 90%, 95%, or 99%, or more identical to a CDR of the antibody produced by clone 3D8 (SEQ ID NOs:7-9), 1B11 (SEQ ID NOs:10-12), or 3H2 (SEQ ID NOs:13-15), and a variable light chain region of the antibodies or antigen binding portions thereof can include one or more CDRs that are at least 80%, 85%, 90%, 95%, 99%, or more identical to a CDR of a variable light chain region of the antibody produced by clone 3D8 (SEQ ID NOs:16-18), 1B11 (SEQ ID NOs:19-21), or 3H2 (SEQ ID NOs:22-24).

A variable heavy chain region of the antibodies or antigen binding portions thereof can include three CDRs that are at least 80%, 85%, 90%, 95%, or 99%, or more identical to a CDR of a variable heavy chain region of the antibody produced by clone 3D8 (SEQ ID NOs:7-9), 1B11 (SEQ ID NOs:10-12), or 3H2 (SEQ ID NOs:13-15).

In some embodiments, a variable light chain region of the antibodies or antigen binding portions thereof includes three CDRs that are at least 80%, 85%, 90%, 95%, 99%, or more identical to a CDR of a variable light chain region of the antibody produced by clone 3D8 (SEQ ID NOs:16-18), 1B11 (SEQ ID NOs:19-21), or 3H2 (SEQ ID NOs:22-24).

In some embodiments, a variable light chain region of the antibodies or antigen binding portions thereof includes one or more CDRs that are at least 80%, 85%, 90%, 95%, or 99%, or more identical to a CDR of a variable light chain region of the antibody produced by clone 3D8 (SEQ ID NOs:16-18), 1B11 (SEQ ID NOs:19-21), or 3H2 (SEQ ID NOs:22-24), and a variable heavy chain region of the antibodies or antigen binding portions thereof includes three CDRs that are at least 80%, 85%, 90%, 95%, or 99%, or more identical to a CDR of a variable heavy chain region of the antibody produced by clone 3D8 (SEQ ID NOs:7-9), 1B11(SEQ ID NOs:10-12), or 3H2 (SEQ ID NOs:13-15). The variable light chain region can include three CDRs that are at least 80%, 85%, 90%, 95%, or 99%, or more identical to a CDR of a variable light chain region of the antibody produced by clone 3D8 (SEQ ID NOs:16-18), 1B11 (SEQ ID NOs:19-21), or 3H2 (SEQ ID NOs:22-24).

In certain embodiments, a variable heavy chain region of the antibodies or antigen binding portions thereof includes three CDRs that are identical to a CDR of a variable heavy chain region of the antibody produced by clone 3D8 (SEQ ID NOs:7-9), 1B11 (SEQ ID NOs:10-12), or 3H2 (SEQ ID NOs:

13-15), and a variable light chain region of the antibodies or antigen binding portions thereof includes three CDRs that are identical to a CDR of a variable light chain region of the antibody produced by clone 3D8 (SEQ ID NOs:16-18), 1B11 (SEQ ID NOs:19-21), or 3H2 (SEQ ID NOs:22-24), e.g., a variable light chain region and variable heavy chain region of the antibody or antigen binding portion thereof are identical to a variable light chain region and variable heavy chain region of the antibody produced by clone 3D8 (SEQ ID NO:1, SEQ ID NO:4), 1B11 (SEQ ID NO:2, SEQ ID NO:5), or 3H2 (SEQ ID NO:3, SEQ ID NO:6).

In some embodiments, the antibodies or antigen binding portions thereof neutralize toxin B in vitro, inhibit binding of toxin B to mammalian cells, and/or neutralize toxin B in vivo.

In some embodiments, the antibodies or antigen binding portions thereof specifically bind to an epitope in a C-terminal portion of toxin B (e.g., between amino acids 1777-2366 of toxin B). Other particular antibodies or antigen binding portions thereof, can specifically bind to an epitope within amino acid residues 1-100, 100-200, 200-300, 300-400, 400-500, 500-600, 600-700, 700-800, 900-1000, 1100-1200, 1200-1300, 1300-1400, 1400-1500, 1500-1600, 1600-1700, 1800-1900, 1900-200, 2100-2200 or 2200-2366 of toxin B, or any interval, portion or range thereof.

In certain embodiments, the antibodies or antigen binding portions thereof specifically bind to toxin B with a $K_D$ of less than about $20\times10^{-6}$ M. In a particular embodiment, the antibody, or antigen binding portion thereof, specifically binds to toxin B with a $K_D$ of less than about $10\times10^{-7}$ M, less than about $10\times10^{-8}$ M, less than about $10\times10^{-9}$ M, or less than about $10\times10^{-10}$ M. In other particular embodiments, the antibody, or antigen binding portion thereof, specifically binds to toxin B with a $K_D$ of M, less than about $50\times10^{-10}$ m less than about $20\times10^{-10}$ M, less than about $15\times10^{-10}$ M, less than about $8\times10^{-10}$ M, or less than about $5\times10^{-10}$ M.

In various other embodiments, the antibodies or antigen binding portions thereof include a variable heavy chain region including an amino acid sequence that is at least 80%, 85%, 90%, 95%, 98%, 99%, or more identical to a variable heavy chain region amino acid sequence of the antibody produced by clone 124-152 (i.e., the amino acid sequence shown in SEQ ID NO:54), 2A11, or 1G10.

In certain embodiments, the antibodies or antigen binding portions thereof include a variable light chain region comprising an amino acid sequence that is at least 80%, 85%, 90%, 95%, 98%, 99%, or more identical to a variable heavy chain region amino acid sequence of the antibody produced by clone 124-152 (i.e., the amino acid sequence shown in SEQ ID NO:58), 2A11, or 1G10.

In certain embodiments, the antibodies or antigen binding portions thereof each include both a variable heavy chain region including an amino acid sequence at least 80%, 85%, 90%, 95%, 98%, 99%, or more identical to a variable heavy chain region amino acid sequence of the antibody produced by clone 124-152 (i.e., the amino acid sequence shown in SEQ ID NO:54), 2A11, or 1G10, and a variable light chain region including an amino acid sequence that is at least 80%, 85%, 90%, 95%, 98%, 99%, or more identical to a variable light chain amino acid sequence of the antibody produced by clone 124-152 (i.e., the amino acid sequence shown in SEQ ID NO:58), 2A11, or 1G10.

In various embodiments, the antibodies or antigen binding portions thereof specifically bind to an epitope that overlaps with an epitope bound by an antibody produced by clone 124-152, 2A11, or 1G10 and/or compete for binding to toxin B with an antibody produced by clone 124-152, 2A11, or 1G10.

A variable heavy chain region of the antibodies or antigen binding portions thereof can include one or more complementarity determining regions (CDRs) that are at least 80%, 85%, 90%, 95%, or 99%, or more identical to a CDR of the antibody produced by clone 124-152 (SEQ ID NOs: 62, 64, or 66), 2A11, or 1G10 (Table 3).

A variable light chain region of the antibodies or antigen binding portions thereof can include one or more complementarity determining regions (CDRs) that are at least 80%, 85%, 90%, 95%, or 99%, or more identical to a CDR of the antibody produced by clone 124-152 (SEQ ID NOs: 68, 70, or 72), 2A11, or 1G10 (Table 4).

A variable heavy chain region of the antibodies or antigen binding portions thereof can include one or more complementarity determining regions (CDRs) that are at least 80%, 85%, 90%, 95%, or 99%, or more identical to a CDR of the antibody produced by clone 124-152 (SEQ ID NOs: 62, 64, or 66), 2A11, or 1G10, and a variable light chain region of the antibodies or antigen binding portions thereof can include one or more CDRs that are at least 80%, 85%, 90%, 95%, 99%, or more identical to a CDR of a variable light chain region of the antibody produced by clone 124-152 (SEQ ID NOs: 68, 70, or 72), 2A11, or 1G10.

A variable heavy chain region of the antibodies or antigen binding portions thereof can include three CDRs that are at least 80%, 85%, 90%, 95%, or 99%, or more identical to a CDR of a variable heavy chain region of the antibody produced by clone 124-152 (SEQ ID NOs: 62, 64, or 66), 2A11, or 1G10.

In certain embodiments, the variable light chain region of the antibodies or antigen binding portions thereof includes three CDRs that are at least 80%, 85%, 90%, 95%, 99%, or more identical to a CDR of a variable light chain region of the antibody produced by clone 124-152 (SEQ ID NOs: 68, 70, or 72), 2A11, or 1G10.

In other embodiments, the variable light chain region of the antibodies or antigen binding portions thereof includes one or more CDRs that are at least 80%, 85%, 90%, 95%, or 99%, or more identical to a CDR of a variable light chain region of the antibody produced by clone 124-152 (SEQ ID NOs: 68, 70, or 72), 2A11, or 1G10, and a variable heavy chain region of the antibodies or antigen binding portions thereof includes three CDRs that are at least 80%, 85%, 90%, 95%, or 99%, or more identical to a CDR of a variable heavy chain region of the antibody produced by clone 124-152 (SEQ ID NOs: 62, 64, or 66), 2A11, or 1G10. The variable light chain region can include three CDRs that are at least 80%, 85%, 90%, 95%, or 99%, or more identical to a CDR of a variable light chain region of the antibody produced by clone 124-152 (SEQ ID NOs: 68, 70, or 72), 2A11, or 1G10.

In still other embodiments, the variable heavy chain region of the antibodies or antigen binding portions thereof includes three CDRs that are identical to a CDR of a variable heavy chain region of the antibody produced by clone 124-152 (SEQ ID NOs: 62, 64, or 66), 2A11, or 1G10, and a variable light chain region of the antibodies or antigen binding portions thereof includes three CDRs that are identical to a CDR of a variable light chain region of the antibody produced by clone 124-152 (SEQ ID NOs: 68, 70, or 72), 2A11, or 1G10, e.g., a variable light chain region and variable heavy chain region of the antibody or antigen binding portion thereof are identical to a variable light chain region and variable heavy chain region of the antibody produced by clone 124-152 (SEQ ID NOs: 62, 64, or 66), 2A11, or 1G10.

The antibodies or antigen binding portions thereof can be full-length antibodies, can include an effector domain, e.g., an Fc domain, can be immunoglobulin gamma isotype antibodies, single-chain antibodies, or Fab fragments. The antibodies or antigen binding portions thereof can further include a pharmaceutically acceptable carrier and/or a label.

In various embodiments, compositions including the antibodies or antigen binding portions thereof are free of other human polypeptides (e.g., they contain less than 5% human polypeptides other than the antibodies or antigen binding portions thereof).

In yet another aspect, the invention features compositions including: (a) an isolated human monoclonal antibody or antigen binding portion thereof that specifically binds to an exotoxin of *C. difficile*; and (b) a polyclonal antibody or antigen binding portion thereof that specifically binds to an exotoxin of *C. difficile*.

In one embodiment, the human monoclonal antibody or antigen binding portion thereof specifically binds to *C. difficile* toxin A, and the polyclonal antibody or antigen binding portion thereof specifically binds to *C. difficile* toxin B. In one embodiment, the human monoclonal antibody or antigen binding portion thereof specifically binds to *C. difficile* toxin B, and the polyclonal antibody or antigen binding portion thereof specifically binds to *C. difficile* toxin A. The antibodies can include other features described herein.

In another aspect, the invention features isolated human monoclonal antibodies or antigen binding portions thereof that specifically bind to an exotoxin of *Clostridium difficile* (*C. difficile*), wherein the antibodies: (a) include a heavy chain variable region that is the product of or derived from a human VH 3-33 gene; and/or (b) include a light chain variable region that is the product of or derived from a human Vκ gene selected from the group consisting of Vκ L19, Vκ L6 and Vκ L15. The antibodies or antigen binding portions thereof can include other features described herein.

In another aspect, the invention features isolated human monoclonal antibodies or antigen binding portions thereof that specifically bind to an exotoxin of *Clostridium difficile* (*C. difficile*), wherein the antibodies: (a) include a heavy chain variable region that is the product of or derived from a human VH 5-51 gene; and/or (b) include a light chain variable region that is the product of or derived from a human Vκ A27 gene. The antibodies or antigen binding portions thereof also can include other features described herein.

In another aspect, the invention features isolated polypeptides that include an antigen binding portion of an antibody produced by hybridoma clone 3D8, 1B11, or 3H2 (also referred to herein as "3D8", "1B11", and "3H2").

In another aspect, the invention features isolated polypeptides that include an antigen binding portion of an antibody produced by hybridoma clone 124-152, 2A11, or 1G10 (also referred to herein as "124-152", "2A11", and "1G10").

In another aspect, the invention features isolated monoclonal antibodies or antigen binding portions thereof that specifically bind to an exotoxin of *C. difficile*, neutralize the toxin, inhibit, and/or protect from *C. difficile*-mediated disease. In one embodiment, the antibodies or antigen binding portions thereof are mammalian (e.g., human) antibodies or antigen binding portions thereof. The antibodies or antigen binding portions thereof can include other features described herein.

In another aspect, the invention features compositions including: (a) an isolated human monoclonal antibody or antigen binding portion thereof that specifically binds to *C. difficile* toxin A; and (b) an isolated human monoclonal antibody or antigen binding portion thereof that specifically binds to *C. difficile* toxin B.

In another aspect, the invention features isolated nucleic acids including a sequence encoding polypeptides at least 75%, 80%, 85%, 90%, 95%, 99%, or more identical to SEQ ID NOs:1, 2, 3, 4, 5, or 6; e.g., wherein the nucleic acid sequence is at least 75%, 80%, 85%, 90%, 95%, 99%, or more identical to SEQ ID NOs:38, 39, 40, 35, 36, or 37. The invention also features expression vectors including a nucleic acid encoding a polypeptide at least 75%, 80%, 85%, 90%, 95%, 99%, or more identical to SEQ ID NOs:1, 2, 3, 4, 5, or 6; e.g., wherein the nucleic acid sequence is at least 75%, 80%, 85%, 90%, 95%, 99%, or more identical to SEQ ID NOs:38, 39, 40, 35, 36, or 37, as well as host cells, e.g., bacterial cells, e.g., *E. coli* cells, including a nucleic acid encoding a polypeptide at least 75%, 80%, 85%, 90%, 95%, 99%, or more identical to SEQ ID NOs:1, 2, 3, 4, 5, or 6; e.g., wherein the nucleic acid sequence is at least 75%, 80%, 85%, 90%, 95%, 99%, or more identical to SEQ ID NOs:38, 39, 40, 35, 36, or 37.

In another aspect, the invention features isolated nucleic acids including a sequence encoding a polypeptide that is at least 75%, 80%, 85%, 90%, 95%, 99%, or more identical to SEQ ID NOs: 54, 56, 58, or 60, for example, wherein the nucleic acid sequence is at least 75%, 80%, 85%, 90%, 95%, 99%, or more identical to SEQ ID NOs: 55, 57, 59, or 61. The invention also features expression vectors including a nucleic acid encoding a polypeptide at least 75%, 80%, 85%, 90%, 95%, 99%, or more identical to SEQ ID NOs: 54, 56, 58, or 60, for example, wherein the nucleic acid sequence is at least 75%, 80%, 85%, 90%, 95%, 99%, or more identical to SEQ ID NOs: 55, 57, 59, or 61. The invention also provides host cells, e.g., bacterial cells, e.g., *E. coli* cells, that include a nucleic acid encoding a polypeptide that is at least 75%, 80%, 85%, 90%, 95%, 99%, or more identical to SEQ ID NOs: 54, 56, 58, or 60, for example, wherein the nucleic acid sequence is at least 75%, 80%, 85%, 90%, 95%, 99%, or more identical to SEQ ID NOs: 55, 57, 59, or 61.

The host cells can also be eukaryotic cells, e.g., yeast cells, mammalian cells, e.g., Chinese hamster ovary (CHO) cells, NS0 cells, or myeloma cells.

In another aspect, the invention features kits including an isolated human monoclonal antibody or antigen binding portion thereof that specifically binds to an exotoxin of *Clostridium difficile* (*C. difficile*), e.g., an antibody or antigen binding portion thereof described herein. The kit can include instructions for use in preventing or treating *C. difficile*-mediated disease.

The kit can further include a polyclonal antibody or antigen binding portion thereof that specifically binds an exotoxin of *C. difficile*. In one embodiment, the human monoclonal antibody or antigen binding portion thereof specifically binds to *C. difficile* toxin A. In one embodiment, the polyclonal antibody or antigen binding portion thereof specifically binds to *C. difficile* toxin B.

In another aspect, the invention features kits including: (a) an isolated human monoclonal antibody that specifically binds to *C. difficile* toxin A; and (b) an isolated human monoclonal antibody that specifically binds to *C. difficile* toxin B.

The invention also features methods of treating *C. difficile* disease in a subject by administering to the subject an isolated human monoclonal antibody or antigen binding portion thereof that specifically binds to an exotoxin of *Clostridium difficile* (*C. difficile*) in an amount effective to inhibit *C. difficile* disease, e.g., *C. difficile*-mediated colitis, antibiotic-associated colitis, *C. difficile*-mediated pseudomembranous colitis (PMC), or diarrhea, or relapse of *C. difficile*-mediated disease. The antibody or antigen binding portion thereof can be administered, e.g., intravenously, intramuscularly, or subcutaneously, to the subject.

The antibody or antigen binding portion thereof can be administered alone or in combination with another therapeutic agent, e.g., a second human monoclonal antibody or antigen binding portion thereof. In one example, the antibody or antigen binding portion thereof specifically binds to *C. difficile* toxin A, and the second human monoclonal antibody or antigen binding portion thereof specifically binds to *C. difficile* toxin B. In another example, the second agent is an antibiotic, e.g., vancomycin or metronidazole. The second agent can be polyclonal gamma-globulin (e.g., human gamma-globulin).

In a particular embodiment, an antibody or antigen binding portion thereof is administered which includes a variable light chain region and a variable heavy chain region identical to the variable light chain region and variable heavy chain region of the antibody produced by clone 3D8 (i.e., including a variable light chain region sequence identical to SEQ ID NO:4 and a variable heavy chain region sequence identical to SEQ ID NO:1.

In another embodiment, this antibody or antigen binding portion thereof is administered in combination with an antibody or antigen binding portion thereof which includes a variable light chain region and a variable heavy chain region identical to the variable light chain region and variable heavy chain region of the antibody produced by clone 124-152 (i.e., including a variable light chain region sequence identical to SEQ ID NO:58 and a variable heavy chain region sequence identical to SEQ ID NO:54).

In yet another embodiment, an antibody or antigen binding portion produced by clone 3D8 (i.e., including a variable light chain region sequence identical to SEQ ID NO:4 and a variable heavy chain region sequence identical to SEQ ID NO:1), is administered in combination with an antibody or antigen binding portion thereof produced by clone 124-152 (i.e., including a variable light chain region sequence identical to SEQ ID NO:58 and a variable heavy chain region sequence identical to SEQ ID NO:54).

In another aspect, the invention features methods for making an antibody or antigen binding portion thereof that specifically binds to an exotoxin of *C. difficile*, by immunizing a transgenic non-human animal having a genome comprising a human heavy chain transgene and a human light chain transgene with a composition that includes an inactivated exotoxin, and isolating an antibody from the animal. The exotoxin can be inactivated, for example, by treatment with UDP-dialdehyde or by mutation (e.g., using recombinant methods). The method can further include evaluating binding of the antibody to the exotoxin.

The invention also features methods for making a human monoclonal antibody or antigen binding portion thereof by providing a nucleic acid encoding a human monoclonal antibody or antigen binding portion thereof that specifically binds to an exotoxin of *C. difficile*, and expressing the nucleic acid in a host cell.

In yet another aspect, the invention features a hybridoma or transfectoma including a nucleic acid encoding antigen binding portions (e.g., CDRs, or variable regions) of the antibody produced by clone 3D8, 1B11, or 3H2.

In yet another aspect, the invention features a hybridoma or transfectoma including a nucleic acid encoding antigen binding portions (e.g., CDRs, or variable regions) of the antibody produced by clone 124-152, 2A11, or 1G10.

In addition, the invention features a method for making a hybridoma that expresses an antibody that specifically binds to an exotoxin of *C. difficile* by immunizing a transgenic non-human animal having a genome that includes a human heavy chain transgene and a human light chain transgene, with a composition that includes the exotoxin, wherein the toxin is inactivated; isolating splenocytes from the animal; generating hybridomas from the splenocytes; and selecting a hybridoma that produces an antibody that specifically binds to the exotoxin.

Treatment of humans with human monoclonal antibodies offers several advantages. For example, the antibodies are likely to be less immunogenic in humans than non-human antibodies. The therapy is rapid; toxin inactivation can occur as soon as the antibody reaches sites of infection and directly neutralizes the disease-causing toxin(s). Human antibodies localize to appropriate sites in humans more efficiently than non-human antibodies. Furthermore, the treatment is specific for *C. difficile*, and is unlikely to disrupt normal gut flora, unlike traditional antibiotic therapies.

Other features and advantages of the invention will be apparent from the following detailed description, and from the claims.

BRIEF DESCRIPTION OF THE DRAWINGS

FIG. 1 is a table listing the amino acid sequences of the VH and VL chains encoded by mRNA sequences from each clone. Lowercase letters represent amino acids in the leader peptide. CDRs are underlined. Clone 3D8, which expresses 6 unique light chain V regions, only expressed the group I amino acid sequence.

FIG. 2A is a representation of the amino acid and nucleic acid sequences of the VL chain expressed by clone 3D8. The V-segment and J-segment genes are listed above the amino acid and nucleic acid sequences. The CDRs are overlined.

FIG. 2B is a representation of the amino acid and nucleic acid sequences of the VH chain expressed by clone 3D8. The V-segment, D-segment and J-segment genes are listed above the amino acid and nucleic acid sequences. The CDRs are overlined.

FIG. 3A is a representation of the amino acid and nucleic acid sequences of the VL chain expressed by clone 1B11. The V-segment and J-segment genes are listed above the amino acid and nucleic acid sequences. The CDRs are overlined.

FIG. 3B is a representation of the amino acid and nucleic acid sequences of the VH chain expressed by clone 1B11. The V-segment, D-segment, and J-segment genes are listed above the amino acid and nucleic acid sequences. The CDRs are overlined.

FIG. 4A is a representation of the amino acid and nucleic acid sequences of the VL chain expressed by clone 33.3H2 (referred to herein as 3H2; 33.3H2 and 3H2 are used interchangeably herein). The V-segment and J-segment genes are listed above the amino acid and nucleic acid sequences. The CDRs are overlined.

FIG. 4B is a representation of the amino acid and nucleic acid sequences of the VH chain expressed by clone 33.3H2. The V-segment and J-segment genes are listed above the amino acid and nucleic acid sequences. The CDRs are overlined.

FIGS. 6A-B are a set of graphs depicting results of in vitro neutralization assays in the presence and absence of anti-toxin A monoclonal antibodies. FIG. 6A depicts results for assays performed with IMR-90 cells. FIG. 6B depicts results for assays performed with T-84 cells.

FIG. 8A-B are schematic representations of toxin A fragments analyzed for epitope mapping studies.

FIG. 9 is a table listing the results of in vivo assays to determine mouse protection from lethal challenge with toxin A by anti-toxin A monoclonal antibodies.

FIG. 17 is a graph depicting the results of hamster relapse assays as the percentage of hamsters surviving clindamycin treatment followed by C. difficile challenge. Hamsters were immunized with a fragment of toxin B prior to clindamycin treatment. Hamsters were treated with vancomycin, vancomycin and 3D8, or received no treatment.

FIG. 18 is a graph depicting the results of hamster relapse assays as the percentage of healthy animals after clindamycin treatment followed by C. difficile challenge. Hamsters were immunized with a fragment of toxin B prior to clindamycin treatment.

FIG. 22 is a representation of the amino acid sequence of C. difficile toxin A.

FIG. 23 is a representation of the amino acid sequence of C. difficile toxin B.

FIG. 28 is a representation of the amino acid and nucleic acid sequences of the VH chain expressed by clone 124-152. The V-segment, D-segment and J-segment genes are listed above the amino acid and nucleic acid sequences. The CDRs are overlined.

FIG. 29 is a representation of the amino acid and nucleic acid sequences of the VL chain expressed by clone 124-152. The V-segment and J-segment genes are listed above the amino acid and nucleic acid sequences. The CDRs are overlined.

FIG. 30 is a representation of the amino acid and related germline sequence of the VH chain expressed by clone 124-152. The V-segment, D-segment and J-segment genes are listed above the amino acid sequences. The CDRs are overlined.

FIG. 31 is a representation of the amino acid and related germline sequences of the VL chain expressed by clone 124-152. The V-segment and J-segment genes are listed above the amino acid sequences. The CDRs are overlined.

FIG. 32 is a schematic representation of the toxin B polypeptide, indicating fragments that were analyzed for epitope mapping studies.

Like reference symbols in the various drawings indicate like elements.

DETAILED DESCRIPTION OF THE INVENTION

Figure 5:
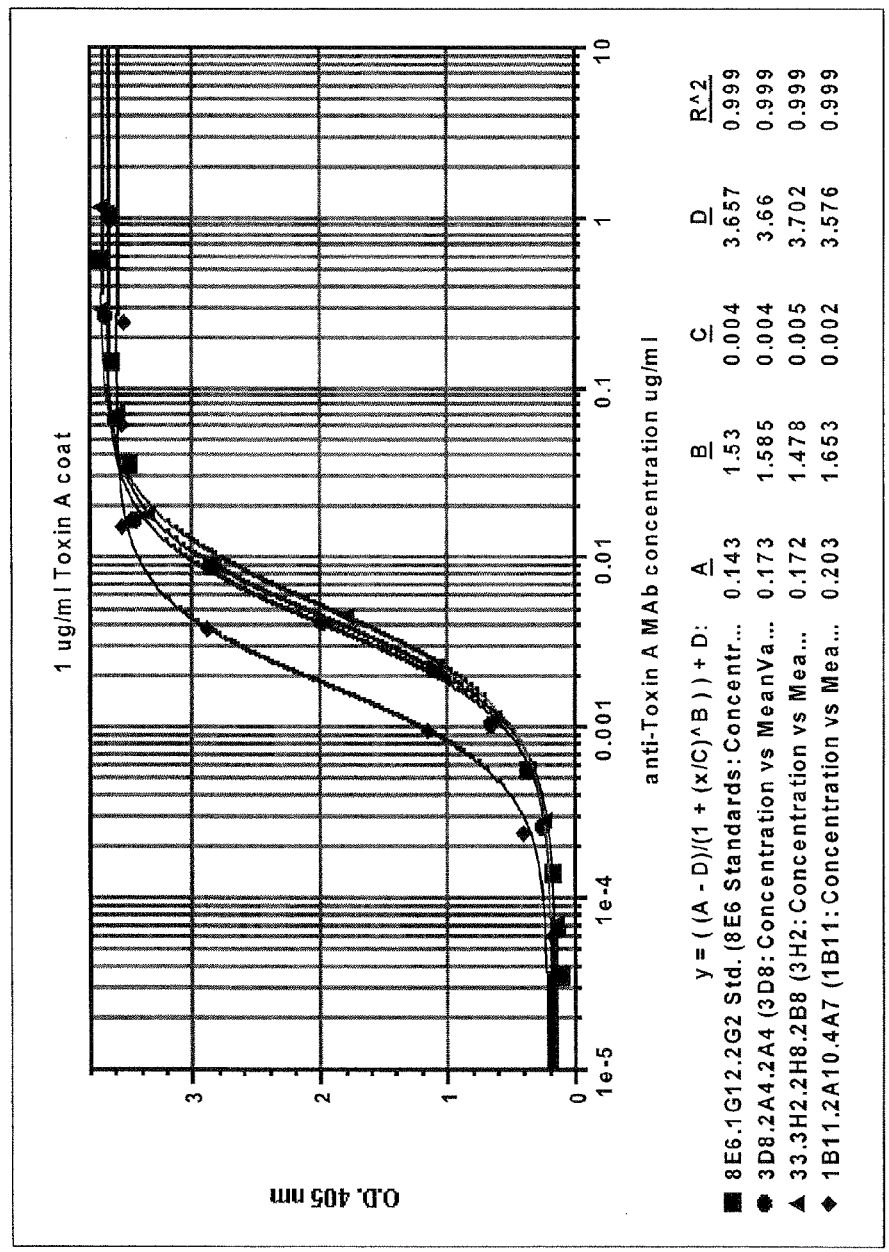
FIG. 5 is a graph depicting the results of ELISA assays, which measured binding of anti-toxin A monoclonal antibodies to toxin A.

In order to provide a clear understanding of the specification and claims, the following definitions are conveniently provided below.

DEFINITIONS

The term "toxin A" refers to the toxin A protein encoded by C. difficile. The amino acid sequence of C. difficile toxin A (SEQ ID NO:41) is provided in GenBank® under accession number A37052, version GI 98593 (see also FIG. 22). "Toxin B" refers to the toxin B protein encoded by C. difficile. The amino acid sequence of C. difficile toxin B (SEQ ID NO: 42) is provided in GenBank® under accession number 570172, version GI 7476000 (see also FIG. 23). "Protein" is used interchangeably with "polypeptide."

An "anti-C. difficile antibody" is an antibody that interacts with (e.g., binds to) a protein or other component produced by C. difficile bacteria. An "anti-toxin antibody" is an antibody that interacts with a toxin produced by C. difficile (e.g., toxin A or toxin B). An anti-toxin protein antibody may bind to an epitope, e.g., a conformational or a linear epitope, or to a fragment of the full-length toxin protein.

A "human antibody," is an antibody that has variable and constant regions derived from human germline immunoglobulin sequences. The human antibodies described herein may include amino acid residues not encoded by human germline immunoglobulin sequences (e.g., mutations introduced by random or site-specific mutagenesis in vitro or by somatic mutation in vivo).

An anti-toxin antibody, or antigen binding portion thereof, can be administered alone or in combination with a second agent. The subject can be a patient infected with C. difficile, or having a symptom of C. difficile-associated disease ("CDAD"; e.g., diarrhea, colitis, abdominal pain) or a predisposition towards *C. difficile*-associated disease (e.g., undergoing treatment with antibiotics, or having experienced *C. difficile*-associated disease and at risk for relapse of the disease). The treatment can be to cure, heal, alleviate, relieve, alter, remedy, ameliorate, palliate, improve, or affect the infection and the disease associated with the infection, the symptoms of the disease, or the predisposition toward the disease.

An amount of an anti-toxin antibody effective to treat a CDAD, or a "therapeutically effective amount," is an amount of the antibody that is effective, upon single or multiple dose administration to a subject, in inhibiting CDAD in a subject. A therapeutically effective amount of the antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion is outweighed by the therapeutically beneficial effects. The ability of an antibody to inhibit a measurable parameter can be evaluated in an animal model system predictive of efficacy in humans. For example, the ability of an anti-toxin antibody to protect mice from lethal challenge with *C. difficile* can predict efficacy in humans. Other animal models predictive of efficacy are described herein, such as the intestinal ligation model described in the Examples. Alternatively, this property of an antibody or antibody composition can be evaluated by examining the ability of the compound to modulate, such modulation in vitro by assays known to the skilled practitioner. In vitro assays include binding assays, such as ELISA, and neutralization assays.

An amount of an anti-toxin antibody effective to prevent a disorder, or a "a prophylactically effective amount," of the antibody is an amount that is effective, upon single- or multiple-dose administration to the subject, in preventing or delaying the occurrence of the onset or recurrence of CDAD, or inhibiting a symptom thereof. However, if longer time intervals of protection are desired, increased doses can be administered.

The terms "agonize," "induce," "inhibit," "potentiate," "elevate," "increase," "decrease," or the like, e.g., which denote quantitative differences between two states, refer to a difference, e.g., a statistically or clinically significant difference, between the two states.

As used herein, "specific binding" or "specifically binds to" refers to the ability of an antibody to: (1) bind to a toxin of *C. difficile* with an affinity of at least $1 \times 10^7$ M$^{-1}$, and (2) bind to a toxin of *C. difficile* with an affinity that is at least two-fold greater than its affinity for a nonspecific antigen.

An "antibody" is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. *Sequences of Proteins of Immunological Interest*, Fifth Edition, U.S. Department of Health and Human Services, NIH Publication No. 91-3242, 1991, and Chothia, C. et al., *J. Mol. Biol.* 196:901-917, 1987, which are incorporated herein by reference). Preferably, each VHC and VLC is composed of three CDRs and four FRs, arranged from amino-terminus to carboxy-terminus in the following order: FR1, CDR1, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

"Immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon, and mu constant region genes, as well as the myriad immunoglobulin variable region genes. Full-length immunoglobulin "light chains" (about 25 KD and 214 amino acids) are encoded by a variable region gene at the NH$_2$-terminus (about 110 amino acids) and a kappa or lambda constant region gene at the COOH-terminus. Full-length immunoglobulin "heavy chains" (about 50 KD and 446 amino acids), are similarly encoded by a variable region gene (about 116 amino acids) and one of the other aforementioned constant region genes, e.g., gamma (encoding about 330 amino acids). The term "immunoglobulin" includes an immunoglobulin having: CDRs from a human or non-human source. The framework of the immunoglobulin can be human, humanized, or non-human, e.g., a murine framework modified to decrease antigenicity in humans, or a synthetic framework, e.g., a consensus sequence.

As used herein, "isotype" refers to the antibody class (e.g., IgM or IgG$_1$) that is encoded by heavy chain constant region genes.

The term "antigen binding portion" of an antibody (or simply "antibody portion," or "portion"), as used herein, refers to a portion of an antibody that specifically binds to a toxin of *C. difficile* (e.g., toxin A), e.g., a molecule in which one or more immunoglobulin chains is not full length, but which specifically binds to a toxin. Examples of binding portions encompassed within the term "antigen-binding portion" of an antibody include (i) a Fab fragment, a monovalent fragment consisting of the VLC, VHC, CL and CH1 domains; (ii) a F(ab')$_2$ fragment, a bivalent fragment comprising two Fab fragments linked by a disulfide bridge at the hinge region; (iii) a Fd fragment consisting of the VHC and CH1 domains; (iv) a Fv fragment consisting of the VLC and VHC domains of a single arm of an antibody, (v) a dAb fragment (Ward et al., *Nature* 341:544-546, 1989), which consists of a VHC domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen binding portion" of an antibody. These antibody portions are obtained using conventional techniques known to those with skill in the art, and the portions are screened for utility in the same manner as are intact antibodies.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or portions thereof with a single molecular composition.

The term "recombinant" antibody, as used herein, refers to antibodies that are prepared, expressed, created, or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created, or isolated by any other means that involves splicing of human immunoglobulin gene sequences to other DNA sequences. Such recombinant antibodies include humanized, CDR grafted, chimeric, in vitro generated (e.g., by phage display) antibodies, and may optionally include constant regions derived from human germline immunoglobulin sequences.

As used herein, the term "substantially identical" (or "substantially homologous") refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the first antibody.

Calculations of "homology" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 50% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences is determined using the Needleman and Wunsch, *J. Mol. Biol.* 48:444-453, 1970, algorithm which has been incorporated into the GAP program in the GCG software package, using a Blossum 62 scoring matrix with a gap penalty of 12, a gap extend penalty of 4, and a frameshift gap penalty of 5.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. 6.3.1-6.3.6, 1989, which is incorporated herein by reference. Aqueous and nonaqueous methods are described in that reference and either can be used. Specific hybridization conditions referred to herein are as follows: 1) low stringency hybridization conditions: 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions: 6×SSC at about 45° C., followed by one or more washes in 0.2×SSC, 0.1% SDS at 60° C.; 3) high stringency hybridization conditions: 6×SSC at about 45° C., followed by one or more washes in 0.2×SSC, 0.1% SDS at 65° C.; and 4) very high stringency conditions: 0.5 M sodium phosphate, 7% SDS at 65° C., followed by one or more washes at 0.2×SSC, 1% SDS at 65° C.

It is understood that the antibodies and antigen binding portions thereof described herein may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie et al., *Science*, 247:1306-1310, 1990. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of a polypeptide, such as a binding agent, e.g., an antibody, without substantially altering a biological activity, whereas an "essential" amino acid residue results in such a change.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Overview

*C. difficile* is a gram positive, toxin-producing bacterium that causes antibiotic-associated diarrhea and colitis in humans. Provided herein are methods and compositions for treatment and prevention of *C. difficile*-associated disease (CDAD). The compositions include antibodies that recognize proteins and other molecular components (e.g., lipids, carbohydrates, nucleic acids) of *C. difficile* bacteria, including antibodies that recognize toxins produced by *C. difficile* (e.g., toxin A and toxin B). In particular, human monoclonal antibodies are provided. In certain embodiments, these human monoclonal antibodies are produced in mice expressing human immunoglobulin gene segments (described below). Combinations of anti-toxin antibodies are also provided.

The new methods include administering antibodies (and antigen-binding portions thereof) that bind to a *C. difficile* toxin to a subject to inhibit CDAD in the subject. For example, human monoclonal anti-toxin A antibodies described herein can neutralize toxin A and inhibit relapse of *C. difficile*-mediated disease. In other examples, combinations of anti-toxin A antibodies (e.g., anti-toxin A monoclonal antibodies) and anti-toxin B antibodies can be administered to inhibit primary disease and reduce the incidence of disease relapse. The human monoclonal antibodies may localize to sites of disease (e.g., the gut) in vivo.

1. Generation of Antibodies

Immunogens

In general, animals are immunized with antigens expressed by *C. difficile* to produce antibodies. For producing anti-toxin antibodies, animals are immunized with inactivated toxins, or toxoids. Toxins can be inactivated, e.g., by treatment with formaldehyde, glutaraldehyde, peroxide, or oxygen treatment (see, e.g., Relyveld et al., *Methods in Enzymology*, 93:24, 1983; Woodrow and Levine, eds., *New Generation Vaccines*, Marcel Dekker, Inc., New York, 1990). Mutant *C. difficile* toxins with reduced toxicity can be produced using recombinant methods (see, e.g., U.S. Pat. Nos. 5,085,862; 5,221,618; 5,244,657; 5,332,583; 5,358,868; and 5,433,945). For example, mutants containing deletions or point mutations in the toxin active site can be made.

Recombinant fragments of the toxins can be used as immunogens. Another approach is to inactivate the toxin by treatment with UDP-dialdehyde (Genth et al., *Inf. and Immun.*, 68(3):1094-1101, 2000). This method preserves the native structure of the toxin more readily than other treatments, and thus can elicit antibodies more reactive to the native toxin. This method is also described in Example 1, below.

Anti-toxin antibodies that bind and neutralize toxin A can interact with specific epitopes of toxin A. For example, an anti-toxin A antibody can bind an epitope in an N-terminal region of toxin A (e.g., between amino acids 1-1033 of toxin A), or a C-terminal region (e.g., between amino acids 1853-2710 of toxin A). In one example, an antibody that binds and neutralizes toxin A binds to an epitope within amino acids 1853-2710 of toxin A.

Similarly, anti-toxin B antibodies can recognize a specific epitope of toxin B, e.g., an N-terminal epitope, or a C-terminal epitope. In one example, an antibody that binds and neutralizes toxin B binds to an epitope within amino acids 1777-2366 of toxin B.

Generation of Human Monoclonal Antibodies in HuMAb Mice

Monoclonal antibodies can be produced in a manner not possible with polyclonal antibodies. Polyclonal antisera vary from animal to animal, whereas monoclonal preparations exhibit a uniform antigenic specificity. Murine animal systems are useful to generate monoclonal antibodies, and immunization protocols, techniques for isolating and fusing splenocytes, and methods and reagents for producing hybridomas are well known. Monoclonal antibodies can be produced by a variety of techniques, including conventional monoclonal antibody methodology, e.g., the standard somatic cell hybridization technique of Kohler and Milstein, *Nature*, 256: 495, 1975. See generally, Harlow, E. and Lane, D. *Antibodies: A Laboratory Manual*, Cold Spring Harbor Laboratory Press, Cold Spring Harbor, N.Y., 1988.

Although these standard techniques are known, it is desirable to use humanized or human antibodies rather than murine antibodies to treat human subjects, because humans mount an immune response to antibodies from mice and other species. The immune response to murine antibodies is called a human anti-mouse antibody or HAMA response (Schroff, R. et al., *Cancer Res.*, 45, 879-885, 1985) and is a condition that causes serum sickness in humans and results in rapid clearance of the murine antibodies from an individual's circulation. The immune response in humans has been shown to be against both the variable and the constant regions of murine immunoglobulins. Human monoclonal antibodies are safer for administration to humans than antibodies derived from other animals and human polyclonal antibodies.

One useful type of animal in which to generate human monoclonal antibodies is a transgenic mouse that expresses human immunoglobulin genes rather than its own mouse immunoglobulin genes. Such transgenic mice, e.g., "HuMAb™" mice, contain human immunoglobulin gene miniloci that encode unrearranged human heavy (μ and γ) and κ light chain immunoglobulin sequences, together with targeted mutations that inactivate the endogenous μ and κ chain loci (see e.g., Lonberg, N. et al., *Nature* 368(6474): 856-859, 1994, and U.S. Pat. No. 5,770,429). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al., supra; reviewed in Lonberg, N. *Handbook of Experimental Pharmacology* 113:49-101, 1994; Lonberg, N. and Huszar, D., *Intern. Rev. Immunol.*, 13: 65-93, 1995, and Harding, F. and Lonberg, N., *Ann. N.Y. Acad. Sci.*, 764:536-546, 1995).

The preparation of such transgenic mice is described in further detail in Taylor, L. et al., *Nucleic Acids Research*, 20:6287-6295, 1992; Chen, J. et al., *International Immunology* 5: 647-656, 1993; Tuaillon et al., *Proc. Natl. Acad. Sci.*, *USA* 90:3720-3724, 1993; Choi et al., *Nature Genetics*, 4:117-123, 1993; Chen, J. et al., *EMBO J.*, 12: 821-830, 1993; Tuaillon et al., *J. Immunol.*, 152:2912-2920, 1994; Taylor, L. et al., *International Immunology*, 6: 579-591, 1994; and Fishwild, D. et al., *Nature Biotechnology*, 14: 845-851, 1996. See further, U.S. Pat. No. 5,545,806; U.S. Pat. No. 5,569,825, U.S. Pat. No. 5,625,126, U.S. Pat. No. 5,633,425, U.S. Pat. No. 5,661,016, U.S. Pat. No. 5,770,429, U.S. Pat. No. 5,789,650, U.S. Pat. No. 5,814,318, U.S. Pat. No. 5,874,299 and U.S. Pat. No. 5,877,397, all by Lonberg and Kay, and PCT Publication Nos. WO 01/14424, WO 98/24884, WO 94/25585, WO 93/1227, and WO 92/03918.

To generate fully human monoclonal antibodies to an antigen, HuMAb mice can be immunized with an immunogen, as described by Lonberg, N. et al. *Nature*, 368(6474): 856-859, 1994; Fishwild, D. et al., *Nature Biotechnology*, 14: 845-851, 1996 and WO 98/24884. Preferably, the mice will be 6-16 weeks of age upon the first immunization. For example, a purified preparation of inactivated toxin A can be used to immunize the HuMAb mice intraperitoneally. To generate antibodies against *C. difficile* proteins, lipids, and/or carbohydrate molecules, mice can be immunized with killed or nonviable *C. difficile* organisms.

HuMAb transgenic mice respond best when initially immunized intraperitoneally (IP) with antigen in complete Freund's adjuvant, followed by IP immunizations every other week (up to a total of 6) with antigen in incomplete Freund's adjuvant. The immune response can be monitored over the course of the immunization protocol with plasma samples being obtained by retroorbital bleeds. The plasma can be screened, for example by ELISA or flow cytometry, and mice with sufficient titers of anti-toxin human immunoglobulin can be used for fusions. Mice can be boosted intravenously with antigen 3 days before sacrifice and removal of the spleen. It is expected that 2-3 fusions for each antigen may need to be performed. Several mice are typically immunized for each antigen.

The mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3x63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells are cultured in medium in which the HAT is replaced with HT. Supernatants from individual wells are then screened by ELISA for human anti-toxin cell monoclonal IgM and IgG antibodies. The antibody secreting hybridomas are replated, screened again, and if still positive for human IgG, anti-toxin monoclonal antibodies, can be subcloned at least twice by limiting dilution. The stable subclones are then cultured in vitro to generate small amounts of antibody in tissue culture medium for characterization.

In one embodiment, the transgenic animal used to generate human antibodies to the toxin contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884, the contents of which are hereby expressly incorporated by reference. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human K light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regard to human or mouse heavy chains because both endogenous mouse heavy chain gene copies are nonfunctional by virtue of the deletion spanning the $J_H$ region introduced as described in Examples 9 and 12 of WO 98/24884. Furthermore, a substantial fraction of the B cells will be monospecific with regards to the human or mouse light chains, because expression of the single copy of the rearranged human kappa light chain gene will allelically and isotypically exclude the rearrangement of the endogenous mouse kappa and lambda chain genes in a significant fraction of B-cells.

In one embodiment, the transgenic mouse will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, e.g., 0.5 to 5 mg/ml, or at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, e.g., about 40 to 80% of the spleen and lymph node B cells will express exclusively human IgG protein.

The repertoire in the transgenic mouse will ideally approximate that shown in a non-transgenic mouse, usually at least about 10% as high, preferably 25 to 50% or more as high. Generally, at least about a thousand different immunoglobulins (ideally IgG), preferably $10^4$ to $10^6$ or more, will be produced, depending primarily on the number of different V, J, and D regions introduced into the mouse genome. Typically, the immunoglobulins will exhibit an affinity for preselected antigens of at least about $10^7 M^{-1}$, $10^9 M^{-1}$, $10^{10} M^{-1}$, $10^{11} M^{-1}$, $10^{12} M^{-1}$, or greater, e.g., up to $10^{13} M^{-1}$ or greater.

HuMAb mice can produce B cells that undergo classswitching via intratransgene switch recombination (cisswitching) and express immunoglobulins reactive with the toxin. The immunoglobulins can be human sequence antibodies, wherein the heavy and light chain polypeptides are encoded by human transgene sequences, which may include sequences derived by somatic mutation and V region recombinatorial joints, as well as germline-encoded sequences. These human sequence immunoglobulins can be referred to as being substantially identical to a polypeptide sequence encoded by a human VL or VH gene segment and a human JL or JL segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments. Frequently at least 85 percent of the variable regions are encoded by human germline sequences present on the transgene. Often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) that are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

The human sequence antibodies that bind to the toxin can result from isotype switching, such that human antibodies comprising a human sequence gamma chain (such as gamma 1, gamma 2, or gamma 3) and a human sequence light chain (such as K) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human sequence antibodies have binding affinities of at least about $1\times10^9$ M$^{-1}$, typically at least $5\times10^9$ M$^{-1}$, frequently more than $1\times10^{10}$ M$^{-1}$, and sometimes $5\times10^{10}$ M$^{-1}$ to $1\times10^{11}$ M$^{-1}$ or greater.

Anti-toxin antibodies can also be raised in other mammals, including non-transgenic mice, humans, rabbits, and goats.

Anti-Toxin A Antibodies

Human monoclonal antibodies that specifically bind to toxin A include antibodies produced by the 3D8, 1B11, and 3H2 clones described herein. Antibodies with variable heavy chain and variable light chain regions that are at least 80%, or more, identical to the variable heavy and light chain regions of 3D8, 1B11, and 3H2 can also bind to toxin A. In related embodiments, anti-toxin A antibodies include, for example, the complementarity determining regions (CDR) of variable heavy chains and/or variable light chains of 3D8, 1B11, or 3H2. The CDRs of the variable heavy chain regions from these clones are shown in Table 1, below.

TABLE 1

Variable Heavy Chain CDR Amino Acid Sequences

| Clone | Chain | CDR | Amino Acid Sequence | SEQ ID NO: |
|---|---|---|---|---|
| 3D8 | H | CDR1 | NYGMH | 7 |
| 1B11 | H | CDR1 | SYGMH | 10 |
| 3H2 | H | CDR1 | KYGMH | 13 |
| 3D8 | H | CDR2 | LIWYDGSNEDYTDSVKG | 8 |
| 1B11 | H | CDR2 | VIWASGNKKYYIESVEG | 11 |
| 3H2 | H | CDR2 | VIWYDGTNKYYADSMKG | 14 |
| 3D8 | H | CDR3 | WGMVRGVIDVFDI | 9 |
| 1B11 | H | CDR3 | ANFDY | 12 |
| 3H2 | H | CDR3 | DPPTANY | 15 |

The CDRs of the variable light chain regions from these clones are shown in table 2, below.

TABLE 2

Variable Light Chain CDR Amino Acid Sequences

| Clone | Chain | CDR | Amino Acid Sequence | SEQ ID NO: |
|---|---|---|---|---|
| 3D8 | L | CDR1 | RASQGISSWLA | 16 |
| 1B11 | L | CDR1 | RASQSVSSYLA | 19 |
| 3H2 | L | CDR1 | RASQGISSWLA | 22 |
| 3D8 | L | CDR2 | AASSLQS | 17 |
| 1B11 | L | CDR2 | DASNRAT | 20 |
| 3H2 | L | CDR2 | AASSLQS | 23 |
| 3D8 | L | CDR3 | QQANSFPWT | 18 |
| 1B11 | L | CDR3 | QQRSNWSQFT | 21 |
| 3H2 | L | CDR3 | QQYKSYPVT | 24 |

CDRs are the portions of immunoglobulins that determine specificity for a particular antigen. In certain embodiments, CDRs corresponding to the CDRs in tables 1 and 2 having sequence variations (e.g., conservative substitutions) may bind to toxin A. For example, CDRs, in which 1, 2 3, 4, or 5 residues, or less than 20% of total residues in the CDR, are substituted or deleted can be present in an antibody (or antigen binding portion thereof) that binds toxin A.

Similarly, anti-toxin antibodies can have CDRs containing a consensus sequence, as sequence motifs conserved amongst multiple antibodies can be important for binding activity. For example, CDR1 of a variable light chain region of the antibodies or antigen binding portions thereof can include the amino acid sequence R-A-S-Q-X-X-S-S-X-L-A (SEQ ID NO: 25), CDR2 of a variable light chain region of the antibodies or antigen binding portions thereof can include the amino acid sequence A-S-X-X-X-S/T (SEQ ID NO:26), and/or CDR3 of a variable light chain region of the antibodies or antigen binding portions thereof can include the amino acid sequence Q-Q-X-X-S/N-X-P/S (SEQ ID NO:27), wherein X is any amino acid.

In some embodiments, CDR1 of a variable heavy chain region of the antibodies or antigen binding portions thereof includes the amino acid sequence Y-G-M-H (SEQ ID NO:28), and/or CDR2 of a variable heavy chain region of the antibodies or antigen binding portions thereof includes the amino acid sequence I-W-X-X-G-X-X-X-Y-X-X-S-X-X-G (SEQ ID NO:29), wherein X is any amino acid.

Human anti-toxin antibodies can include variable regions that are the product of, or derived from, specific human immunoglobulin genes. For example, the antibodies can include a variable heavy chain region that is the product of, or derived from a human VH3-33 gene. Numerous sequences for antibodies derived from this gene are available in GenBank® (see, e.g., Acc. No: AJ555951, GI No: 29836865; Acc. No: AJ556080, GI No.: 29837087; Acc. No.: AJ556038, GI No.: 29837012, and other human VH3-33 rearranged gene segments provided in GenBank®). The antibodies can also, or alternatively, include a light chain variable region that is the product of, or derived from a human Vκ L19 gene (see, e.g., GenBank® Acc. No. AJ556049, GI No: 29837033 for a partial sequence of a rearranged human Vκ L19 gene segment). As known in the art, and described in this section, above, variable immunoglobulin regions of recombined antibodies are derived by a process of recombination in vivo in which variability is introduced to genomic segments encoding the regions. Accordingly, variable regions derived from a human VH-33 or Vκ L19 gene can include nucleotides that are different that those in the gene found in non-lymphoid tissues. These nucleotide differences are typically concentrated in the CDRs.

Anti-Toxin B Antibodies Human monoclonal antibodies that specifically bind to toxin B include antibodies produced by the 124-152, 2A11, and 1G10 clones described herein. Antibodies with variable heavy chain and variable light chain regions that are at least 80%, or more, identical to the variable heavy and light chain regions of –152, 2A11, and 1G10 can also bind to toxin B. In related embodiments, anti-toxin B antibodies include, for example, the complementarity determining regions (CDR) of variable heavy chains and/or variable light chains of –152, 2A11, or 1G10. The CDRs of the variable heavy chain regions from these clones are shown in Table 3, below.

TABLE 3

Variable Heavy Chain CDR Amino Acid Sequences

| Clone | Chain | CDR | Amino Acid Sequence | SEQ ID NO: (a.a.) | SEQ ID NO: (n.t.) |
|---|---|---|---|---|---|
| 124-152 | H | CDR1 | SYWIG | 62 | 63 |
| 124-152 | H | CDR2 | IFYPGDSSTRYSPSFQG | 64 | 65 |
| 124-152 | H | CDR3 | RRNWGNAFDI | 66 | 67 |

The CDRs of the variable light chain regions from these clones are shown in Table 4, below.

TABLE 4

Variable Light Chain CDR Amino Acid Sequences

| Clone | Chain | CDR | Amino Acid Sequence | SEQ ID NO: (a.a.) | SEQ ID NO: (n.t.) |
|---|---|---|---|---|---|
| 124-152 | L | CDR1 | RASQSVSSSYLAW | 68 | 69 |
| 124-152 | L | CDR2 | GASSRAT | 70 | 71 |
| 124-152 | L | CDR3 | QQYGSSTWT | 72 | 73 |

CDRs are the portions of immunoglobulins that determine specificity for a particular antigen. In certain embodiments, CDRs corresponding to the CDRs in Tables 3 and 4 having sequence variations (e.g., conservative substitutions) may bind to toxin B. For example, CDRs, in which 1, 2, 3, 4, or 5 residues, or less than 20% of total residues in the CDR, are substituted or deleted can be present in an antibody (or antigen binding portion thereof) that binds toxin B.

Human anti-toxin B antibodies can include variable regions that are the product of, or derived from, specific human immunoglobulin genes (see FIGS. 28-31). For example, the antibodies can include a variable heavy chain region that is the product of, or derived from a human VH 5-51 gene. The antibodies can also, or alternatively, include a light chain variable region that is the product of, or derived from a human Vκ A27 gene and/or JK1 gene. As known in the art, and described in this section, above, variable immunoglobulin regions of recombined antibodies are derived by a process of recombination in vivo in which variability is introduced to genomic segments encoding the regions. Accordingly, variable regions derived from a human VH-5-51 or Vκ A27/JK1 gene can include nucleotides that are different that those in the gene found in non-lymphoid tissues. These nucleotide differences are typically concentrated in the CDRs.

2. Production and Modification of Antibodies

Many different forms of anti-toxin antibodies can be useful in the inhibition of CDAD. The antibodies can be of the various isotypes, including: IgG (e.g., IgG1, IgG2, IgG3, IgG4), IgM, IgA1, IgA2, IgD, or IgE. Preferably, the antibody is an IgG isotype, e.g., IgG1. The antibody molecules can be full-length (e.g., an IgG1 or IgG4 antibody) or can include only an antigen-binding fragment (e.g., a Fab, F(ab')$_2$, Fv or a single chain Fv fragment). These include monoclonal antibodies (e.g., human monoclonal antibodies), recombinant antibodies, chimeric antibodies, and humanized antibodies, as well as antigen-binding portions of the foregoing.

Anti-toxin antibodies or portions thereof useful in the present invention can also be recombinant antibodies produced by host cells transformed with DNA encoding immunoglobulin light and heavy chains of a desired antibody. Recombinant antibodies may be produced by known genetic engineering techniques. For example, recombinant antibodies can be produced by cloning a nucleotide sequence, e.g., a cDNA or genomic DNA, encoding the immunoglobulin light and heavy chains of the desired antibody. The nucleotide sequence encoding those polypeptides is then inserted into an expression vector so that both genes are operatively linked to their own transcriptional and translational expression control sequences. The expression vector and expression control sequences are chosen to be compatible with the expression host cell used. Typically, both genes are inserted into the same expression vector. Prokaryotic or eukaryotic host cells may be used.

Expression in eukaryotic host cells is preferred because such cells are more likely than prokaryotic cells to assemble and secrete a properly folded and immunologically active antibody. However, any antibody produced that is inactive due to improper folding can be renatured according to well known methods (Kim and Baldwin, *Ann. Rev. Biochem.*, 51:459-89, 1982). It is possible that the host cells will produce portions of intact antibodies, such as light chain dimers or heavy chain dimers, which also are antibody homologs according to the present invention.

The antibodies described herein also can be produced in a host cell transfectoma using, for example, a combination of recombinant DNA techniques and gene transfection methods as is well known in the art (Morrison, S., *Science,* 229:1202, 1985). For example, in one embodiment, the gene(s) of interest, e.g., human antibody genes, can be ligated into an expression vector such as a eukaryotic expression plasmid such as used in a GS gene expression system disclosed in WO 87/04462, WO 89/01036 and EP 338 841, or in other expression systems well known in the art. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes can be any method described in the art, such as electroporation, lipofectine, lipofectamine or ballistic transfection, in which cells are bombarded with microparticles carrying the DNA of interest (Rodin, et al. *Immunol. Lett.,* 74(3):197-200, 2000). After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells using standard techniques.

It will be understood that variations on the above procedures are useful in the present invention. For example, it may be desired to transform a host cell with DNA encoding either the light chain or the heavy chain (but not both) of an antibody. Recombinant DNA technology may also be used to remove some or all of the DNA encoding either or both of the light and heavy chains that is not necessary for binding, e.g., the constant region may be modified by, for example, deleting specific amino acids. The molecules expressed from such truncated DNA molecules are useful in the methods described herein. In addition, bifunctional antibodies can be produced in which one heavy and one light chain bind to a toxin, and the other heavy and light chain are specific for an antigen other than the toxin, or another epitope of the toxin.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184, 187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science*, 240:1041-1043); Liu et al. (1987) *PNAS*, 84:3439-3443; Liu et al., 1987, *J. Immunol.*, 139:3521-3526; Sun et al. (1987) *PNAS* 84:214-218; Nishimura et al., 1987, *Canc. Res.*, 47:999-1005; Wood et al. (1985) *Nature*, 314: 446-449; and Shaw et al., 1988, *J. Natl. Cancer Inst.*, 80:1553-1559). Chimeric antibodies can also be created by recombinant DNA techniques where DNA encoding murine V regions can be ligated to DNA encoding the human constant regions.

An antibody or an immunoglobulin chain can be humanized by methods known in the art. For example, once murine antibodies are obtained, variable regions can be sequenced. The location of the CDRs and framework residues can be determined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.*, 196:901-917). The light and heavy chain variable regions can, optionally, be ligated to corresponding constant regions. Indeed, it is understood that any of the antibodies described herein, including fully human antibodies, can be altered (e.g., by mutation, substitution) to contain a substitute constant region, e.g., Fc region, or portion(s) thereof to achieve, for example, a desired antibody structure, function (e.g., effector function), subtype, allotype, subclass, or the like. Anti-toxin antibodies can be sequenced using art-recognized techniques. CDR-grafted antibody molecules or immunoglobulins can be produced by CDR-grafting or CDR substitution, wherein one, two, or all CDRs of an immunoglobulin chain can be replaced. See e.g., U.S. Pat. No. 5,225,539; Jones et al., 1986, *Nature*, 321:552-525; Verhoeyan et al., 1988, *Science*, 239: 1534; Beidler et al., 1988, *J. Immunol.*, 141:4053-4060; and Winter, U.S. Pat. No. 5,225,539.

Winter describes a CDR-grafting method that may be used to prepare the antibodies of the present invention (UK Patent Application GB 2188638A, filed on Mar. 26, 1987; Winter U.S. Pat. No. 5,225,539), the contents of which is expressly incorporated by reference. For example, all of the CDRs of a particular antibody may be replaced with at least a portion of a human CDR (e.g., a CDR from clone 3D8, as shown in Tables 1 and 2, and/or clone 124-152, as shown in Tables 3 and 4, above) or only some of the CDRs may be replaced. It is only necessary to replace the number of CDRs required for binding of the antibody to a predetermined antigen (e.g., an exotoxin of *C. difficile*).

Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science*, 229:1202-1207, by Oi et al., 1986, *BioTechniques*, 4:214, and by Queen et al. U.S. Pat. No. 5,585,089, U.S. Pat. No. 5,693,761 and U.S. Pat. No. 5,693,762. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector. Other techniques for humanizing antibodies are described in Padlan et al. EP 519596 A1, published on Dec. 23, 1992.

Also within the scope of the invention are antibodies in which specific amino acids have been substituted, deleted, or added. In particular, preferred antibodies have amino acid substitutions in the framework region, such as to improve binding to the antigen. For example, a selected, small number of acceptor framework residues of the immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089 (e.g., columns 12-16), the contents of which are hereby incorporated by reference. The acceptor framework can be a mature human antibody framework sequence or a consensus sequence.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

An anti-toxin antibody, or antigen-binding portion thereof, can be derivatized or linked to another functional molecule (e.g., another peptide or protein). For example, an antibody can be functionally linked (by chemical coupling, genetic fusion, noncovalent association or otherwise) to one or more other molecular entities, such as another antibody, a detectable agent, a cytotoxic agent, a pharmaceutical agent, and/or a protein or peptide that can mediate association with another molecule (such as a streptavidin core region or a polyhistidine tag).

One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which a protein can be derivatized (or labeled) include fluorescent compounds, various enzymes, prosthetic groups, luminescent materials, bioluminescent materials, and radioactive materials. Exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, β-galactosidase, acetylcholinesterase, glucose oxidase and the like. When a protein is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A protein can also be derivatized with a prosthetic group (e.g., streptavidin/biotin and avidin/biotin). For example, an antibody can be derivatized with biotin, and detected through indirect measurement of avidin or streptavidin binding.

Labeled proteins and antibodies can be used, for example, diagnostically and/or experimentally in a number of contexts, including (i) to isolate a predetermined antigen by standard techniques, such as affinity chromatography or immunoprecipitation; and (ii) to detect a predetermined antigen (e.g., a toxin, e.g., in a cellular lysate or a patient sample) in order to monitor protein levels in tissue as part of a clinical testing procedure, e.g., to determine the efficacy of a given treatment regimen.

An anti-toxin antibody or antigen-binding fragment thereof may be conjugated to another molecular entity, such as a label.

3. Screening Methods

Anti-toxin antibodies can be characterized for binding to the toxin by a variety of known techniques. Antibodies are typically characterized by ELISA first. Briefly, microtiter plates can be coated with the toxin or toxoid antigen in PBS, and then blocked with irrelevant proteins such as bovine serum albumin (BSA) diluted in PBS. Dilutions of plasma from toxin-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the toxin. Hybridomas that produce antibodies that bind, preferably with high affinity, to the toxin can than be subcloned and further characterized. One clone from each hybridoma, which retains the reactivity of the parent cells (by ELISA), can then be chosen for making a cell bank, and for antibody purification.

To purify the anti-toxin antibodies, selected hybridomas can be grown in roller bottles, two-liter spinner-flasks or other culture systems. Supernatants can be filtered and concentrated before affinity chromatography with protein A-Sepharose (Pharmacia, Piscataway, N.J.) to purify the protein. After buffer exchange to PBS, the concentration can be determined by spectrophotometric methods.

To determine if the selected monoclonal antibodies bind to unique epitopes, each antibody can be biotinylated using commercially available reagents (Pierce, Rockford, Ill.). Biotinylated MAb binding can be detected with a streptavidin labeled probe. Anti-toxin antibodies can be further tested for reactivity with the toxin by Western blotting.

Other assays to measure activity of the anti-toxin antibodies include neutralization assays. In vitro neutralization assays can measure the ability of an antibody to inhibit a cytopathic effect on cells in culture (see Example 3, below). In vivo assays to measure toxin neutralization are described in Examples 5, 6, and 7, below.

4. Pharmaceutical Compositions and Kits

In another aspect, the present invention provides compositions, e.g., pharmaceutically acceptable compositions, which include an antibody molecule described herein or antigen binding portion thereof, formulated together with a pharmaceutically acceptable carrier.

"Pharmaceutically acceptable carriers" include any and all solvents, dispersion media, isotonic and absorption delaying agents, and the like that are physiologically compatible. The carriers can be suitable for intravenous, intramuscular, subcutaneous, parenteral, rectal, spinal, or epidermal administration (e.g., by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Useful compositions are in the form of injectable or infusible solutions. A useful mode of administration is parenteral (e.g., intravenous, subcutaneous, intraperitoneal, intramuscular). For example, the antibody or antigen binding portion thereof can be administered by intravenous infusion or injection. In another embodiment, the antibody or antigen binding portion thereof is administered by intramuscular or subcutaneous injection.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the useful methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody portions described herein can be administered by a variety of methods known in the art, and for many therapeutic applications. As will be appreciated by the skilled artisan, the route and/or mode of administration will vary depending upon the desired results.

In certain embodiments, an antibody, or antibody portion thereof may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation. Therapeutic compositions can be administered with medical devices known in the art.

Dosage regimens are adjusted to provide the optimum desired response (e.g., a therapeutic response). For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-60 mg/kg, e.g., 0.5-25 mg/kg, 1-2 mg/kg, or 0.75-10 mg/kg. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Also within the scope of the invention are kits including an anti-toxin antibody or antigen binding portion thereof. The kits can include one or more other elements including: instructions for use; other reagents, e.g., a label, a therapeutic agent, or an agent useful for chelating, or otherwise coupling, an antibody to a label or therapeutic agent, or other materials for preparing the antibody for administration; pharmaceutically acceptable carriers; and devices or other materials for administration to a subject.

Various combinations of antibodies can be packaged together. For example, a kit can include antibodies that bind to toxin A (e.g., antibodies that include the variable heavy and light chain regions of 3D8) and antibodies that bind to toxin B (e.g., human monoclonal anti-toxin B antibodies, e.g., 124-152, 2A11, and/or 1G10, or polyclonal antisera reactive with toxin B). The antibodies can be mixed together, or packaged separately within the kit.

Instructions for use can include instructions for therapeutic application including suggested dosages and/or modes of administration, e.g., in a patient with a symptom of CDAD. Other instructions can include instructions on coupling of the antibody to a chelator, a label or a therapeutic agent, or for purification of a conjugated antibody, e.g., from unreacted conjugation components.

The kit can include a detectable label, a therapeutic agent, and/or a reagent useful for chelating or otherwise coupling a label or therapeutic agent to the antibody. Coupling agents include agents such as N-hydroxysuccinimide (NHS). In such cases the kit can include one or more of a reaction vessel to carry out the reaction or a separation device, e.g., a chromatographic column, for use in separating the finished product from starting materials or reaction intermediates.

The kit can further contain at least one additional reagent, such as a diagnostic or therapeutic agent, e.g., a diagnostic or therapeutic agent as described herein, and/or one or more additional anti-toxin or anti-*C. difficile* antibodies (or portions thereof), formulated as appropriate, in one or more separate pharmaceutical preparations.

Other kits can include optimized nucleic acids encoding anti-toxin antibodies, and instructions for expression of the nucleic acids.

5. Therapeutic Methods and Compositions

The new proteins and antibodies have in vitro and in vivo therapeutic, prophylactic, and diagnostic utilities. For example, these antibodies can be administered to cells in culture, e.g., in vitro or ex vivo, or to a subject, e.g., in vivo, to treat, inhibit, prevent relapse, and/or diagnose *C. difficile* and disease associated with *C. difficile*.

As used herein, the term "subject" is intended to include human and non-human animals. The term "non-human animals" includes all vertebrates, e.g., mammals and non-mammals, such as non-human primates, chickens, mice, dogs, cats, pigs, cows, and horses.

The proteins and antibodies can be used on cells in culture, e.g., in vitro or ex vivo. For example, cells can be cultured in vitro in culture medium and the contacting step can be effected by adding the anti-toxin antibody or fragment thereof, to the culture medium. The methods can be performed on virions or cells present in a subject, as part of an in vivo (e.g., therapeutic or prophylactic) protocol. For in vivo embodiments, the contacting step is effected in a subject and includes administering an anti-toxin antibody or portion thereof to the subject under conditions effective to permit binding of the antibody, or portion, to any toxin expressed by bacteria in the subject, e.g., in the gut.

Methods of administering antibody molecules are described herein. Suitable dosages of the molecules used will depend on the age and weight of the subject and the particular drug used. The antibody molecules can be used as competitive agents for ligand binding to inhibit or reduce an undesirable interaction, e.g., to inhibit binding of toxins to the gastrointestinal epithelium.

The anti-toxin antibodies (or antigen binding portions thereof) can be administered in combination with other anti-*C. difficile* antibodies (e.g., other monoclonal antibodies, polyclonal gamma-globulin). Combinations of antibodies that can be used include an anti-toxin A antibody or antigen binding portion thereof and an anti-toxin B antibody or antigen binding portion thereof. The anti-toxin A antibody can be 3D8, an antibody that includes the variable regions of 3D8, or an antibody with variable regions at least 90% identical to the variable regions of 3D8. The anti-toxin B antibody can be 124-152, 2A11, 1G10, or an antibody with variable regions at least 90% identical to the variable regions of the foregoing, e.g., 124-152. Combinations of anti-toxin A (e.g., 3D8) and anti-toxin B antibodies (e.g., 124-152) can provide potent inhibition of CDAD.

It is understood that any of the agents of the invention, for example, anti-toxin A or anti-toxin B antibodies, or fragments thereof, can be combined, for example in different ratios or amounts, for improved therapeutic effect. Indeed, the agents of the invention can be formulated as a mixture, or chemically or genetically linked using art recognized techniques thereby resulting in covalently linked antibodies (or covalently linked antibody fragments), having both anti-toxin A and anti-toxin B binding properties. The combined formulation may be guided by a determination of one or more parameters such as the affinity, avidity, or biological efficacy of the agent alone or in combination with another agent. The agents of the invention can also be administered in combination with other agents that enhance access, half-life, or stability of the therapeutic agent in targeting, clearing, and/or sequestering *C. difficile* or an antigen thereof.

Such combination therapies are preferably additive and even synergistic in their therapeutic activity, e.g., in the inhibition, prevention (e.g., of relapse), and/or treatment of *C. difficile-related* diseases or disorders (see, e.g., Example 16 which shows the efficacy of single and combined antibody therapies). Administering such combination therapies can decrease the dosage of the therapeutic agent (e.g., antibody or antibody fragment mixture, or cross-linked or genetically fused bispecific antibody or antibody fragment) needed to achieve the desired effect.

Immunogenic compositions that contain an immunogenically effective amount of a toxin, or fragments thereof, are described herein, and can be used in generating anti-toxin antibodies. Immunogenic epitopes in a toxin sequence can be identified according to methods known in the art, and proteins, or fragments containing those epitopes can be delivered by various means, in a vaccine composition. Suitable compositions can include, for example, lipopeptides (e.g., Vitiello et al., *J. Clin. Invest.* 95:341 (1995)), peptide compositions encapsulated in poly(DL-lactide-co-glycolide) ("PLG") microspheres (see, e.g., Eldridge et al., *Molec. Immunol.* 28:287-94 (1991); Alonso et al., *Vaccine* 12:299-306 (1994); Jones et al., *Vaccine* 13:675-81 (1995)), peptide compositions contained in immune stimulating complexes (ISCOMS) (see, e.g., Takahashi et al., *Nature* 344:873-75 (1990); Hu et al., *Clin. Exp. Immunol.* 113:235-43 (1998)), and multiple antigen peptide systems (MAPs) (see, e.g., Tam, *Proc. Natl. Acad. Sci. U.S.A.* 85:5409-13 (1988); Tam, *J. Immunol. Methods* 196:17-32 (1996)).

Useful carriers that can be used with immunogenic compositions of the invention are well known, and include, for example, thyroglobulin, albumins such as human serum albumin, tetanus toxoid, polyamino acids such as poly L-lysine, poly L-glutamic acid, influenza, hepatitis B virus core protein, and the like. The compositions can contain a physiologically tolerable (i.e., acceptable) diluent such as water, or saline, typically phosphate buffered saline. The compositions and vaccines also typically include an adjuvant. Adjuvants such as incomplete Freund's adjuvant, aluminum phosphate, aluminum hydroxide, or alum are examples of materials well known in the art. Additionally, CTL responses can be primed by conjugating toxins (or fragments, inactive derivatives or analogs thereof) to lipids, such as tripalmitoyl-S-glycerylcysteinyl-seryl-serine ($P_3CSS$).

The anti-toxin antibodies can be administered in combination with other agents, such as compositions to treat CDAD. For example, therapeutics that can be administered in combination with anti-toxin antibodies include antibiotics used to treat CDAD, such as vancomycin, metronidazole, or bacitracin. The antibodies can be used in combination with probiotic agents such as *Saccharomyces boulardii*. The antibodies can also be administered in combinations with a *C. difficile* vaccine, e.g., a toxoid vaccine.

6. Other Methods

An anti-toxin antibody (e.g., monoclonal antibody) can be used to isolate toxins by standard techniques, such as affinity chromatography or immunoprecipitation. Moreover, an anti-toxin antibody can be used to detect the toxin (e.g., in a stool sample), e.g., to screen samples for the presence of *C. difficile*. Anti-toxin antibodies can be used diagnostically to monitor levels of the toxin in tissue as part of a clinical testing procedure, e.g., to, for example, determine the efficacy of a given treatment regimen.

Exemplification

Throughout the examples, the following materials and methods were used unless otherwise stated.

Materials and Methods

In general, the practice of the present invention employs, unless otherwise indicated, conventional techniques of chemistry, molecular biology, recombinant DNA technology, immunology (especially, e.g., antibody technology), and standard techniques in polypeptide preparation. See, e.g., Sambrook, Fritsch and Maniatis, Molecular Cloning Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

EXAMPLES

The invention is further described in the following examples, which do not limit the scope of the invention described in the claims.

Example 1

Generation of Anti-Toxin A Monoclonal Antibodies

*C. difficile* toxin A was obtained either from Techlab, Inc. (Blacksburg, Va.), or by recombinant production. The toxin was purified and inactivated prior to immunization. Inactivation was performed by treatment with reactive UDP-dialdehyde, which results in alkylation of catalytic residues while preserving native toxin structure. For the detailed protocol, see Genth et al., *Inf and Immun.* 68(3):1094-1101, 2000. Briefly, purified toxin A was incubated with UDP-2',3'-dialdehyde (0.1-1.0 mM) in buffer for 18 hours at 37° C., filtered through a 100 kDa-cutoff filter to remove unreacted UDP-2', 3'-dialdehyde, and washed with buffer. Inactivated toxin A (toxoid A) was used for immunization.

HCo7 transgenic mice, generated as described above in the section entitled "Generation of Human Monoclonal Antibodies in HuMAb Mice" and supplied by Medarex, Milpitas, Calif., were immunized intraperitoneally 6-12 times each with 1014 of toxoid in RIBI adjuvant. In the HCo7 transgenic mice, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. The HCo7 transgenic mice carry a human kappa light chain transgene, KCo5, as described in Fishwild et al. (1996) *Nature Biotechnology* 14:845-851, and the HCo7 human heavy chain transgene as described in U.S. Pat. Nos. 5,545,806; 5,625,825; and 5,545,807. Serum was collected from each mouse and tested for reactivity to toxin A by ELISA and neutralization of cytotoxicity on IMR-90 cells. Mice that tested positive for toxin A-reactive and neutralizing antiserum were injected with 5-10 µg toxoid A through the tail vein. Mice were sacrificed and spleens were isolated for fusion to hybridomas approximately 3 days after tail vein injection was performed.

Clonal hybridomas were generated and screened by ELISA. Percentages of kappa/gamma light chain positive, antigen-specific, and neutralizing clones identified by screening clones generated from four separate hybridoma fusions are listed in Table 5.

TABLE 5

| Fusion | % kappa/gamma positive | % antigen specific | % neutralizing |
| --- | --- | --- | --- |
| 1 | 5.7 (94/1632) | 3.4 (56/1632) | 0.7 (12/1632) |
| 2 | 0.2 (1/384) | 0 (0/384) | 0 (0/384) |
| 3 | | 1.8 (14/768) | 0.39 (3/768) |
| 4 | | 4.4 (43/960) | 1.7 (17/960) |

Three hybridoma clones were selected for further analysis: 3D8, 1B11, and 33.3H2. CDNAs from each clone were amplified by RT-PCR from mRNA, cloned, and sequenced. One heavy chain V region consensus sequence was found for each clone. All three clones utilized a VH region derived from the same germline V region gene (VH 3-33), but utilized different J sequences. The amino acid sequences of the VH and VL regions from each clone are shown in FIG. 1 (SEQ ID NOs: 1-6). The complementarity determining regions (CDRs) are overlined in the Figure.

Sequence analysis of the kappa V (Vκ light chain) genes revealed that HuMAb 1B11 and 33.3H2 each express one consensus kappa chain V sequence. The 1B11 hybridoma expressed a Vκ light chain derived from the Vκ L6 germline gene, whereas the 33.3H2 hybridoma expresses a Vκ light chain derived from the Vκ L15 germline gene. Upon analysis of the Vκ clones from HuMAb 3D8, 6 (I-VI) light chains were expressed at the mRNA level (FIG. 1). To determine which of the light chains were expressed at the protein level, mass spectroscopy and N-terminal sequencing of the purified 3D8 antibody were performed. When light chains were isolated from cellular protein and analyzed by mass spectroscopy, a single light chain was seen with a mass of 23,569 Daltons. This corresponded to the light chain with the group I amino acid sequence depicted in FIG. 1, which is derived from the Vκ L19 germline gene. N-terminal sequencing of the light chain confirmed this result. FIGS. 2A, 3A, and 4A depict the nucleotide and the amino acid sequences of the Vκ of each 3D8 (group I; SEQ ID NOs: 4, and 30-34), 1B11 (SEQ ID NO: 5), and 33.3H2 (SEQ ID NO:6) respectively. The CDRs are overlined and the germline Vκ and Jκ are shown.

Thus, the 3D8 antibody comprises a heavy chain variable region that is the product of or derived from a human VH 3-33 gene and a light chain variable region that is the product of or derived from a human Vκ L19 gene. The 1B11 antibody comprises a heavy chain variable region that is the product of or derived from a human VH 3-33 gene and a light chain variable region that this the product of or derived from a human Vκ L6 gene. The 33.3H2 antibody comprises a heavy chain variable region that is the product of or derived from a human VH 3-33 gene and a light chain variable region that this the product of or derived from a human Vκ L15 gene.

The antibodies 3D8 and 1B11 express human IgG1 constant regions, and antibody 33.3H2 expresses human IgG3 constant regions. The antibodies described in Examples 2-7 were isolated from these hybridomas, and thus express the variable sequences shown in FIG. 1 along with human constant regions. DNA encoding the antigen binding portion of each clone was cloned into a vector to be expressed as a human antibody for administration to humans.

Example 2

Binding Activity of Anti-Toxin A Antibodies

Binding of each antibody to toxin A was determined by ELISA using standard techniques. The results of this assay are depicted in FIG. 5. Antibodies produced by 3D8, 1B11, and 33.3H2 were compared to a fourth human monoclonal antibody with toxin A binding activity, 8E6. FIG. 5 shows that the antibodies bind toxin A with comparable affinities.

The affinity of the 3D8 and 1B11 antibodies for toxin A was also measured with Biacore® instrument, which detects biomolecular binding interactions with surface plasmon resonance technology. Each antibody was added to protein A-coated sensor chips, and toxin A was allowed to flow over the chip to measure binding. 3D8 had a $K_D$ of $14.6 \times 10^{-10}$M. 1B11 had a $K_D$ of $7.38 \times 10^{-10}$M. Thus, the antibodies bind with high affinity to toxin A. These binding constants indicate that the antibodies have affinities suitable for use in human therapy.

Example 3

Toxin Neutralization by Anti-Toxin A Antibodies

Antibodies expressed by 1B11, 3D8, and 33.3H2 hybridomas were tested for toxin A neutralization activity in vitro. Cells were incubated in the presence of varying concentrations of toxin A, which causes cells to round up and lose adherence to cell culture dishes. Cytopathic effect (CPE) was determined by visual inspection of cells. A CPE score from 0-4 was determined, based on the results of the visual inspection (4=100% cytotoxicity, 0=0% toxicity). The results of these assays are depicted in FIGS. 6A and 6B. Neutralization of toxicity against a human lung fibroblast cell line, IMR-90, and a human gut epithelial cell line, T-84, was determined. FIG. 6A shows that all of the antibodies had neutralizing capacity towards IMR-90 cells. The relative neutralizing activity of toxin A cytotoxicity on IMR-90 cells was 1B11>3H2>3D8. Interestingly, the relative neutralizing activity was 3D8≥1B11>3H2 against T-84 cells, which are human colonic epithelial cells (FIG. 6A). T-84 cells are believed to be more sensitive to toxin A than other cell types. T-84 cells may provide a more relevant target cell to determine toxin A cytotoxicity.

Example 4

Epitope Mapping of Anti-Toxin A Antibodies

Figure 7:
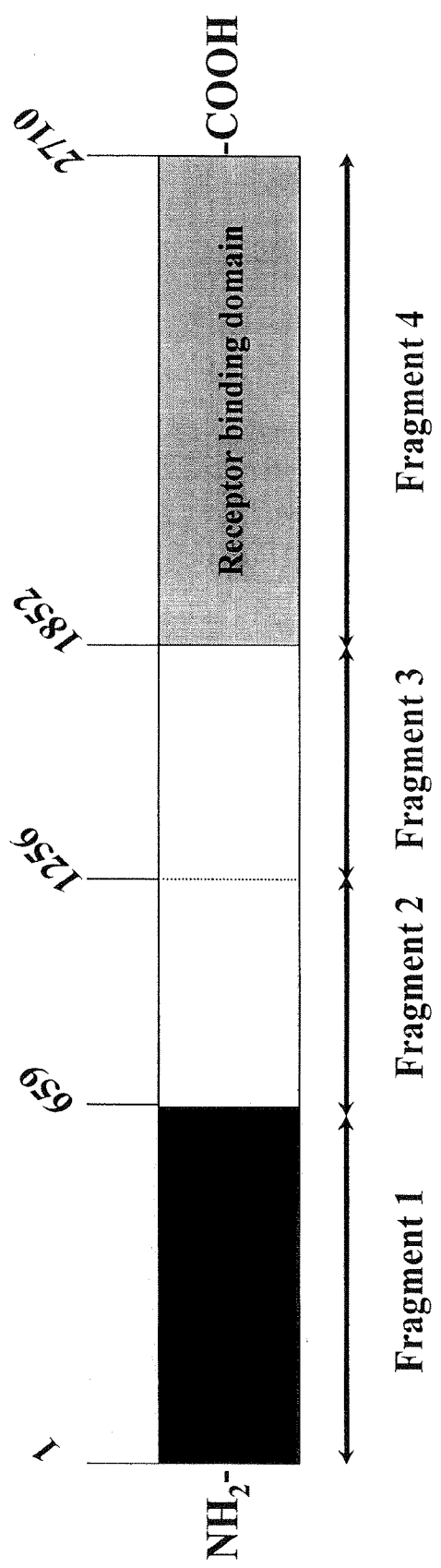
FIG. 7 is a schematic representation of the toxin A polypeptide, indicating fragments that were analyzed for epitope mapping studies.

The epitope of toxin A bound by each monoclonal antibody was determined by western blotting. Recombinant *E. coli* clones were constructed which express four fragments of toxin A representing the enzymatic domain (i.e., amino acids 1-659 of toxin A), the receptor binding domain (i.e., amino acids 1853-2710 of toxin A), and the two regions in between (i.e., amino acids 660-1255 and 1256-1852 of toxin A). The appropriate segments of the toxin A gene were PCR-amplified from genomic DNA prepared from *C. difficile* strain ATCC 43255. The fragments were cloned using a pET vector and transformed into BL21 DE3 cells for expression. The vector provides inducible expression and affinity domains for purification (i.e., a His-tag) and detection (i.e., a V5 epitope tag). Expression was induced with IPTG and fragments were purified by affinity chromatography. Binding to four different fragments of toxin A was measured: fragment 1 corresponded to amino acids 1-659; fragment 2 corresponded to amino acids 660-1255; fragment 3 corresponded to amino acids 1256-1852; and fragment 4 corresponded to amino acids 1853-2710 (FIG. 7). 1B11 reacted with fragments 1 and 2. 33.3H2 reacted with fragment 2. 3D8 and another human monoclonal antibody, 6B4, reacted with fragment 4 (the receptor binding domain). A polyclonal antiserum from rabbits immunized with toxoid A reacted with all four fragments.

The 1B11 and 33.3H2 epitopes were mapped in further detail. To map the 1B11 epitope, subfragments of fragment 1 (amino acids 1-659) corresponding to amino acids 1-540, 1-415, 1-290, and 1-165, were generated (FIG. 8A). 1B11 bound to fragment 1 and to the fragment containing amino acids 1-540. 1B11 did not bind to the other subfragments. Therefore, the epitope bound by 1B11 maps between amino acids 415-540 of toxin A.

To map the 33.3H2 epitope, subfragments of fragment 2 (amino acids 660-1255) corresponding to amino acids 660-1146, 660-1033, 660-920, and 660-807, were generated (FIG. 8B). 33.3H2 bound to the fragments corresponding to amino acids 660-1255, 660-1146, and 660-1033. 33.3H2 did not bind to the other subfragments. Therefore, the epitope bound by 33.3H2 maps between amino acids 920-1033 of toxin A.

Example 5

Protection of Mice From Lethal Toxin A Challenge by Administration of Anti-Toxin A Antibodies Each antibody was tested for the ability to protect mice from challenge with a lethal dose of toxin A. Swiss Webster female mice, each weighing 10-20 grams, were injected intraperitoneally with up to 250 µg of 3D8, 1B11, or 33.3H2, or a control antibody (anti-respiratory syncytial virus antibody, MedImmune) prior to challenge with toxin A. Approximately 24 hours after injection, mice were challenged with a dose of toxin A greater than 10 times the lethal dose ($LD_{50}$), typically 100 ng. Animals were observed for signs of toxicity for the next 7 days. The results of these experiments are summarized in FIG. 9. The data is expressed as percentage survival. Numbers in parenthesis refer to antibody dose, if a dose other than 25014 was given. FIG. 9 shows that each of the antibodies was able to protect mice from lethal toxin A challenge to some extent. The percentage of mice surviving when treated with 3D8 ranged from 10-100 percent. The percentage of mice surviving when treated with 33.3H2 ranged from 20-100 percent. The percentage of mice surviving when treated with 1B11 ranged from 0-60 percent. The relative ability of these monoclonals to protect mice was 3H2≥3D8>1B11.

Example 6

Figure 10:
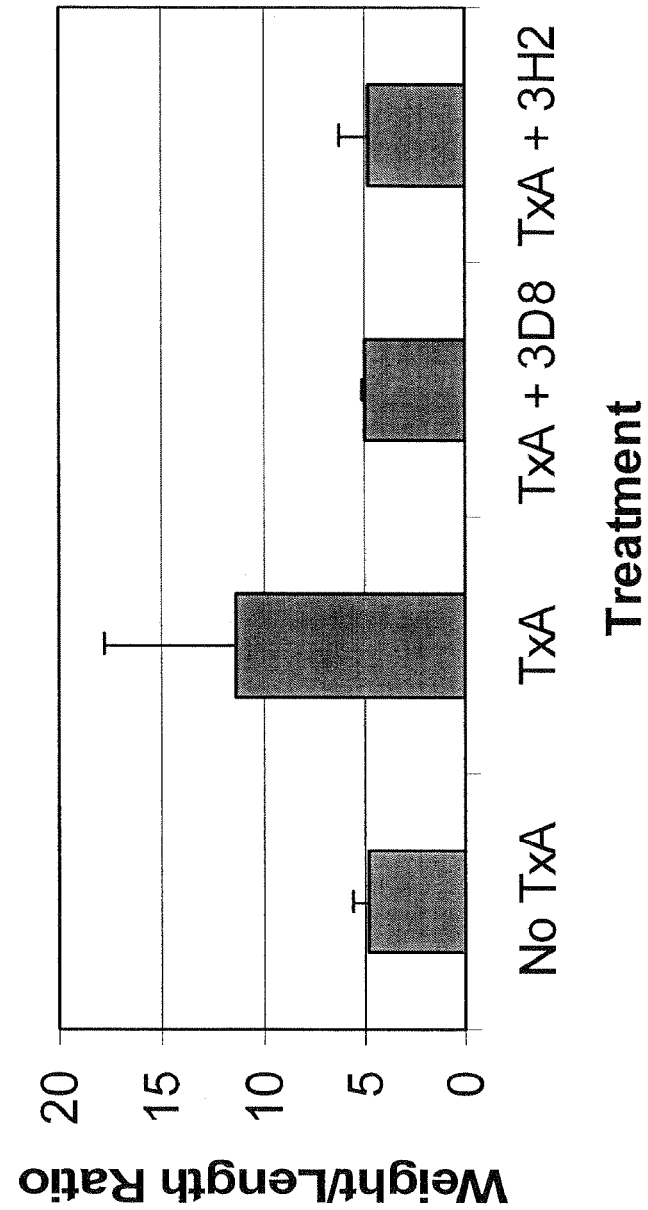
FIG. 10 is a graph depicting the results of mouse ileal loop fluid accumulation assays to measure efficacy of anti-toxin antibody neutralization in vivo.

Neutralization of Toxin A Enterotoxicity in Ligated Mouse Intestinal Loops with Anti-Toxin A Antibodies 3D8 and 33.3H2 antibodies were tested for neutralization of toxin A enterotoxicity in a mouse ileal loop model. This model measures toxin A-induced fluid accumulation in mouse intestine. To perform these experiments, each mouse was starved for 16 hours, anesthetized, and the ileum next to the cecum was exposed. A loop of 3 to 5 centimeters was doubly ligated at each end and injected with 10 µg of toxin A. The ileal loop was returned to the abdominal cavity, the wound was closed, and the animal was allowed to recover. Four hours after surgery, the animal was euthanized and the loop was removed from the animal. The length of each segment was remeasured, and the intraluminal fluid was extracted. The volume of the fluid and the volume-to-length (V:L) ratio in milliliters per centimeter was calculated for each loop. Test mice were injected with antibody parenterally 1-2 days before surgery. The results of these experiments are depicted in FIG. 10. Injection with toxin A increased the weight to length ratio of intestinal fluid by 50%. Both 3D8 and 33.3H2 prevented this increase in fluid accumulation. Mice administered either antibody had a weight to length ratio comparable to mice that did not receive any toxin A injection. Therefore, 3D8 and 33.3H2 protect from intestinal fluid accumulation in vivo.

These results indicate that the anti-toxin A monoclonal antibodies protect from toxin A-mediated enterotoxicity in vivo. The mouse ligated loop data shows that these monoclonal antibodies can protect from mucosal damage when administered systemically.

Example 7

Protection of Hamsters from *C. difficile* Relapse with Anti-Toxin A Antibodies

Figure 11A:
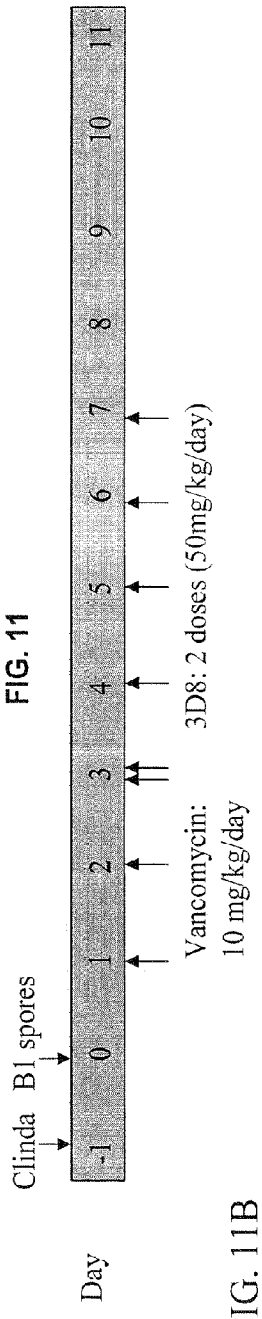
FIG. 11A is a schematic diagram of the timeline of administration of various agents to hamsters in a hamster relapse model.

3D8 was tested in a hamster relapse model. Hamsters are sensitive to the toxic effects of *C. difficile* toxins, and typically die within 2-3 days of receiving a single dose of clindamycin in the presence of *C. difficile*. To test the efficacy of 3D8 in hamsters, a relapse model was used. In this model, hamsters were given a dose of clindamycin and a dose of *C. difficile* B1 spores one day later. One set of control hamsters received no additional antibiotic or antibody. A second set of control hamsters were treated with 10 mg/kg/day vancomycin. Vancomycin is an antibiotic used in the treatment of *C. difficile* disease. As shown in FIG. 11A, a test set of hamsters received 10 mg/kg/day vancomycin and 2 mg/kg/day of a rabbit polyclonal antiserum raised against toxin A each day for seven days after *C. difficile* exposure, as indicated by the arrows in the figure. A second test set of hamsters received 10 mg/kg/day vancomycin and 50 mg/kg/day 3D8 at the same time intervals. Hamster survival was plotted versus time and is shown in FIG. 11B.

Figure 11B:
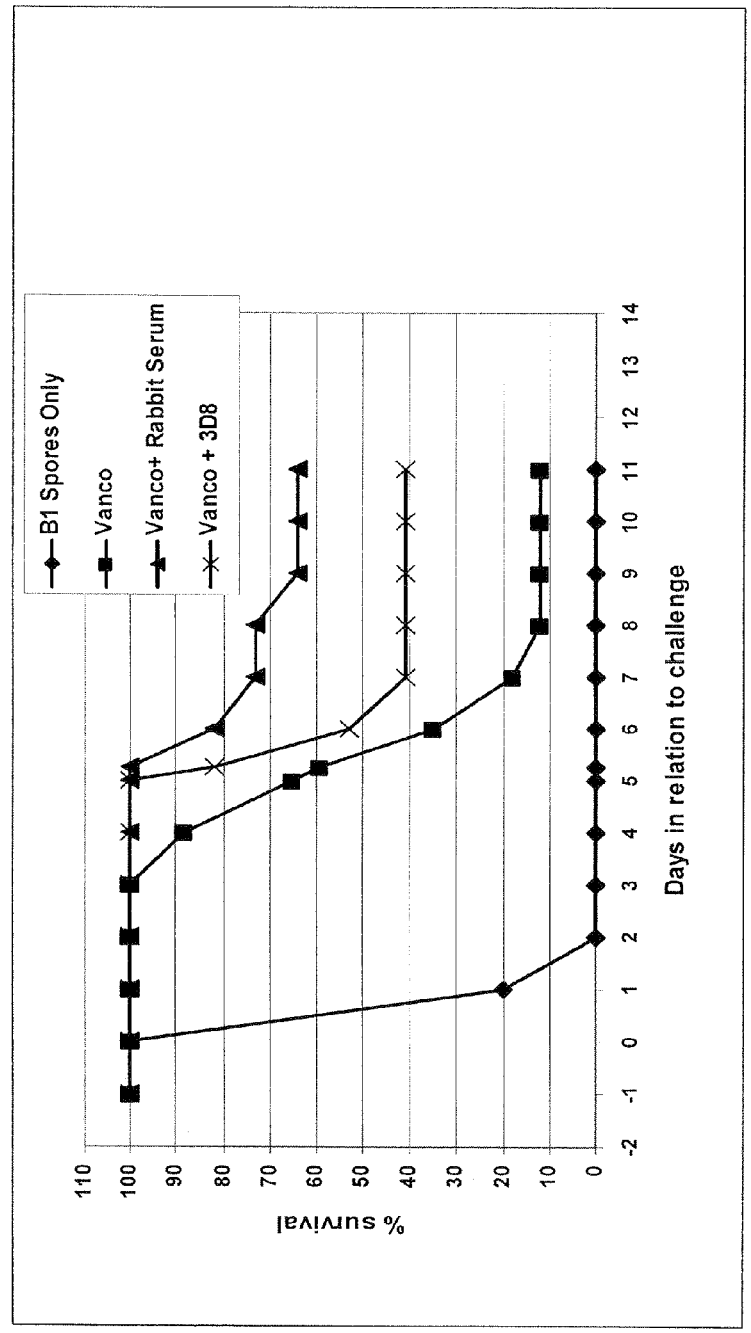
FIG. 11B is a graph depicting the results of the assays as the percentage of hamsters surviving clindamycin treatment followed by C. difficile challenge.
Figure 12:
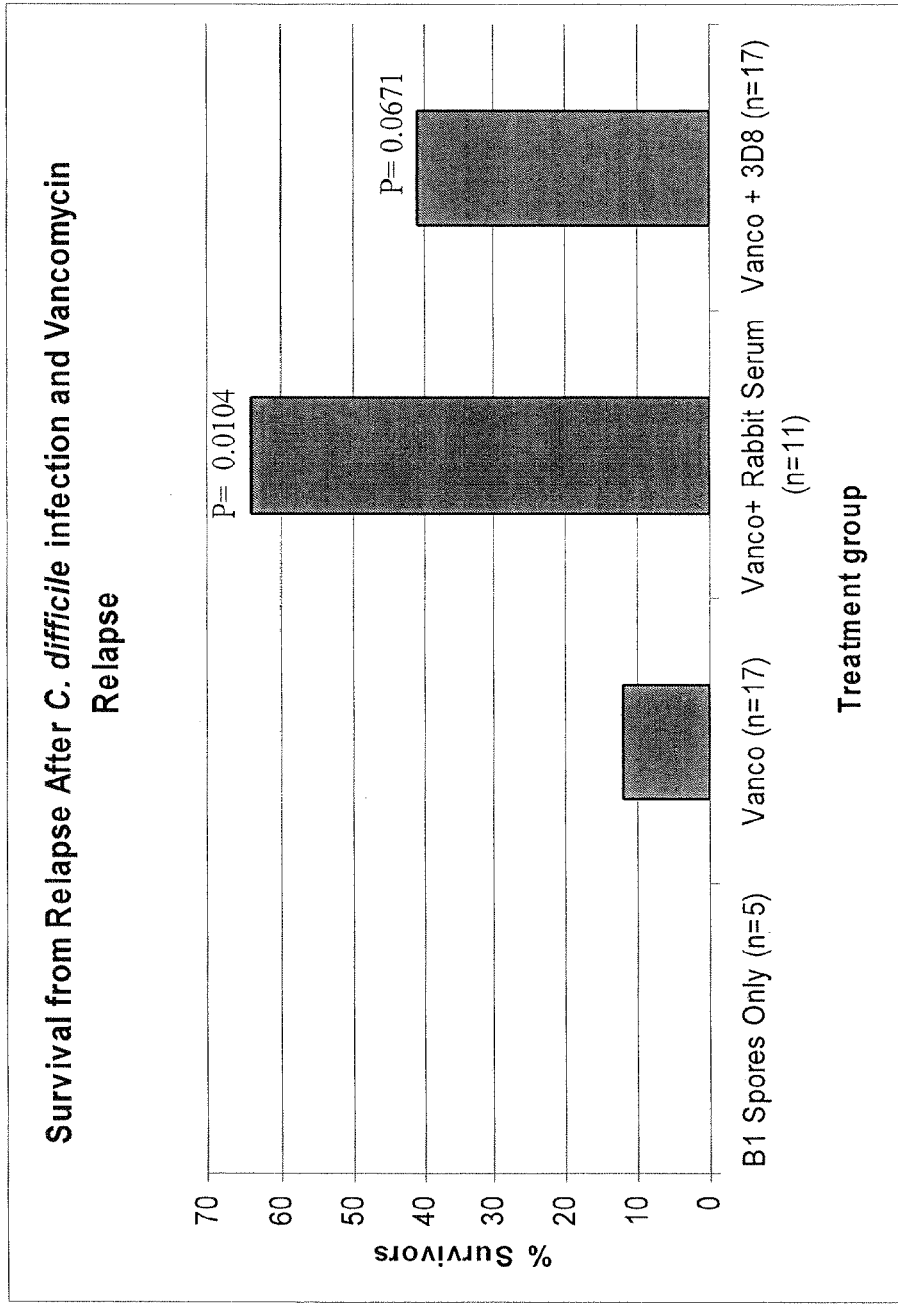
FIG. 12 is a graph depicting results of hamster relapse assays as the percentage of hamsters surviving clindamycin treatment followed by C. difficile challenge.

FIG. 11B shows that all of the hamsters that received only clindamycin and *C. difficile* (diamonds) died within two days of challenge with the bacteria. Twelve percent (2/17) of hamsters treated with vancomycin (squares) survived challenge with bacteria; eighty-eight percent (15/17) died within eight days. Forty-one percent (7/17) of hamsters treated with vancomycin and 3D8 (crosses) survived challenge; fifty-nine (10/17) percent died within seven days. Sixty-four percent (7/11) of hamsters treated with vancomycin and polyclonal rabbit serum (triangles) survived the challenge with bacteria; thirty-six percent (4/11) died within nine days. These data are also depicted in FIG. 12 as the percentage of total survivors in each treatment group. As shown in the figure, the percentage of survivors was highest (sixty-four percent) in the group receiving vancomycin and polyclonal rabbit serum. The group receiving 3D8 and vancomycin had the second highest rate of survival (forty-one percent). Only twelve percent of vancomycin-treated hamsters survived. Those with no treatment all died. These data show that polyclonal and monoclonal anti-toxin antibodies protect from relapse of *C. difficile* disease in vivo when administered after infection.

Example 8

Production of Anti-Toxin A Antibodies for Administration in Humans

Nucleic acid sequences encoding the variable heavy chain and light chains of the 3D8 antibody were cloned into a pIE-Ugamma1F vector using standard recombinant DNA methodology. The vector was amplified in *E. coli*, purified, and transfected into CHO-dg44 cells. Transfected cells were plated at $4\times10^5$ cells per well in a 96-well dish and selected for vector transfection with G418. One clone, designated 1D3, was originally selected by G418 resistance, then assayed along with other transfectomas for production of IgG. 1D3 had a higher level of IgG production relative to other transfectants during several rounds of expansion. The expression of the 3D8 antibody was amplified by growth in the presence of increasing concentrations of methotrexate. A culture capable of growth in 175 nM methotrexate was chosen for cloning single cells for further development. Plating the culture in 96 well plates at low density allowed generation of cultures arising from a single cell or clones. The cultures were screened for production of human IgG, and the cell that produced the highest level of IgG was selected for further use. The methotrexate-amplified clone was expanded to produce a cell bank including multiple frozen vials of cells.

To prepare antibodies from transfected cells, cells from a clone isolated in the previous steps are cultured and expanded as inoculum for a bioreactor. The bioreactor typically holds a 500 liter volume of culture medium. The cells are cultured in the bioreactor until cell viability drops, which indicates a maximal antibody concentration has been produced in the culture. The cells are removed by filtration. The filtrate is applied to a protein A column. Antibodies bind to the column, and are eluted with a low pH wash. Next, the antibodies are applied to a Q-Sepharose column to remove residual contaminants, such as CHO cell proteins, DNA, and other contaminants (e.g., viral contaminants, if present). Antibodies are eluted from the Q-Sepharose column, nano-filtered, concentrated, and washed in a buffer such as PBS. The preparation is then aseptically aliquoted into vials for administration.

Example 9

Preparation and Characterization of Polyclonal Anti-Toxin B Antibodies

Two Nubian goats (#330 and #331) were injected intramuscularly with 50 μg UDP dialdehyde-inactivated toxin B (Techlab) and complete Freund's adjuvant. Booster doses of 25 μg toxoid B with Freund's incomplete adjuvant were given intramuscularly at two-week intervals. Test bleeds were obtained after 4 immunizations. ELISA reactivity and neutralization of cytotoxicity against both toxin A and toxin B were assayed to measure the specificity and cross reactivity of the sera.

Figure 13:
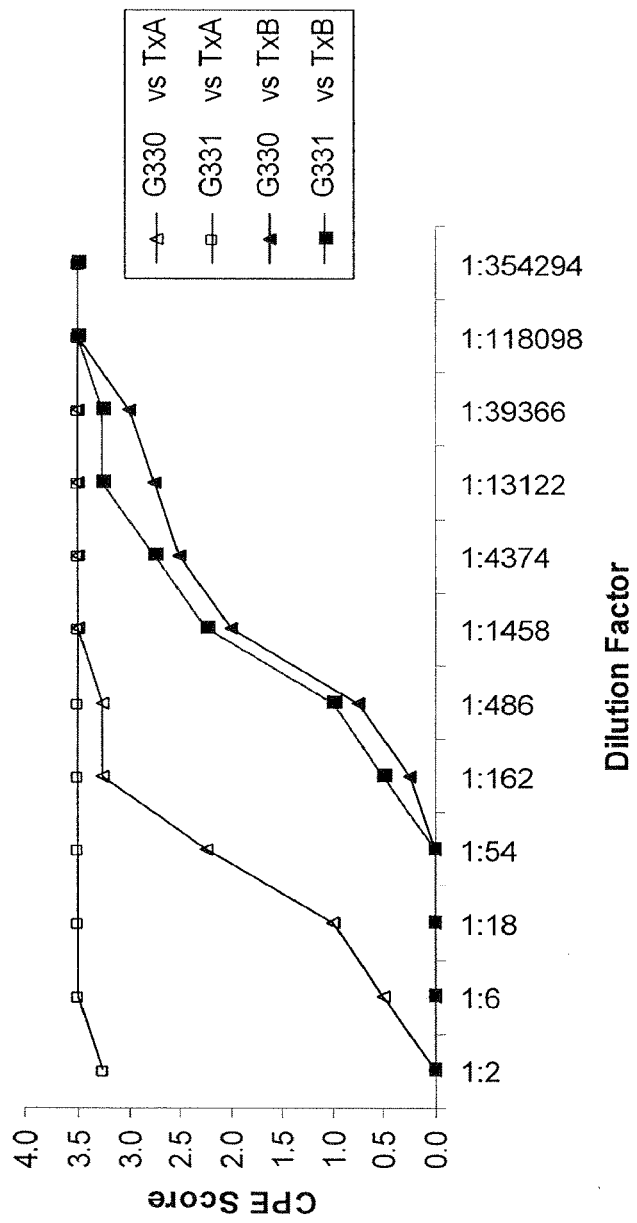
FIG. 13 is a graph depicting results of assays in which in vitro neutralization of toxin A and toxin B was measured in the presence and absence of polyclonal antisera from goats immunized with toxoid B. "G330" refers to samples in which sera from goat #330 were tested. "G331" refers to samples in which sera from goat #331 were tested.

Both animals responded well to toxin B and to a lesser extent to toxin A as measured by ELISA. Sera from goat #331 had less toxin A cross-reactivity and was chosen for the majority of the subsequent experiments. Neutralization of cytotoxicity to IMR-90 cells was determined as described in Example 3. The results of cytotoxicity neutralization are depicted in FIG. 13, which shows that sera from both animals exhibited good toxin B neutralizing antibody titers and very low, but detectable, toxin A neutralizing antibody titers. The ability of the goat sera to protect mice from a lethal intraperitoneal challenge with toxin B (100 ng) was also confirmed (data not shown).

Example 10

Figure 14:
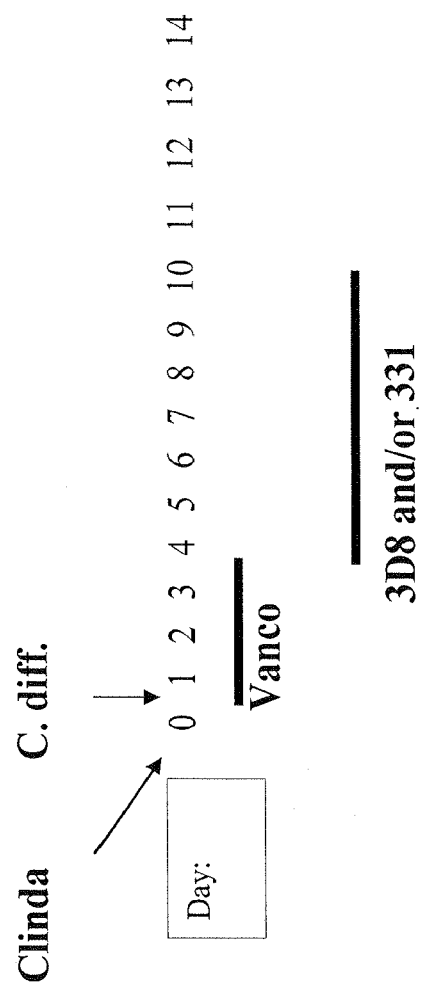
FIG. 14 is a schematic diagram of the timeline of administration of various agents to hamsters in a hamster relapse model.
Figure 15:
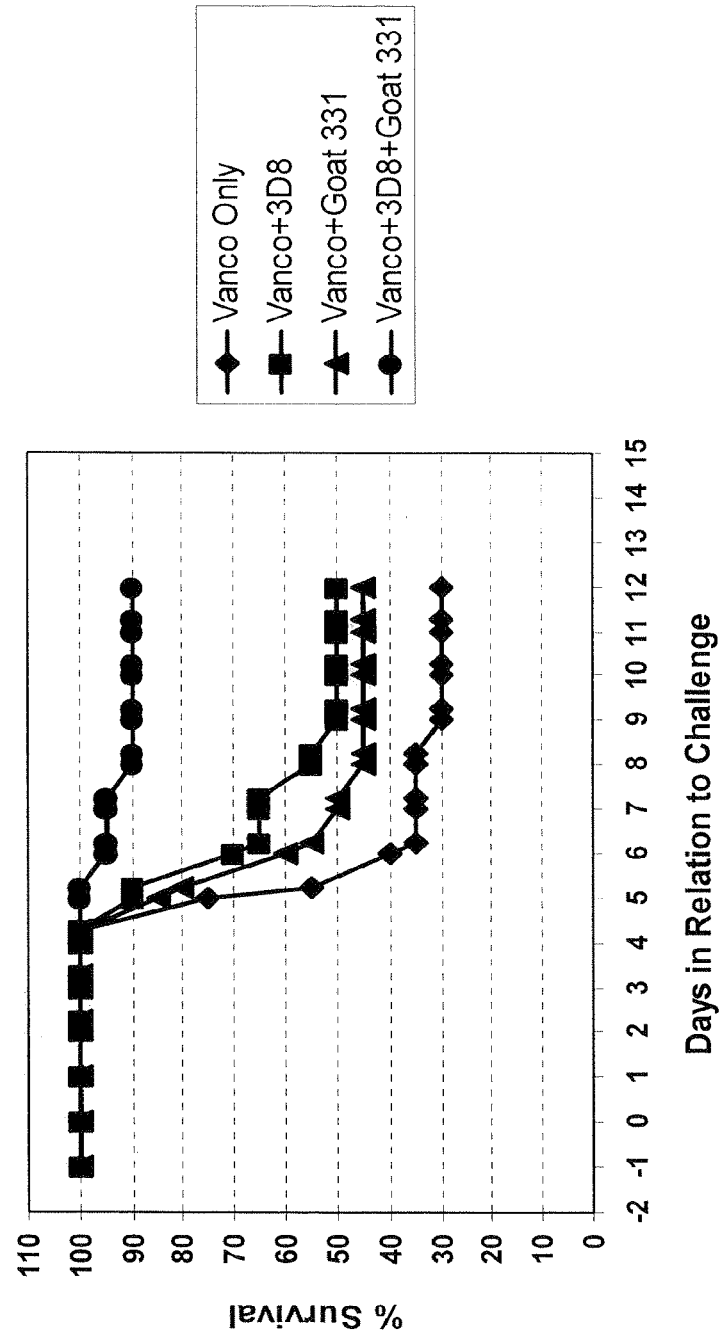
FIG. 15 is a graph depicting the results of hamster relapse assays as the percentage of hamsters surviving clindamycin treatment followed by C. difficile challenge. Hamsters were treated with vancomycin, vancomycin and 3D8, vancomycin and antisera from goat #331, or vancomycin, 3D8, and antisera from goat #331.
Figure 16:
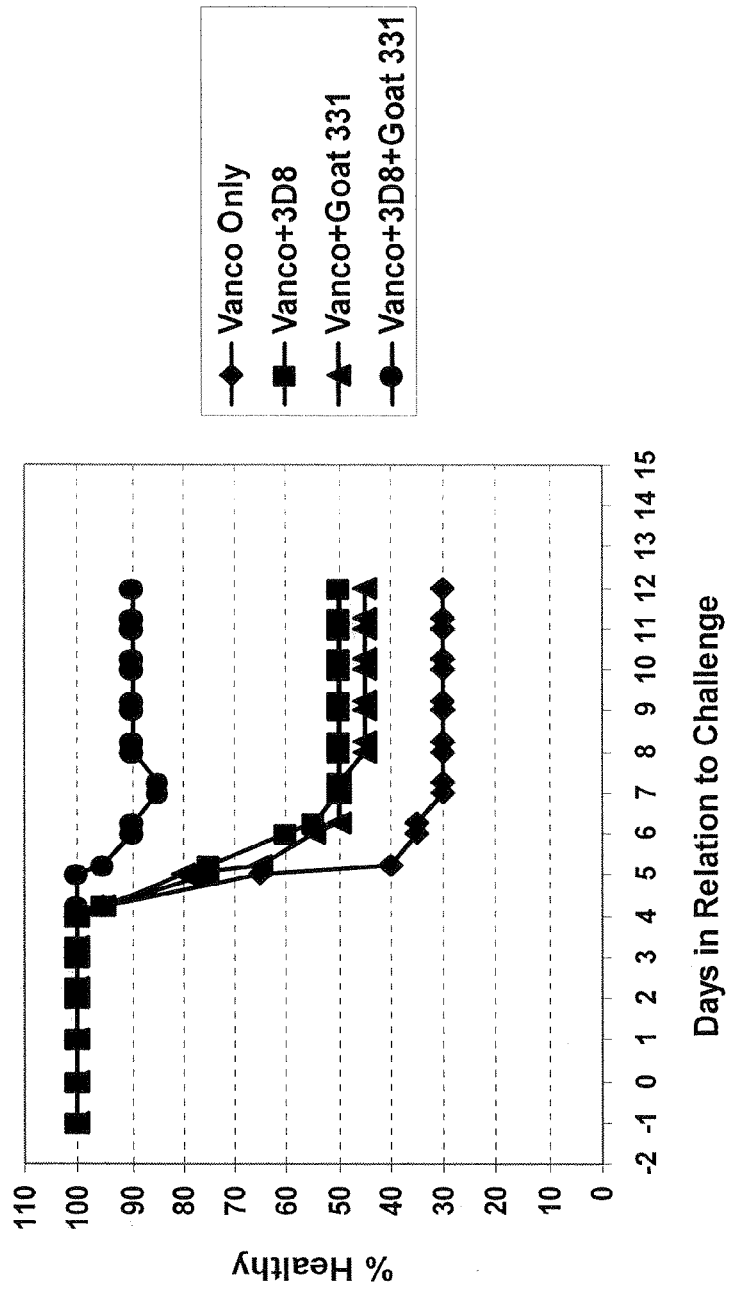
FIG. 16 is a graph depicting the results of hamster relapse assays as the percentage of healthy animals after clindamycin treatment followed by C. difficile challenge. "Goat 331" refers to antisera from goat #331.

Protection of Hamsters From *C. difficile* Relapse with Anti-Toxin A and Anti-Toxin B Antibodies Groups of hamsters (n=20) were challenged with clindamycin and *C. difficile*, and then treated with vancomycin as described in the hamster model of relapse in Example 7. Antibodies (either 3D8, serum from goat #331, or 3D8 and serum from goat #331) were given twice daily after vancomycin treatment (FIG. 14). Animals were monitored for survival (FIG. 15) or illness (FIG. 16). Antibody doses were 1 ml twice daily for serum from goat #331 and 3 mg for 3D8 given twice daily. Animals receiving vancomycin only (i.e., no antibody treatment) served as a negative controls. As observed previously, 3D8 and vancomycin treatment alone demonstrated a partial protective effect, in which 10 out of 20 animals were protected from lethality (FIG. 15). Fifty percent of animals in this group remained healthy (FIG. 16). Six out of 20 animals receiving vancomycin treatment alone were protected (FIG. 15). Thirty percent remained healthy (FIG. 16). Partial protection (9/20 animals protected) was also observed when the goat serum was used alone (FIG. 15). Forty percent remained healthy. Protection was increased to nearly 100% when both goat serum and 3D8 were given together (18/20) and disease onset was delayed (FIG. 15). Ninety percent of these animals remained healthy (FIG. 16). Clearly, protection from illness followed a pattern similar to protection from lethality. These data demonstrate that 3D8 can be fully protective in the hamster disease model when toxin B is also neutralized.

Example 11

Protection of Hamsters From *C. difficile* Relapse in Hamsters Immunized with Toxin B Hamsters were immunized intraperitoneally with 10 μg of the COOH-terminal fragment of toxin B (corresponding to amino acids 1777-2366 of toxin B) expressed in *E. coli* and using RIBI as adjuvant. Animals received 7 doses of toxin B antigen. Neutralizing antibody responses were observed in the animals that were tested. Groups of immunized hamsters were challenged with clindamycin and *C. difficile* then treated with vancomycin as described in the hamster model of relapse in Example 7. Antibody (3D8, 3 mg/dose) was given twice daily after vancomycin treatment to 19 animals and compared to a negative control group (n=20) that received no treatment (FIGS. 17 and 18). Six animals were challenged without vancomycin treatment to ensure that hamsters immunized with toxin B antigen were susceptible to *C. difficile* infection. Animals were monitored for survival (FIG. 17) or illness (FIG. 18). FIG. 17 shows that immunized animals that were not given 3D8 relapsed at a similar rate to that observed previously (65% relapse). Toxin B-immunized animals receiving 3D8 were more fully protected from relapse than observed previously (10% relapse, as compared to approximately 50% relapse in animals not previously immunized with toxin B in other experiments).

FIG. 18 shows that some of the immunized animals receiving 3D8 became ill but recovered from their diarrhea. Thirty five percent of immunized animals receiving vancomycin alone remained healthy. In experiments in which toxin B reactive sera were not present in animals, virtually all animals that had diarrhea later died. These data provide further evidence that 3D8 can be fully protective in the hamster disease model when toxin B is also neutralized. Neutralization of toxin B in addition to toxin A was required for optimal protection from *C. difficile* disease in this model.

Example 12

Figure 19:
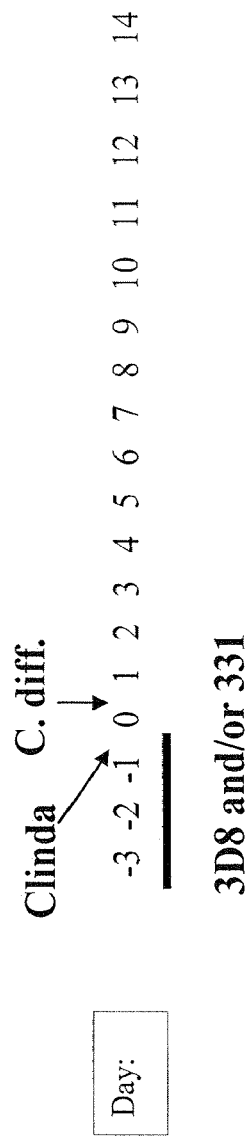
FIG. 19 is a schematic diagram of the timeline of administration of various agents to hamsters in a C. difficile direct challenge model. "331" refers to antisera from goat #331. "Clinda" refers to treatment with clindamycin.
Figure 20:
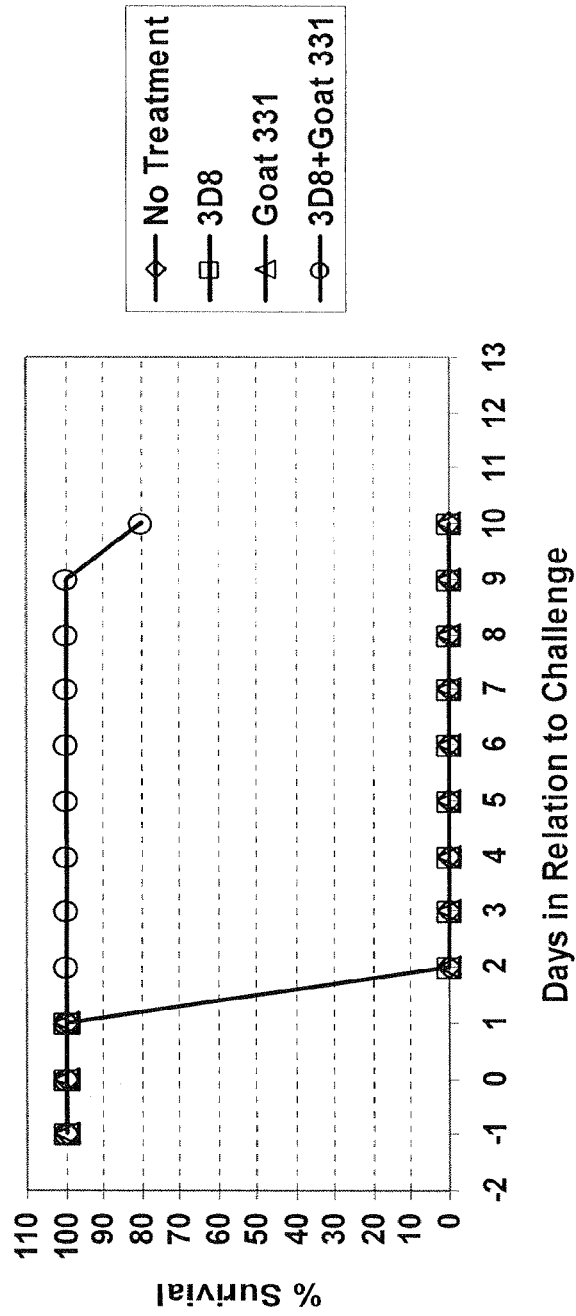
FIG. 20 is a graph depicting the results of direct challenge assays as the percentage of hamsters surviving direct C. difficile challenge.
Figure 21:
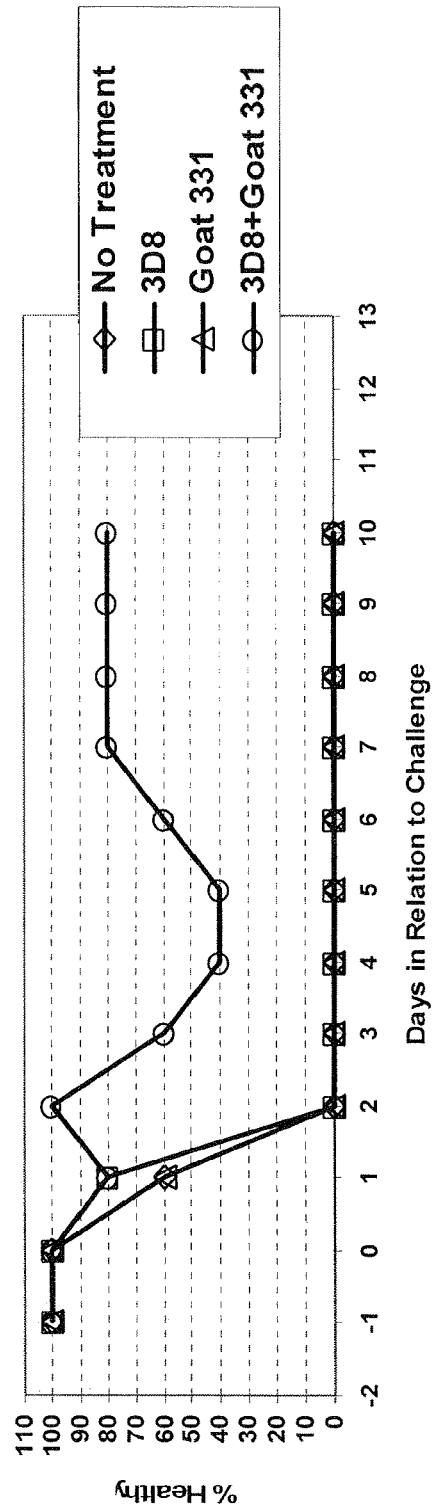
FIG. 21 is a graph depicting the results of direct challenge assays as the percentage of healthy animals after direct challenge with C. difficile.

Protection of Hamsters from Primary *C. difficile* Challenge Using 3D8 in Hamsters Treated with Goat Anti-Toxin B Sera Prevention of relapse of *C. difficile* disease in the hamsters was easier to demonstrate than protection from direct challenge (i.e., challenge without vancomycin administration). Experiments with rabbit sera demonstrated only weak protection from direct challenge and 3D8 had no detectable affect on direct challenge. Since 3D8 was more protective in a background of toxin B neutralizing antibodies, it was determined whether the combined administration of 3D8 and anti-toxin B antisera could prevent disease due to direct challenge. Groups of 5 hamsters were challenged after receiving once daily doses of 3D8 (3 mg), combined 3D8 (3 mg) and goat #331 (1 ml) sera, or no antibodies for the 3 days prior to challenge as depicted in FIG. 19. The data in FIG. 20 shows that animals receiving no antibodies or either 3D8 or goat sera alone all died with 48 hours of *C. difficile* challenge. Most animals (80%) receiving both 3D8 and goat sera survived and the affected animals survived for 10 days after challenge. FIG. 21 shows that animals treated with 3D8 and goat sera became ill but recovered. These data provide further evidence that 3D8 can be fully protective in the hamster disease model when toxin B is also neutralized. Neutralization of toxin B in addition to toxin A was required for optimal protection from *C. difficile* disease in this model.

The successful protection of hamsters directly challenged with *C. difficile* offers several advantages to the screening of new toxin B candidates. Smaller numbers of animals can be used since 100% of untreated animals die. Antibodies, such as monoclonal antibodies (e.g., human monoclonal antibodies) can be screened directly in hamsters because the procedure requires 100 mg or less of the test antibody. Other modes of testing, such as the relapse model, require the effort of producing gram quantities due to the low attack rate in the relapse model, which necessitates testing larger numbers of animals. Direct challenge experiments are also shorter in duration with a definitive read out within 3-4 days of *C. difficile* challenge compared to 7-10 in the relapse model. In addition, the elimination of vancomycin treatment from the screening method reduces the number of times animals are handled.

Example 13

Generation of Anti-Toxin B Monoclonal Antibodies

*C. difficile* toxin B was obtained either from Techlab, Inc. (Blacksburg, Va.), or by recombinant production. The toxin was purified and inactivated prior to immunization. Inactivation was performed by treatment with reactive UDP-dialdehyde, which results in alkylation of catalytic residues while preserving native toxin structure. Briefly, purified toxin B was incubated with UDP-2',3'-dialdehyde (0.1-1.0 mM) in buffer for 18 hours at 37° C., filtered through a 100 kDa-cutoff filter to remove unreacted UDP-2',3'-dialdehyde, and washed with buffer. Inactivated toxin B (toxoid B) or recombinant toxin B fragments were used as immunogens. A toxin B receptor binding domain (amino acid residues 1777-2366) was expressed in *E. coli* as a fusion protein containing an immunotag (hexahistadine) for affinity purification using nickel chelate affinity chromatography (designated fragment 4; see Example 11).

Hco12 transgenic mice, generated as described above in the section entitled "Generation of Human Monoclonal Antibodies in HuMAb Mice" and supplied by Medarex, Milpitas, Calif., were immunized intraperitoneally 6-12 times each with 10 µg of toxoid in RIBI adjuvant. In the Hco12 transgenic mice, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. The Hco12 transgenic mice carry a human kappa light chain transgene, KCo5, as described in Fishwild et al. (1996) *Nature Biotechnology* 14:845-851, and the Hco12 human heavy chain transgene as described in U.S. Pat. Nos. 5,545, 806; 5,625,825; and 5,545,807. Serum was collected from each mouse and tested for reactivity to toxin B by ELISA and neutralization of cytotoxicity on IMR-90 cells. Mice that tested positive for toxin B-reactive and neutralizing antiserum were injected with 5-10 µg toxoid B or fragment 4 through the tail vein. Mice were sacrificed and spleens were isolated for fusion to hybridomas approximately 3 days after tail vein injection was performed.

Figure 27:
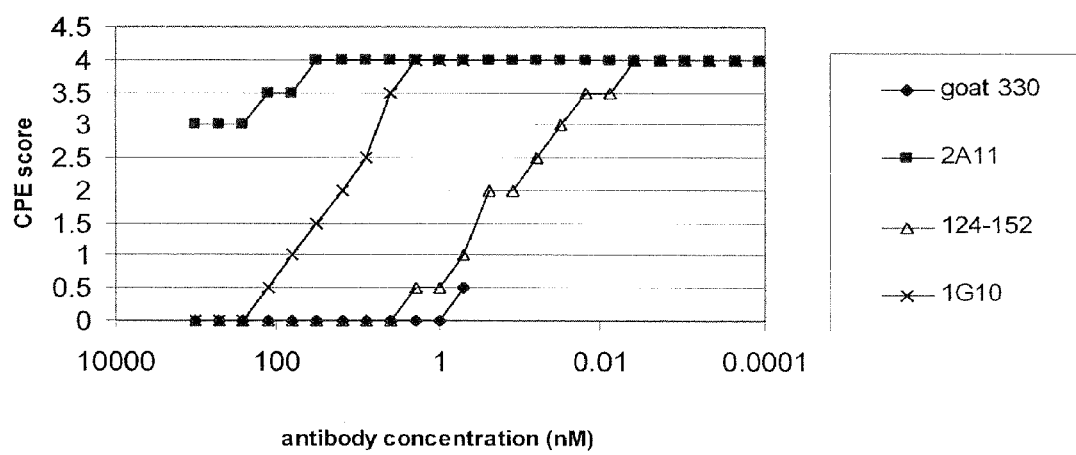
FIG. 27 is a graph depicting results of assays in which in vitro neutralization of toxin A and toxin B was measured in the presence of monoclonal antibodies to toxin B or goat polyclonal sera against toxin B.

Clonal hybridomas were generated and screened by ELISA. Three hybridoma clones were selected for further analysis: 124-152; 2A11; and 1G10. In particular, cDNAs from the 124-152 clone were amplified by RT-PCR from mRNA, cloned, and sequenced. The heavy chain V region was determined to be derived from the germline sequence VH 5-51, the D region derived from the germline sequence 7-27, and the J sequence from the germline region JH3b. The light chain (kappa) regions were determined to be derived from A27 and the J region from JK1. The isotype of the 124-152 clone was determined to be IgG1. The amino acid sequences of the VH and VL regions of the 124-152 clone are shown in FIGS. 27-28. The complementarity determining regions (CDRs) are indicated in the Figures. The related germline sequences of the VH and VL regions are shown in FIGS. 30-31.

The antibodies 124-152; 2A11; and 1G10 were isolated from corresponding hybridomas and tested for their binding characteristics (infra). DNA encoding the 124-152 clone was cloned into a vector to be expressed as a human antibody for administration to humans.

Example 14

Binding Activity of Anti-Toxin B Antibodies

Binding of each antibody to toxin B was determined by Biacore using standard techniques. The results of this assay are depicted in Table 6. Antibodies produced by 124-152; 2A11; and 1G10 were compared to appropriate controls.

In particular, the affinity of the 124-152; 2A11; and 1G10 antibodies for toxin B was measured with Biacore® instrument, which detects biomolecular binding interactions with surface plasmon resonance technology. Each antibody was added to protein A-coated sensor chips, and toxin B was allowed to flow over the chip to measure binding. 124-152 had a $K_D$ of $1.64 \times 10^{-10}$M; 2A11 had a $K_D$ of $0.24 \times 10^{-10}$M; and 1G10 had a $K_D$ of $2.98 \times 10^{-10}$M. Thus, the antibodies bind with high affinity to toxin B. These binding constants indicate that the antibodies have affinities suitable for use in vivo application, for example, human therapy.

TABLE 6

| Sample ID | $K_D \times 10^{-10}$ (M) | $k_a \times 10^5$ (1/Ms) | $k_d \times 10^{-5}$ (1/s) |
| --- | --- | --- | --- |
| 2A11 | 0.24 | 21 | 5.07 |
| 124.152 | 1.64 | 34.5 | 56.4 |
| 51.1G10 | 2.98 | 1.31 | 3.89 |

Example 15

Toxin Neutralization by Anti-Toxin B Antibodies

Antibodies expressed by 124-152; 2A11; and 1G10 hybridomas were tested for toxin B neutralization activity in vitro. Cells were incubated in the presence of varying concentrations of a monoclonal antibody specific to toxin B which would prevent cells from rounding up after exposure to toxin B. Cytopathic effect (CPE) was determined by visual inspection of cells. A CPE score from 0-4 was determined, based on the results of the visual inspection (4=100% cytotoxicity, 0=0% toxicity). The results of these assays are depicted in FIG. 27. Neutralization of toxicity against a human lung fibroblast cell line, IMR-90. FIG. 27 shows that all of the antibodies had neutralizing capacity towards IMR-90 cells. The relative neutralizing activity of toxin A cytotoxicity on IMR-90 cells was 124-152>1G10>2A11.

Example 16

Figure 24:
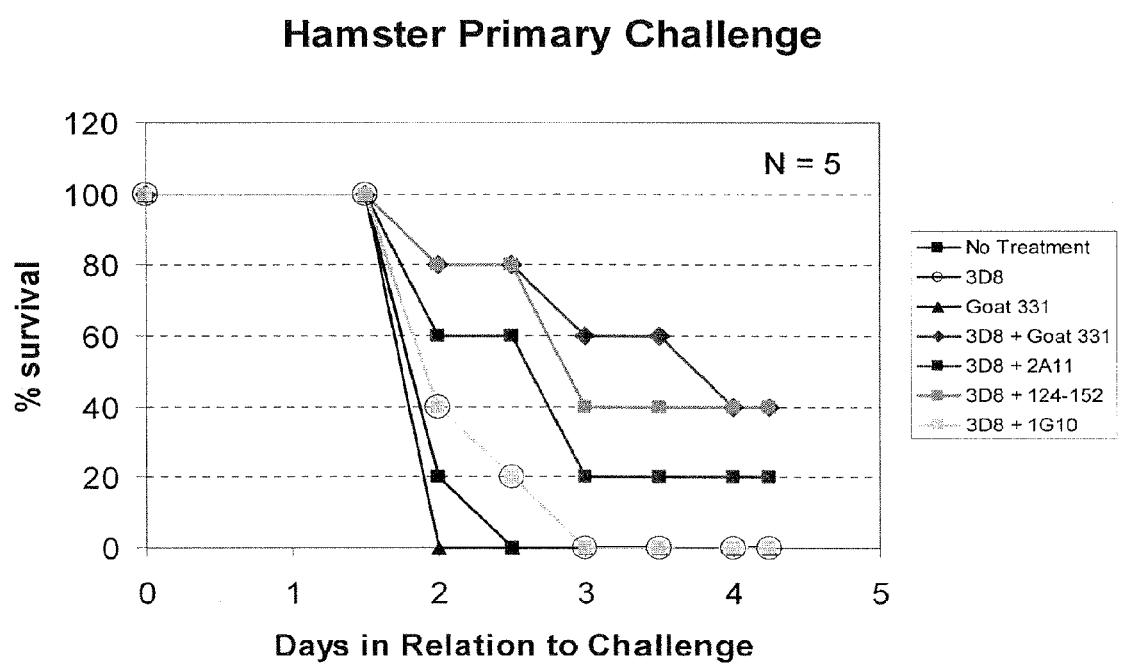
FIG. 24 is a graph depicting the results of primary challenge assays as the percentage of hamsters surviving direct C. difficile challenge.
Figure 25:
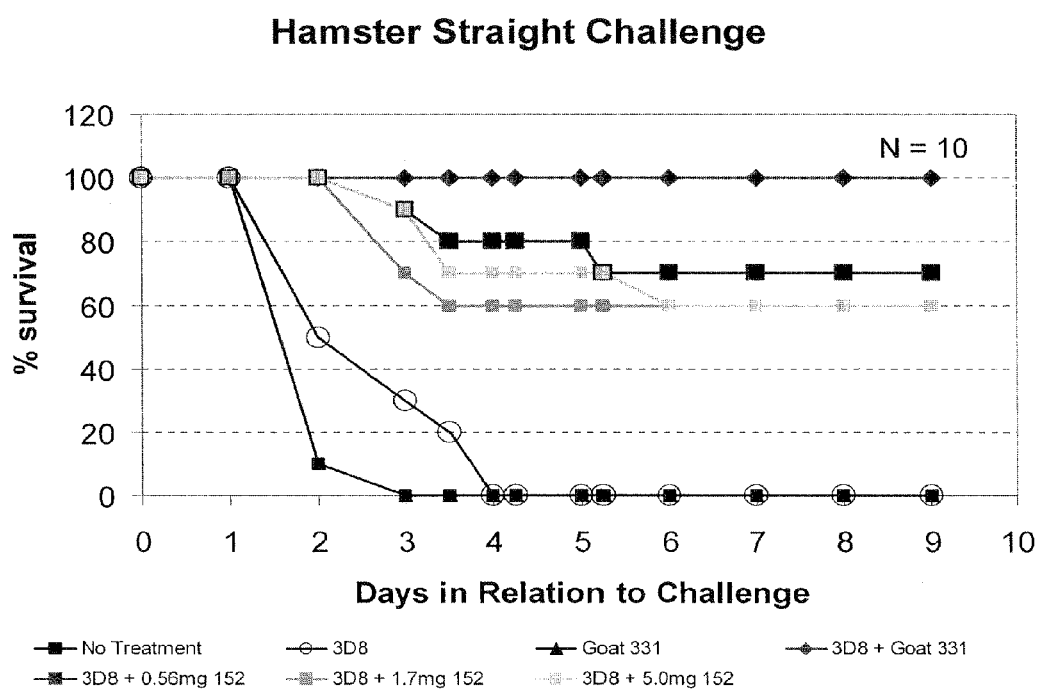
FIG. 25 is a graph depicting the results of primary challenge assays as the percentage of hamsters surviving direct C. difficile challenge.
Figure 26:
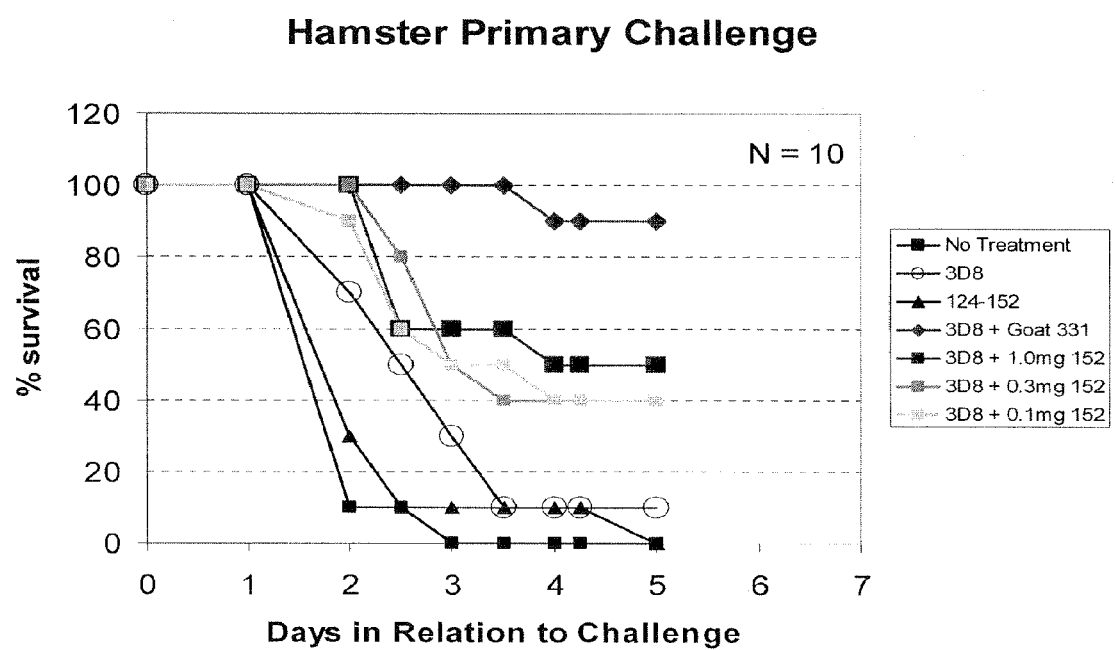
FIG. 26 is a graph depicting the results of primary challenge assays as the percentage of hamsters surviving direct C. difficile challenge.

Protection of Hamsters from Primary *C. difficile* Challenge Using Anti-Toxin B Antibodies Protection from direct challenge of an inoculum of *C. difficile* (clindamycin on day −1 and *C. difficile* spores on day 0 (1/100,000 dilution) was performed over a period of 4 to 10 days in the presence or absence of anti-toxin B antibodies. Groups of 5 hamsters were challenged after receiving once daily doses of 3D8 (20 mg total over 4 days), combined 3D8 (Id.) and goat #331 (3 ml) sera, 3D8 in combination with anti-toxin B antibodies 124-152 (18 mg total over 4 days), 2A11 (20 mg total over 4 days), or 1G10 (20 mg total over 4 days) or no antibodies for 3 days prior to challenge as depicted in FIG. 24. The data in FIG. 24 shows that animals receiving no antibodies or either 3D8 or goat sera alone all died within 72 hours of *C. difficile* challenge whereas animals receiving 3D8 and an anti-toxin B antibody, and preferably in combination with 124-152, had a 40% survival rate (FIG. 24). A 10 day study similar to the foregoing (but using a more dilute *C. difficile* inoculum) was performed with increasing amounts of the anti-toxin B antibody 124-152 (0.56 mg, 1.7 mg, or 5.0 mg given at days −3, −2, −1, and 0). Animals receiving both 3D8 and goat sera survived and most animals (60%-70%) survived for 10 days after challenge if given 3D8 in combination with 124-152. Even the lowest dosage of the anti-toxin B antibody 124-152 (0.56 mg in combination with 3D8) was highly effective (70% survival; see FIG. 25). Results show that 124-152 and 3D8, alone, are less effective then when used in combination where a more than additive, indeed, synergistic therapeutic result is achieved (FIGS. 24-26). These data provide further evidence that the anti-toxin B antibody is highly effective, especially in combination with the anti-toxin A antibody 3D8. Neutralization of toxin B in addition to toxin A was determined to provide for protection from *C. difficile* disease in this model.

Example 17

Epitope Mapping of Anti-Toxin B Antibodies

The epitope of toxin B bound by each monoclonal antibody was determined by western blotting. Recombinant *E. coli* clones were constructed which express fragments of toxin B representing different domains of toxin B. The appropriate segments of the toxin B gene were PCR-amplified from DNA prepared from an appropriate *C. difficile* strain. The fragments were cloned into an expression vector and expressed in *E. coli*. Human monoclonal antibody 152 was used to probe toxin B fragment in western blots in order to map the binding epitope. Toxin B protein fragments were isolated from *E. coli* containing a portion of the toxin B genes and separated using SDS-PAGE. After electrophoresis, the toxin B fragments were transferred to nitrocellulose and probed with monoclonal antibody 152 followed by alkaline phosphatase conjugated goat anti human to detect MAb 152 binding. HuMab 152 was determined to bind to the —COOH fragment portion of toxin B between amino acids 1777 and 2366 (see, for example, FIG. 32).

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating *Clostridium difficile* (*C. difficile*) disease in a subject, the method comprising administering to the subject:
   (a) an isolated monoclonal antibody that binds to *C. difficile* toxin A, or an antigen binding portion thereof, wherein the antibody binds to the same epitope of *C. difficile* toxin A recognized by an antibody comprising a heavy and light chain variable region having the amino acid sequences set forth in SEQ ID NOs: 1 and 4, SEQ ID NOs: 2 and 5, or SEQ ID NOs: 3 and 6, respectively; and
   (b) an isolated monoclonal antibody that binds to *C. difficile* toxin B, or an antigen binding portion thereof, wherein the antibody binds to the same epitope of *C. difficile* toxin B recognized by an antibody comprising a heavy and light chain variable region having the amino acid sequences set forth in SEQ ID NOs: 54 and 58, respectively,
   wherein *C. difficile* disease is treated in the subject.

2. A method of treating *Clostridium difficile* (*C. difficile*) disease in a subject, the method comprising administering to the subject:
   (a) an isolated monoclonal antibody that binds to *C. difficile* toxin A, or an antigen binding portion thereof, wherein the antibody is selected from the group consisting of:
      (i) an antibody comprising a heavy chain variable region CDR1 comprising SEQ ID NO:7, a heavy chain variable region CDR2 comprising SEQ ID NO:8, a heavy chain variable region CDR3 comprising SEQ ID NO:9, a light chain variable region CDR1 comprising SEQ ID NO:16, a light chain variable region CDR2 comprising SEQ ID NO:17 and a light chain variable region CDR3 comprising SEQ ID NO:18;
      (ii) an antibody comprising a heavy chain variable region CDR1 comprising SEQ ID NO:10, a heavy chain variable region CDR2 comprising SEQ ID NO:11, a heavy chain variable region CDR3 comprising SEQ ID NO:12, a light chain variable region CDR1 comprising SEQ ID NO:19, a light chain variable region CDR2 comprising SEQ ID NO:20 and a light chain variable region CDR3 comprising SEQ ID NO:21; and
      (iii) an antibody comprising a heavy chain variable region CDR1 comprising SEQ ID NO:13, a heavy chain variable region CDR2 comprising SEQ ID NO:14, a heavy chain variable region CDR3 comprising SEQ ID NO:15, a light chain variable region CDR1 comprising SEQ ID NO:22, a light chain variable region CDR2 comprising SEQ ID NO:23 and a light chain variable region CDR3 comprising SEQ ID NO:24;
   and
   (b) an isolated monoclonal antibody that binds to *C. difficile* toxin B, or an antigen binding portion thereof, wherein the antibody comprises a heavy chain variable region CDR1 comprising SEQ ID NO:62, a heavy chain variable region CDR2 comprising SEQ ID NO:64, a heavy chain variable region CDR3 comprising SEQ ID NO:66, a light chain variable region CDR1 comprising SEQ ID NO:68, a light chain variable region CDR2 comprising SEQ ID NO:70 and a light chain variable region CDR3 comprising SEQ ID NO:72,
wherein *C. difficile* disease is treated in the subject.

3. The method of claim 2, wherein the isolated monoclonal antibody that binds to *C. difficile* toxin A, or an antigen binding portion thereof, comprises a heavy chain variable region CDR1 comprising SEQ ID NO:7, a heavy chain variable region CDR2 comprising SEQ ID NO:8, a heavy chain variable region CDR3 comprising SEQ ID NO:9, a light chain variable region CDR1 comprising SEQ ID NO:16, a light chain variable region CDR2 comprising SEQ ID NO:17 and a light chain variable region CDR3 comprising SEQ ID NO:18.

4. The method of claim 2, wherein the isolated monoclonal antibody that binds to *C. difficile* toxin A, or an antigen binding portion thereof, comprises a heavy chain variable region CDR1 comprising SEQ ID NO:10, a heavy chain variable region CDR2 comprising SEQ ID NO:11, a heavy chain variable region CDR3 comprising SEQ ID NO:12, a light chain variable region CDR1 comprising SEQ ID NO:19, a light chain variable region CDR2 comprising SEQ ID NO:20 and a light chain variable region CDR3 comprising SEQ ID NO:21.

5. The method of claim 2, wherein the isolated monoclonal antibody that binds to *C. difficile* toxin A, or an antigen binding portion thereof, comprises a heavy chain variable region CDR1 comprising SEQ ID NO:13, a heavy chain variable region CDR2 comprising SEQ ID NO:14, a heavy chain variable region CDR3 comprising SEQ ID NO:15, a light chain variable region CDR1 comprising SEQ ID NO:22, a light chain variable region CDR2 comprising SEQ ID NO:23 and a light chain variable region CDR3 comprising SEQ ID NO:24.

6. The method of claim 2, wherein the method comprises administering to the subject:
(a) an isolated monoclonal antibody that binds to *C. difficile* toxin A, or an antigen binding portion thereof, wherein the antibody comprises a heavy and light chain variable region having the amino acid sequences set forth in SEQ ID NOs: 1 and 4, SEQ ID NOs: 2 and 5, or SEQ ID NOs: 3 and 6, respectively; and
(b) an isolated monoclonal antibody that binds to *C. difficile* toxin B, or an antigen binding portion thereof, wherein the antibody comprises a heavy and light chain variable region having the amino acid sequences set forth in SEQ ID NOs: 54 and 58, respectively,
wherein *C. difficile* disease is treated in the subject.

7. The method of claim 6, wherein the isolated monoclonal antibody that binds to *C. difficile* toxin A, or an antigen binding portion thereof, comprises heavy and light chain variable regions having the amino acid sequences set forth in SEQ ID NOs: 1 and 4, respectively.

8. The method of claim 6, wherein the isolated monoclonal antibody that binds to *C. difficile* toxin A, or an antigen binding portion thereof, comprises heavy and light chain variable regions having the amino acid sequences set forth in SEQ ID NOs: 2 and 5, respectively.

9. The method of claim 6, wherein the isolated monoclonal antibody that binds to *C. difficile* toxin A, or an antigen binding portion thereof, comprises heavy and light chain variable regions having the amino acid sequences set forth in SEQ ID NOs: 3 and 6, respectively.

10. The method of claim 1, wherein the antibodies, or antigen binding portions thereof, are administered separately.

11. The method of claim 1, wherein the antibodies, or antigen binding portions thereof, are administered together.

12. The method of claim 1, wherein the subject is human.

13. The method of claim 1, wherein the antibodies, or antigen binding portions thereof, are administered intravenously, intramuscularly, or subcutaneously to the subject.

14. The method of claim 1, wherein the *C. difficile* disease is antibiotic-associated diarrhea, *C. difficile*-mediated pseudomembranous colitis (PMC), diarrhea, or relapse of *C. difficile*-mediated disease.

15. The method of claim 1, wherein the antibodies, or antigen binding portions thereof, are administered in combination with an antibiotic or *C. difficile* vaccine.

16. The method of claim 15, wherein the antibiotic is vancomycin or metronidazole.

17. The method of claim 2, wherein the antibodies, or antigen binding portions thereof, are administered separately.

18. The method of claim 2, wherein the antibodies, or antigen binding portions thereof, are administered together.

19. The method of claim 2, wherein the subject is human.

20. The method of claim 2, wherein the antibodies, or antigen binding portions thereof, are administered intravenously, intramuscularly, or subcutaneously to the subject.

21. The method of claim 2, wherein the *C. difficile* disease is antibiotic-associated diarrhea, *C. difficile*-mediated pseudomembranous colitis (PMC), diarrhea, or relapse of *C. difficile*-mediated disease.

22. The method of claim 2, wherein the antibodies, or antigen binding portions thereof, are administered in combination with an antibiotic or *C. difficile* vaccine.

23. The method of claim 22, wherein the antibiotic is vancomycin or metronidazole.

24. The method of claim 6, wherein the antibodies, or antigen binding portions thereof, are administered separately.

25. The method of claim 6, wherein the antibodies, or antigen binding portions thereof, are administered together.

26. The method of claim 6, wherein the subject is human.

27. The method of claim 6, wherein the antibodies, or antigen binding portions thereof, are administered intravenously, intramuscularly, or subcutaneously to the subject.

28. The method of claim 6, wherein the *C. difficile* disease is antibiotic-associated diarrhea, *C. difficile*-mediated pseudomembranous colitis (PMC), diarrhea, or relapse of *C. difficile*-mediated disease.

29. The method of claim 6, wherein the antibodies, or antigen binding portions thereof, are administered in combination with an antibiotic or *C. difficile* vaccine.

30. The method of claim 29, wherein the antibiotic is vancomycin or metronidazole.

* * * * *

SEQUENCE LISTING

<160> NUMBER OF SEQ ID NOS: 82

<210> SEQ ID NO 1
<211> LENGTH: 122
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Asn Tyr

```
                   20                  25                  30

Gly Met His Trp Val Arg Gln Ala Pro Gly Lys Gly Leu Glu Trp Val
            35                  40                  45

Ala Leu Ile Trp Tyr Asp Gly Ser Asn Glu Asp Tyr Thr Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Met Val Arg Gly Val Ile Asp Val Phe Asp Ile Trp
            100                 105                 110

Gly Gln Gly Thr Val Val Thr Val Ser Ser
            115                 120

<210> SEQ ID NO 2
<211> LENGTH: 114
<212> TYPE: PRT
<213> ORGANISM: Homo sapiens

<400> SEQUENCE: 2

Gln Met Gln Leu Val Glu Ser Gly Gly Gly Val Val Gln Pro Gly Arg
1               5                   10                  15

Ser Leu Arg Leu Ser Cys Glu Ala Ser Gly Phe Ser Phe Asn Ser Tyr
            20                  25                  30

Gly Met His Trp Val Arg Gln Ala Pro Gly Lys Gly Leu Glu Trp Val
        35                  40                  45

Ser Val Ile Trp Ala Ser Gly Asn Lys Lys Tyr Tyr Ile Glu Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Phe Asp Tyr Trp Gly Gln Gly Thr Leu Val Thr Val
            100                 105                 110

Ser Ser

<210> SEQ ID NO 3
<211> LENGTH: 116
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Lys Tyr
            20                  25                  30

Gly Met His Trp Val Arg Gln Ala Pro Gly Lys Gly Leu Glu Trp Val
        35                  40                  45

Ala Val Ile Trp Tyr Asp Gly Thr Asn Lys Tyr Tyr Ala Asp Ser Met
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Pro Thr Ala Asn Tyr Trp Gly Gln Gly Thr Leu Val
            100                 105                 110
```

```
Thr Val Ser Ser
        115

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln His Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Trp
                 85                  90                  95

Thr Phe Gly Gln Gly Thr Lys Val Glu Ile Lys
            100                 105

<210> SEQ ID NO 5
<211> LENGTH: 108
<212> TYPE: PRT
<213> ORGANISM: Homo sapiens

<400> SEQUENCE: 5

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Ser Gln
                 85                  90                  95

Phe Thr Phe Gly Pro Gly Thr Lys Val Asp Ile Lys
            100                 105

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Ser Tyr Pro Val
                 85                  90                  95

Thr Phe Gly Gly Gly Thr Lys Val Glu Ile Lys
            100                 105

<210> SEQ ID NO 7
<211> LENGTH: 5
<212> TYPE: PRT
<213> ORGANISM: Homo sapiens

<400> SEQUENCE: 7

Asn Tyr Gly Met His
 1               5

<210> SEQ ID NO 8
<211> LENGTH: 17
<212> TYPE: PRT
<213> ORGANISM: Homo sapiens

<400> SEQUENCE: 8

Leu Ile Trp Tyr Asp Gly Ser Asn Glu Asp Tyr Thr Asp Ser Val Lys
 1               5                  10                  15

Gly

<210> SEQ ID NO 9
<211> LENGTH: 13
<212> TYPE: PRT
<213> ORGANISM: Homo sapiens

<400> SEQUENCE: 9

Trp Gly Met Val Arg Gly Val Ile Asp Val Phe Asp Ile
 1               5                  10

<210> SEQ ID NO 10
<211> LENGTH: 5
<212> TYPE: PRT
<213> ORGANISM: Homo sapiens

<400> SEQUENCE: 10

Ser Tyr Gly Met His
 1               5

<210> SEQ ID NO 11
<211> LENGTH: 17
<212> TYPE: PRT
<213> ORGANISM: Homo sapiens

<400> SEQUENCE: 11

Val Ile Trp Ala Ser Gly Asn Lys Lys Tyr Tyr Ile Glu Ser Val Glu
 1               5                  10                  15

Gly

<210> SEQ ID NO 12
<211> LENGTH: 5
<212> TYPE: PRT
<213> ORGANISM: Homo sapiens

<400> SEQUENCE: 12

Ala Asn Phe Asp Tyr
 1               5
```

```
<210> SEQ ID NO 13
<211> LENGTH: 5
<212> TYPE: PRT
<213> ORGANISM: Homo sapiens

<400> SEQUENCE: 13

Lys Tyr Gly Met His
 1               5

<210> SEQ ID NO 14
<211> LENGTH: 17
<212> TYPE: PRT
<213> ORGANISM: Homo sapiens

<400> SEQUENCE: 14

Val Ile Trp Tyr Asp Gly Thr Asn Lys Tyr Tyr Ala Asp Ser Met Lys
 1               5                  10                  15

Gly

<210> SEQ ID NO 15
<211> LENGTH: 7
<212> TYPE: PRT
<213> ORGANISM: Homo sapiens

<400> SEQUENCE: 15

Asp Pro Pro Thr Ala Asn Tyr
 1               5

<210> SEQ ID NO 16
<211> LENGTH: 11
<212> TYPE: PRT
<213> ORGANISM: Homo sapiens

<400> SEQUENCE: 16

Arg Ala Ser Gln Gly Ile Ser Ser Trp Leu Ala
 1               5                  10

<210> SEQ ID NO 17
<211> LENGTH: 7
<212> TYPE: PRT
<213> ORGANISM: Homo sapiens

<400> SEQUENCE: 17

Ala Ala Ser Ser Leu Gln Ser
 1               5

<210> SEQ ID NO 18
<211> LENGTH: 9
<212> TYPE: PRT
<213> ORGANISM: Homo sapiens

<400> SEQUENCE: 18

Gln Gln Ala Asn Ser Phe Pro Trp Thr
 1               5

<210> SEQ ID NO 19
<211> LENGTH: 11
<212> TYPE: PRT
<213> ORGANISM: Homo sapiens

<400> SEQUENCE: 19

Arg Ala Ser Gln Ser Val Ser Ser Tyr Leu Ala
 1               5                  10
```

```
<210> SEQ ID NO 20
<211> LENGTH: 7
<212> TYPE: PRT
<213> ORGANISM: Homo sapiens

<400> SEQUENCE: 20

Asp Ala Ser Asn Arg Ala Thr
 1               5

<210> SEQ ID NO 21
<211> LENGTH: 10
<212> TYPE: PRT
<213> ORGANISM: Homo sapiens

<400> SEQUENCE: 21

Gln Gln Arg Ser Asn Trp Ser Gln Phe Thr
 1               5                  10

<210> SEQ ID NO 22
<211> LENGTH: 11
<212> TYPE: PRT
<213> ORGANISM: Homo sapiens

<400> SEQUENCE: 22

Arg Ala Ser Gln Gly Ile Ser Ser Trp Leu Ala
 1               5                  10

<210> SEQ ID NO 23
<211> LENGTH: 7
<212> TYPE: PRT
<213> ORGANISM: Homo sapiens

<400> SEQUENCE: 23

Ala Ala Ser Ser Leu Gln Ser
 1               5

<210> SEQ ID NO 24
<211> LENGTH: 9
<212> TYPE: PRT
<213> ORGANISM: Homo sapiens

<400> SEQUENCE: 24

Gln Gln Tyr Lys Ser Tyr Pro Val Thr
 1               5

<210> SEQ ID NO 25
<211> LENGTH: 11
<212> TYPE: PRT
<213> ORGANISM: Homo sapiens
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (9)
<223> OTHER INFORMATION: Variable amino acid

<400> SEQUENCE: 25

Arg Ala Ser Gln Xaa Xaa Ser Ser Xaa Leu Ala
 1               5                  10

<210> SEQ ID NO 26
<211> LENGTH: 6
<212> TYPE: PRT
<213> ORGANISM: Homo sapiens
<220> FEATURE:
<221> NAME/KEY: MOD_RES
```

```
<222> LOCATION: (3)..(5)
<223> OTHER INFORMATION: Variable amino acid
<220> FEATURE:
<221> NAME/KEY: MOD_RES
<222> LOCATION: (6)
<223> OTHER INFORMATION: Ser or Thr

<400> SEQUENCE: 26

Ala Ser Xaa Xaa Xaa Xaa
 1               5

<210> SEQ ID NO 27
<211> LENGTH: 7
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (5)
<223> OTHER INFORMATION: Ser or Asn
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (7)
<223> OTHER INFORMATION: Pro or Ser

<400> SEQUENCE: 27

Gln Gln Xaa Xaa Xaa Xaa Xaa
 1               5

<210> SEQ ID NO 28
<211> LENGTH: 4
<212> TYPE: PRT
<213> ORGANISM: Homo sapiens

<400> SEQUENCE: 28

Tyr Gly Met His
 1

<210> SEQ ID NO 29
<211> LENGTH: 15
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)..(8)
<223> OTHER INFORMATION: Variable amino acid
<220> FEATURE:
<221> NAME/KEY: MOD_RES
<222> LOCATION: (10)..(11)
<223> OTHER INFORMATION: Variable amino acid
<220> FEATURE:
<221> NAME/KEY: MOD_RES
<222> LOCATION: (13)..(14)
<223> OTHER INFORMATION: Variable amino acid

<400> SEQUENCE: 29

Ile Trp Xaa Xaa Gly Xaa Xaa Xaa Tyr Xaa Xaa Ser Xaa Xaa Gly
 1               5                  10                  15

<210> SEQ ID NO 30
<211> LENGTH: 107
```

```
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 31
<211> LENGTH: 107
<212> TYPE: PRT
<213> ORGANISM: Homo sapiens

<400> SEQUENCE: 31

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95
```

Thr Phe Gly Gln Gly Thr Lys Val Glu Ile Lys
            100                 105

<210> SEQ ID NO 33
<211> LENGTH: 107
<212> TYPE: PRT
<213> ORGANISM: Homo sapiens

<400> SEQUENCE: 33

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Trp
                 85                  90                  95

Thr Phe Gly Gln Gly Thr Lys Val Glu Ile Lys
            100                 105

<210> SEQ ID NO 34
<211> LENGTH: 107
<212> TYPE: PRT
<213> ORGANISM: Homo sapiens

<400> SEQUENCE: 34

Asp Ile Gln Met Thr Gln Ser Leu Ser Ser Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Trp
                 85                  90                  95

Thr Phe Gly Gln Gly Thr Lys Val Glu Ile Lys
            100                 105

<210> SEQ ID NO 35
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 35 gac atc cag atg acc cag tct cca tct tcc gtg tct gca tct gta gga       48
Asp Ile Gln Met Thr Gln Ser Pro Ser Ser Val Ser Ala Ser Val Gly
  1               5                  10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
             20                  25                  30

```
tta gcc tgg tat cag cat aaa cca ggg aaa gcc cct aag ctc ctg atc      144
Leu Ala Trp Tyr Gln His Lys Pro Gly Lys Ala Pro Lys Leu Leu Ile
         35                  40                  45 tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
 50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80 gaa gat ttt gca act tac tat tgt caa cag gct aat agt ttc cct tgg      288
Glu Asp Phe Ala Thr Tyr Tyr Cys Gln Gln Ala Asn Ser Phe Pro Trp
                 85                  90                  95 acg ttc ggc caa ggg acc aag gtg gaa atc aaa                          321
Thr Phe Gly Gln Gly Thr Lys Val Glu Ile Lys
             100                 105

<210> SEQ ID NO 36
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 36 gaa att gtg ttg aca cag tct cca gcc acc ctg tct ttg tct cca ggg       48
Glu Ile Val Leu Thr Gln Ser Pro Ala Thr Leu Ser Leu Ser Pro Gly
  1               5                  10                  15 gaa aga gcc acc ctc tcc tgc agg gcc agt cag agt gtt agc agc tac       96
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc ctc atc      144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc      192
Tyr Asp Ala Ser Asn Arg Ala Thr Gly Ile Pro Ala Arg Phe Ser Gly
 50                  55                  60 agt ggg tct ggg aca gac ttc act ctc acc atc agc agc cta gag cct      240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt agc aac tgg tct caa      288
Glu Asp Phe Ala Val Tyr Tyr Cys Gln Gln Arg Ser Asn Trp Ser Gln
                 85                  90                  95 ttc act ttc ggc cct ggg acc aaa gtg gat atc aaa                      324
Phe Thr Phe Gly Pro Gly Thr Lys Val Asp Ile Lys
             100                 105

<210> SEQ ID NO 37
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 37 gac atc cag atg acc cag tct cca tcc tca ctg tct gca tct gta gga       48
Asp Ile Gln Met Thr Gln Ser Pro Ser Ser Leu Ser Ala Ser Val Gly
  1               5                  10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
             20                  25                  30 tta gcc tgg tat cag cag aaa cca gag aaa gcc cct aag tcc ctg atc      144
```

```
Leu Ala Trp Tyr Gln Gln Lys Pro Glu Lys Ala Pro Lys Ser Leu Ile
         35                  40                  45 tat gct gca tcc agt ttg caa agt ggg gtc cca tca agg ttc agc ggc    192
Tyr Ala Ala Ser Ser Leu Gln Ser Gly Val Pro Ser Arg Phe Ser Gly
     50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gca act tat tac tgc caa cag tat aag agt tac ccg gtc    288
Glu Asp Phe Ala Thr Tyr Tyr Cys Gln Gln Tyr Lys Ser Tyr Pro Val
                 85                  90                  95 act ttc ggc gga ggg acc aag gtg gag atc aaa                        321
Thr Phe Gly Gly Gly Thr Lys Val Glu Ile Lys
             100                 105

<210> SEQ ID NO 38
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 38 cag gtg cag ctg gtg gag tct ggg gga ggc gtg gtc cag cct ggc agg     48
Gln Val Gln Leu Val Glu Ser Gly Gly Gly Val Val Gln Pro Gly Arg
 1               5                  10                  15 tcc ctg aga ctc tcc tgt gcg gcg tct gga ttc agc ttc agt aac tat     96
Ser Leu Arg Leu Ser Cys Ala Ala Ser Gly Phe Ser Phe Ser Asn Tyr
             20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
         35                  40                  45 gca ctt ata tgg tat gat gga agt aat gag gac tat aca gac tcc gtg    192
Ala Leu Ile Trp Tyr Asp Gly Ser Asn Glu Asp Tyr Thr Asp Ser Val
     50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt    288
Leu Gln Met Asn Ser Leu Arg Ala Glu Asp Thr Ala Val Tyr Tyr Cys
                 85                  90                  95 gcg aga tgg ggg atg gtt cgg gga gtt atc gat gtt ttt gat atc tgg    336
Ala Arg Trp Gly Met Val Arg Gly Val Ile Asp Val Phe Asp Ile Trp
            100                 105                 110 ggc caa ggg aca gtg gtc acc gtc tct tca                            366
Gly Gln Gly Thr Val Val Thr Val Ser Ser
        115                 120

<210> SEQ ID NO 39
<211> LENGTH: 342
<212> TYPE: DNA
<213> ORGANISM: Homo sapiens
<220> FEATURE:
<221> NAME/KEY: CDS
<222> LOCATION: (1)..(342)

<400> SEQUENCE: 39 cag atg cag ctg gtg gag tct ggg ggc ggc gtg gtc cag cct ggg agg     48
Gln Met Gln Leu Val Glu Ser Gly Gly Gly Val Val Gln Pro Gly Arg
 1               5                  10                  15 tcc ctg aga ctc tcc tgt gaa gcg tct gga ttc tcc ttc aat agc tat     96
Ser Leu Arg Leu Ser Cys Glu Ala Ser Gly Phe Ser Phe Asn Ser Tyr
             20                  25                  30
```

```
ggc atg cac tgg gtc cgc cag gct cca ggc aag ggg ctg gag tgg gtg      144
Gly Met His Trp Val Arg Gln Ala Pro Gly Lys Gly Leu Glu Trp Val
         35                  40                  45 tca gtc ata tgg gcc agt gga aat aag aaa tat tat ata gaa tcc gtg      192
Ser Val Ile Trp Ala Ser Gly Asn Lys Lys Tyr Tyr Ile Glu Ser Val
 50                  55                  60 gag ggc cga ttc acc atc tcc aga gac aat tcc aag aac acg ctg tat      240
Glu Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                 85                  90                  95 gcg aga gcc aat ttt gac tac tgg ggc cag gga acc ctg gtc acc gtc      336
Ala Arg Ala Asn Phe Asp Tyr Trp Gly Gln Gly Thr Leu Val Thr Val
            100                 105                 110 tcc tca                                                              342
Ser Ser <210> SEQ ID NO 40
<211> LENGTH: 348
<212> TYPE: DNA
<213> ORGANISM: Homo sapiens
<220> FEATURE:
<221> NAME/KEY: CDS
<222> LOCATION: (1)..(348)

<400> SEQUENCE: 40 cag gtg cag ctg gtg gag tct ggg gga ggc gtg gtc cag cct ggg agg       48
Gln Val Gln Leu Val Glu Ser Gly Gly Gly Val Val Gln Pro Gly Arg
  1               5                  10                  15 tcc ctg aga ctc tcc tgt gca gcg tct gga ttc acc ttc aat aaa tat       96
Ser Leu Arg Leu Ser Cys Ala Ala Ser Gly Phe Thr Phe Asn Lys Tyr
             20                  25                  30 ggc atg cac tgg gtc cgc cag gct cca ggc aag ggg ctg gag tgg gtg      144
Gly Met His Trp Val Arg Gln Ala Pro Gly Lys Gly Leu Glu Trp Val
         35                  40                  45 gca gtt ata tgg tat gat gga act aat aaa tac tat gca gac tcc atg      192
Ala Val Ile Trp Tyr Asp Gly Thr Asn Lys Tyr Tyr Ala Asp Ser Met
 50                  55                  60 aag ggc cga ttc acc atc tcc aga gac aat tcc aag aat atg ctg tat      240
Lys Gly Arg Phe Thr Ile Ser Arg Asp Asn Ser Lys Asn Met Leu Tyr
 65                  70                  75                  80 ctg caa atg aac agc cta aga gcc gag gac acg gct gtg tat tac tgt      288
Leu Gln Met Asn Ser Leu Arg Ala Glu Asp Thr Ala Val Tyr Tyr Cys
                 85                  90                  95 gcg aga gat ccc ccc act gct aac tac tgg ggc cag gga acc ctg gtc      336
Ala Arg Asp Pro Pro Thr Ala Asn Tyr Trp Gly Gln Gly Thr Leu Val
            100                 105                 110 acc gtc tcc tca                                                      348
Thr Val Ser Ser
        115

<210> SEQ ID NO 41
<211> LENGTH: 2710
<212> TYPE: PRT
<213> ORGANISM: Clostridium difficile

<400> SEQUENCE: 41

Met Ser Leu Ile Ser Lys Glu Glu Leu Ile Lys Leu Ala Tyr Ser Ile
  1               5                  10                  15

Arg Pro Arg Glu Asn Glu Tyr Lys Thr Ile Leu Thr Asn Leu Asp Glu
             20                  25                  30
```

```
Tyr Asn Lys Leu Thr Thr Asn Asn Glu Asn Lys Tyr Leu Gln Leu
         35                  40                  45

Lys Lys Leu Asn Glu Ser Ile Asp Val Phe Met Asn Lys Tyr Lys Thr
 50                  55                  60

Ser Ser Arg Asn Arg Ala Leu Ser Asn Leu Lys Lys Asp Ile Leu Lys
 65                  70                  75                  80

Glu Val Ile Leu Ile Lys Asn Ser Asn Thr Ser Pro Val Glu Lys Asn
                 85                  90                  95

Leu His Phe Val Trp Ile Gly Gly Glu Val Ser Asp Ile Ala Leu Glu
                100                 105                 110

Tyr Ile Lys Gln Trp Ala Asp Ile Asn Ala Glu Tyr Asn Ile Lys Leu
            115                 120                 125

Trp Tyr Asp Ser Glu Ala Phe Leu Val Asn Thr Leu Lys Lys Ala Ile
        130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
```

```
                    450             455             460
Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                    485                 490                 495

Leu Ile Glu Phe Lys Phe Pro Glu Asn Asn Leu Ser Gln Leu Thr Glu
                500                 505                 510

Gln Glu Ile Asn Ser Leu Trp Ser Phe Asp Gln Ala Ser Ala Lys Tyr
            515                 520                 525

Gln Phe Glu Lys Tyr Val Arg Asp Tyr Thr Gly Gly Ser Leu Ser Glu
        530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Glu Ala Gly Ser
                565                 570                 575

Lys Asn Tyr Val His Tyr Ile Ile Gln Leu Gln Gly Asp Asp Ile Ser
                580                 585                 590

Tyr Glu Ala Thr Cys Asn Leu Phe Ser Lys Asn Pro Lys Asn Ser Ile
                595                 600                 605

Ile Ile Gln Arg Asn Met Asn Glu Ser Ala Lys Ser Tyr Phe Leu Ser
610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
                660                 665                 670

Leu Ser Asn Glu Ile Ser Ser Phe Leu Asp Thr Ile Lys Leu Asp Ile
            675                 680                 685

Ser Pro Lys Asn Val Glu Val Asn Leu Leu Gly Cys Asn Met Phe Ser
            690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
                740                 745                 750

Arg Lys Glu Leu Leu Ala His Ser Gly Lys Trp Ile Asn Lys Glu Glu
            755                 760                 765

Ala Ile Met Ser Asp Leu Ser Ser Lys Glu Tyr Ile Phe Phe Asp Ser
770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Asp Ala Ser Val Ser
                805                 810                 815

Pro Asp Thr Lys Phe Ile Leu Asn Asn Leu Lys Leu Asn Ile Glu Ser
                820                 825                 830

Ser Ile Gly Asp Tyr Ile Tyr Tyr Glu Lys Leu Glu Pro Val Lys Asn
            835                 840                 845

Ile Ile His Asn Ser Ile Asp Asp Leu Ile Asp Glu Phe Asn Leu Leu
        850                 855                 860

Glu Asn Val Ser Asp Glu Leu Tyr Glu Leu Lys Lys Leu Asn Asn Leu
865                 870                 875                 880
```

-continued

```
Asp Glu Lys Tyr Leu Ile Ser Phe Glu Asp Ile Ser Lys Asn Asn Ser
            885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
            915                 920                 925

Lys Glu Ile Ser Thr Ile Lys Asn Ser Ile Ile Thr Asp Val Asn Gly
            930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
            965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
            995                 1000                1005

Leu Val Asn Leu Ile Ser Asn Ala Val Asn Asp Thr Ile Asn Val Leu
    1010                1015                1020

Pro Thr Ile Thr Glu Gly Ile Pro Ile Val Ser Thr Ile Leu Asp Gly
1025                1030                1035                1040

Ile Asn Leu Gly Ala Ala Ile Lys Glu Leu Leu Asp Glu His Asp Pro
            1045                1050                1055

Leu Leu Lys Lys Glu Leu Glu Ala Lys Val Gly Val Leu Ala Ile Asn
            1060                1065                1070

Met Ser Leu Ser Ile Ala Ala Thr Val Ala Ser Ile Val Gly Ile Gly
            1075                1080                1085

Ala Glu Val Thr Ile Phe Leu Leu Pro Ile Ala Gly Ile Ser Ala Gly
            1090                1095                1100

Ile Pro Ser Leu Val Asn Asn Glu Leu Ile Leu His Asp Lys Ala Thr
1105                1110                1115                1120

Ser Val Val Asn Tyr Phe Asn His Leu Ser Glu Ser Lys Lys Tyr Gly
            1125                1130                1135

Pro Leu Lys Thr Glu Asp Asp Lys Ile Leu Val Pro Ile Asp Asp Leu
            1140                1145                1150

Val Ile Ser Glu Ile Asp Phe Asn Asn Asn Ser Ile Lys Leu Gly Thr
            1155                1160                1165

Cys Asn Ile Leu Ala Met Glu Gly Gly Ser Gly His Thr Val Thr Gly
            1170                1175                1180

Asn Ile Asp His Phe Phe Ser Ser Pro Ser Ile Ser Ser His Ile Pro
1185                1190                1195                1200

Ser Leu Ser Ile Tyr Ser Ala Ile Gly Ile Glu Thr Glu Asn Leu Asp
            1205                1210                1215

Phe Ser Lys Lys Ile Met Met Leu Pro Asn Ala Pro Ser Arg Val Phe
            1220                1225                1230

Trp Trp Glu Thr Gly Ala Val Pro Gly Leu Arg Ser Leu Glu Asn Asp
            1235                1240                1245

Gly Thr Arg Leu Leu Asp Ser Ile Arg Asp Leu Tyr Pro Gly Lys Phe
            1250                1255                1260

Tyr Trp Arg Phe Tyr Ala Phe Phe Asp Tyr Ala Ile Thr Thr Leu Lys
1265                1270                1275                1280

Pro Val Tyr Glu Asp Thr Asn Ile Lys Ile Lys Leu Asp Lys Asp Thr
            1285                1290                1295

Arg Asn Phe Ile Met Pro Thr Ile Thr Thr Asn Glu Ile Arg Asn Lys
            1300                1305                1310
```

```
Leu Ser Tyr Ser Phe Asp Gly Ala Gly Gly Thr Tyr Ser Leu Leu Leu
        1315                1320                1325

Ser Ser Tyr Pro Ile Ser Thr Asn Ile Asn Leu Ser Lys Asp Asp Leu
        1330                1335                1340

Trp Ile Phe Asn Ile Asp Asn Glu Val Arg Glu Ile Ser Ile Glu Asn
1345                1350                1355                1360

Gly Thr Ile Lys Lys Gly Lys Leu Ile Lys Asp Val Leu Ser Lys Ile
        1365                1370                1375

Asp Ile Asn Lys Asn Lys Leu Ile Ile Gly Asn Gln Thr Ile Asp Phe
            1380                1385                1390

Ser Gly Asp Ile Asp Asn Lys Asp Arg Tyr Ile Phe Leu Thr Cys Glu
        1395                1400                1405

Leu Asp Asp Lys Ile Ser Leu Ile Ile Glu Ile Asn Leu Val Ala Lys
    1410                1415                1420

Ser Tyr Ser Leu Leu Ser Gly Asp Lys Asn Tyr Leu Ile Ser Asn
    1425                1430                1435                1440

Leu Ser Asn Thr Ile Glu Lys Ile Asn Thr Leu Gly Leu Asp Ser Lys
                1445                1450                1455

Asn Ile Ala Tyr Asn Tyr Thr Asp Glu Ser Asn Asn Lys Tyr Phe Gly
            1460                1465                1470

Ala Ile Ser Lys Thr Ser Gln Lys Ser Ile Ile His Tyr Lys Lys Asp
        1475                1480                1485

Ser Lys Asn Ile Leu Glu Phe Tyr Asn Asp Ser Thr Leu Glu Phe Asn
        1490                1495                1500

Ser Lys Asp Phe Ile Ala Glu Asp Ile Asn Val Phe Met Lys Asp Asp
1505                1510                1515                1520

Ile Asn Thr Ile Thr Gly Lys Tyr Tyr Val Asp Asn Asn Thr Asp Lys
            1525                1530                1535

Ser Ile Asp Phe Ser Ile Ser Leu Val Ser Lys Asn Gln Val Lys Val
        1540                1545                1550

Asn Gly Leu Tyr Leu Asn Glu Ser Val Tyr Ser Ser Tyr Leu Asp Phe
    1555                1560                1565

Val Lys Asn Ser Asp Gly His His Asn Thr Ser Asn Phe Met Asn Leu
    1570                1575                1580

Phe Leu Asp Asn Ile Ser Phe Trp Lys Leu Phe Gly Phe Glu Asn Ile
1585                1590                1595                1600

Asn Phe Val Ile Asp Lys Tyr Phe Thr Leu Val Gly Lys Thr Asn Leu
            1605                1610                1615

Gly Tyr Val Glu Phe Ile Cys Asp Asn Asn Lys Asn Ile Asp Ile Tyr
        1620                1625                1630

Phe Gly Glu Trp Lys Thr Ser Ser Ser Lys Ser Thr Ile Phe Ser Gly
        1635                1640                1645

Asn Gly Arg Asn Val Val Val Glu Pro Ile Tyr Asn Pro Asp Thr Gly
    1650                1655                1660

Glu Asp Ile Ser Thr Ser Leu Asp Phe Ser Tyr Glu Pro Leu Tyr Gly
1665                1670                1675                1680

Ile Asp Arg Tyr Ile Asn Lys Val Leu Ile Ala Pro Asp Leu Tyr Thr
            1685                1690                1695

Ser Leu Ile Asn Ile Asn Thr Asn Tyr Tyr Ser Asn Glu Tyr Tyr Pro
            1700                1705                1710

Glu Ile Ile Val Leu Asn Pro Asn Thr Phe His Lys Lys Val Asn Ile
        1715                1720                1725

Asn Leu Asp Ser Ser Ser Phe Glu Tyr Lys Trp Ser Thr Glu Gly Ser
```

-continued

```
          1730              1735              1740
Asp Phe Ile Leu Val Arg Tyr Leu Glu Glu Ser Asn Lys Lys Ile Leu
1745              1750              1755              1760

Gln Lys Ile Arg Ile Lys Gly Ile Leu Ser Asn Thr Gln Ser Phe Asn
          1765              1770              1775

Lys Met Ser Ile Asp Phe Lys Asp Ile Lys Lys Leu Ser Leu Gly Tyr
          1780              1785              1790

Ile Met Ser Asn Phe Lys Ser Phe Asn Ser Glu Asn Glu Leu Asp Arg
          1795              1800              1805

Asp His Leu Gly Phe Lys Ile Ile Asp Asn Lys Thr Tyr Tyr Tyr Asp
          1810              1815              1820

Glu Asp Ser Lys Leu Val Lys Gly Leu Ile Asn Ile Asn Asn Ser Leu
1825              1830              1835              1840

Phe Tyr Phe Asp Pro Ile Glu Phe Asn Leu Val Thr Gly Trp Gln Thr
          1845              1850              1855

Ile Asn Gly Lys Lys Tyr Tyr Phe Asp Ile Asn Thr Gly Ala Ala Leu
          1860              1865              1870

Thr Ser Tyr Lys Ile Ile Asn Gly Lys His Phe Tyr Phe Asn Asn Asp
          1875              1880              1885

Gly Val Met Gln Leu Gly Val Phe Lys Gly Pro Asp Gly Phe Glu Tyr
          1890              1895              1900

Phe Ala Pro Ala Asn Thr Gln Asn Asn Asn Ile Glu Gly Gln Ala Ile
1905              1910              1915              1920

Val Tyr Gln Ser Lys Phe Leu Thr Leu Asn Gly Lys Lys Tyr Tyr Phe
          1925              1930              1935

Asp Asn Asn Ser Lys Ala Val Thr Gly Trp Arg Ile Ile Asn Asn Glu
          1940              1945              1950

Lys Tyr Tyr Phe Asn Pro Asn Asn Ala Ile Ala Ala Val Gly Leu Gln
          1955              1960              1965

Val Ile Asp Asn Asn Lys Tyr Tyr Phe Asn Pro Asp Thr Ala Ile Ile
          1970              1975              1980

Ser Lys Gly Trp Gln Thr Val Asn Gly Ser Arg Tyr Tyr Phe Asp Thr
1985              1990              1995              2000

Asp Thr Ala Ile Ala Phe Asn Gly Tyr Lys Thr Ile Asp Gly Lys His
          2005              2010              2015

Phe Tyr Phe Asp Ser Asp Cys Val Val Lys Ile Gly Val Phe Ser Thr
          2020              2025              2030

Ser Asn Gly Phe Glu Tyr Phe Ala Pro Ala Asn Thr Tyr Asn Asn Asn
          2035              2040              2045

Ile Glu Gly Gln Ala Ile Val Tyr Gln Ser Lys Phe Leu Thr Leu Asn
          2050              2055              2060

Gly Lys Lys Tyr Tyr Phe Asp Asn Asn Ser Lys Ala Val Thr Gly Trp
2065              2070              2075              2080

Gln Thr Ile Asp Ser Lys Lys Tyr Tyr Phe Asn Thr Asn Thr Ala Glu
          2085              2090              2095

Ala Ala Thr Gly Trp Gln Thr Ile Asp Gly Lys Lys Tyr Tyr Phe Asn
          2100              2105              2110

Thr Asn Thr Ala Glu Ala Ala Thr Gly Trp Gln Thr Ile Asp Gly Lys
          2115              2120              2125

Lys Tyr Tyr Phe Asn Thr Asn Thr Ala Ile Ala Ser Thr Gly Tyr Thr
          2130              2135              2140

Ile Ile Asn Gly Lys His Phe Tyr Phe Asn Thr Asp Gly Ile Met Gln
2145              2150              2155              2160
```

```
Ile Gly Val Phe Lys Gly Pro Asn Gly Phe Glu Tyr Phe Ala Pro Ala
            2165                2170                2175

Asn Thr Asp Ala Asn Asn Ile Glu Gly Gln Ala Ile Leu Tyr Gln Asn
            2180                2185                2190

Glu Phe Leu Thr Leu Asn Gly Lys Lys Tyr Tyr Phe Gly Ser Asp Ser
            2195                2200                2205

Lys Ala Val Thr Gly Trp Arg Ile Ile Asn Asn Lys Lys Tyr Tyr Phe
            2210                2215                2220

Asn Pro Asn Asn Ala Ile Ala Ala Ile His Leu Cys Thr Ile Asn Asn
2225                2230                2235                2240

Asp Lys Tyr Tyr Phe Ser Tyr Asp Gly Ile Leu Gln Asn Gly Tyr Ile
            2245                2250                2255

Thr Ile Glu Arg Asn Asn Phe Tyr Phe Asp Ala Asn Asn Glu Ser Lys
            2260                2265                2270

Met Val Thr Gly Val Phe Lys Gly Pro Asn Gly Phe Glu Tyr Phe Ala
            2275                2280                2285

Pro Ala Asn Thr His Asn Asn Asn Ile Glu Gly Gln Ala Ile Val Tyr
            2290                2295                2300

Gln Asn Lys Phe Leu Thr Leu Asn Gly Lys Lys Tyr Tyr Phe Asp Asn
2305                2310                2315                2320

Asp Ser Lys Ala Val Thr Gly Trp Gln Thr Ile Asp Gly Lys Lys Tyr
            2325                2330                2335

Tyr Phe Asn Leu Asn Thr Ala Glu Ala Ala Thr Gly Trp Gln Thr Ile
            2340                2345                2350

Asp Gly Lys Lys Tyr Tyr Phe Asn Leu Asn Thr Ala Glu Ala Ala Thr
            2355                2360                2365

Gly Trp Gln Thr Ile Asp Gly Lys Lys Tyr Tyr Phe Asn Thr Asn Thr
            2370                2375                2380

Phe Ile Ala Ser Thr Gly Tyr Thr Ser Ile Asn Gly Lys His Phe Tyr
2385                2390                2395                2400

Phe Asn Thr Asp Gly Ile Met Gln Ile Gly Val Phe Lys Gly Pro Asn
            2405                2410                2415

Gly Phe Glu Tyr Phe Ala Pro Ala Asn Thr Asp Ala Asn Asn Ile Glu
            2420                2425                2430

Gly Gln Ala Ile Leu Tyr Gln Asn Lys Phe Leu Thr Leu Asn Gly Lys
            2435                2440                2445

Lys Tyr Tyr Phe Gly Ser Asp Ser Lys Ala Val Thr Gly Leu Arg Thr
            2450                2455                2460

Ile Asp Gly Lys Lys Tyr Tyr Phe Asn Thr Asn Thr Ala Val Ala Val
2465                2470                2475                2480

Thr Gly Trp Gln Thr Ile Asn Gly Lys Lys Tyr Tyr Phe Asn Thr Asn
            2485                2490                2495

Thr Ser Ile Ala Ser Thr Gly Tyr Thr Ile Ile Ser Gly Lys His Phe
            2500                2505                2510

Tyr Phe Asn Thr Asp Gly Ile Met Gln Ile Gly Val Phe Lys Gly Pro
            2515                2520                2525

Asp Gly Phe Glu Tyr Phe Ala Pro Ala Asn Thr Asp Ala Asn Asn Ile
            2530                2535                2540

Glu Gly Gln Ala Ile Arg Tyr Gln Asn Arg Phe Leu Tyr Leu His Asp
2545                2550                2555                2560

Asn Ile Tyr Tyr Phe Gly Asn Asn Ser Lys Ala Ala Thr Gly Trp Val
            2565                2570                2575

Thr Ile Asp Gly Asn Arg Tyr Tyr Phe Glu Pro Asn Thr Ala Met Gly
            2580                2585                2590
```

Ala Asn Gly Tyr Lys Thr Ile Asp Asn Lys Asn Phe Tyr Phe Arg Asn
        2595                2600                2605

Gly Leu Pro Gln Ile Gly Val Phe Lys Gly Ser Asn Gly Phe Glu Tyr
        2610                2615                2620

Phe Ala Pro Ala Asn Thr Asp Ala Asn Asn Ile Glu Gly Gln Ala Ile
2625                2630                2635                2640

Arg Tyr Gln Asn Arg Phe Leu His Leu Leu Gly Lys Ile Tyr Tyr Phe
            2645                2650                2655

Gly Asn Asn Ser Lys Ala Val Thr Gly Trp Gln Thr Ile Asn Gly Lys
        2660                2665                2670

Val Tyr Tyr Phe Met Pro Asp Thr Ala Met Ala Ala Ala Gly Gly Leu
            2675                2680                2685

Phe Glu Ile Asp Gly Val Ile Tyr Phe Phe Gly Val Asp Gly Val Lys
        2690                2695                2700

Ala Pro Gly Ile Tyr Gly
2705                2710

<210> SEQ ID NO 42
<211> LENGTH: 2367
<212> TYPE: PRT
<213> ORGANISM: Clostridium difficile

<400> SEQUENCE: 42

Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Thr Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Ile Glu Ile Leu Glu Leu Lys Asn Ser Asn Leu Thr Pro Val Glu Lys
                85                  90                  95

Asn Leu His Phe Ile Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Ile Ile Glu Ser Ala Ser Asn Asp Thr Leu Glu Ser Phe Arg Glu Asn
145                 150                 155                 160

Leu Asn Asp Pro Glu Phe Asn His Thr Ala Phe Phe Arg Lys Arg Met
                165                 170                 175

Gln Ile Ile Tyr Asp Lys Gln Gln Asn Phe Ile Asn Tyr Tyr Lys Ala
            180                 185                 190

Gln Lys Glu Glu Asn Pro Asp Leu Ile Ile Asp Asp Ile Val Lys Thr
        195                 200                 205

Tyr Leu Ser Asn Glu Tyr Ser Lys Asp Ile Asp Glu Leu Asn Ala Tyr
    210                 215                 220

Ile Glu Glu Ser Leu Asn Lys Val Thr Glu Asn Ser Gly Asn Asp Val
225                 230                 235                 240

Arg Asn Phe Glu Glu Phe Lys Thr Gly Glu Val Phe Asn Leu Tyr Glu
                245                 250                 255

```
Gln Glu Ser Val Glu Arg Trp Asn Leu Ala Gly Ala Ser Asp Ile Leu
                260                 265                 270

Arg Val Ala Ile Leu Lys Asn Ile Gly Gly Val Tyr Leu Asp Val Asp
            275                 280                 285

Met Leu Pro Gly Ile His Pro Asp Leu Phe Lys Asp Ile Asn Lys Pro
        290                 295                 300

Asp Ser Val Lys Thr Ala Val Asp Trp Glu Glu Met Gln Leu Glu Ala
305                 310                 315                 320

Ile Met Lys His Lys Glu Tyr Ile Pro Glu Tyr Thr Ser Lys His Phe
                325                 330                 335

Asp Thr Leu Asp Glu Glu Val Gln Ser Ser Phe Glu Ser Val Leu Ala
            340                 345                 350

Ser Lys Ser Asp Lys Ser Glu Ile Phe Leu Pro Leu Gly Asp Ile Glu
        355                 360                 365

Val Ser Pro Leu Glu Val Lys Ile Ala Phe Ala Lys Gly Ser Ile Ile
370                 375                 380

Asn Gln Ala Leu Ile Ser Ala Lys Asp Ser Tyr Cys Ser Asp Leu Leu
385                 390                 395                 400

Ile Lys Gln Ile Gln Asn Arg Tyr Lys Ile Leu Asn Asp Thr Leu Gly
                405                 410                 415

Pro Ile Ile Ser Gln Gly Asn Asp Phe Asn Thr Thr Met Asn Asn Phe
            420                 425                 430

Gly Glu Ser Leu Gly Ala Ile Ala Asn Glu Glu Asn Ile Ser Phe Ile
        435                 440                 445

Ala Lys Ile Gly Ser Tyr Leu Arg Val Gly Phe Tyr Pro Glu Ala Asn
450                 455                 460

Thr Thr Ile Thr Leu Ser Gly Pro Thr Ile Tyr Ala Gly Ala Tyr Lys
465                 470                 475                 480

Asp Leu Leu Thr Phe Lys Glu Met Ser Ile Asp Thr Ser Ile Leu Ser
                485                 490                 495

Ser Glu Leu Arg Asn Phe Glu Phe Pro Lys Val Asn Ile Ser Gln Ala
            500                 505                 510

Thr Glu Gln Glu Lys Asn Ser Leu Trp Gln Phe Asn Glu Glu Arg Ala
        515                 520                 525

Lys Ile Gln Phe Glu Glu Tyr Lys Lys Asn Tyr Phe Glu Gly Ala Leu
530                 535                 540

Gly Glu Asp Asp Asn Leu Asp Phe Ser Gln Asn Thr Val Thr Asp Lys
545                 550                 555                 560

Glu Tyr Leu Leu Glu Lys Ile Ser Ser Ser Thr Lys Ser Ser Glu Gly
                565                 570                 575

Gly Tyr Val His Tyr Ile Val Gln Leu Gln Gly Asp Lys Ile Ser Tyr
            580                 585                 590

Glu Ala Ala Cys Asn Leu Phe Ala Lys Asn Pro Tyr Asp Ser Ile Leu
        595                 600                 605

Phe Gln Arg Asn Ile Glu Asp Ser Glu Val Ala Tyr Tyr Tyr Asn Pro
610                 615                 620

Thr Asp Ser Glu Ile Gln Glu Ile Asp Lys Tyr Arg Ile Pro Asp Arg
625                 630                 635                 640

Ile Ser Asp Arg Pro Lys Ile Lys Leu Thr Phe Ile Gly His Gly Lys
                645                 650                 655

Ala Glu Phe Asn Thr Asp Ile Phe Ala Gly Leu Asp Val Asp Ser Leu
            660                 665                 670

Ser Ser Glu Ile Glu Thr Ala Ile Gly Leu Ala Lys Glu Asp Ile Ser
```

-continued

```
            675                 680                 685
Pro Lys Ser Ile Glu Ile Asn Leu Leu Gly Cys Asn Met Phe Ser Tyr
690                 695                 700

Ser Val Asn Val Glu Glu Thr Tyr Pro Gly Lys Leu Leu Arg Val
705                 710                 715                 720

Lys Asp Lys Val Ser Glu Leu Met Pro Ser Met Ser Gln Asp Ser Ile
                    725                 730                 735

Ile Val Ser Ala Asn Gln Tyr Glu Val Arg Ile Asn Ser Glu Gly Arg
                740                 745                 750

Arg Glu Leu Leu Asp His Ser Gly Glu Trp Ile Asn Lys Glu Glu Ser
            755                 760                 765

Ile Ile Lys Asp Ile Ser Ser Lys Glu Tyr Ile Ser Phe Asn Pro Lys
            770                 775                 780

Glu Asn Lys Ile Ile Val Lys Ser Lys Asn Leu Pro Glu Leu Ser Thr
785                 790                 795                 800

Leu Leu Gln Glu Ile Arg Asn Asn Ser Asn Ser Ser Asp Ile Glu Leu
                    805                 810                 815

Glu Glu Lys Val Met Leu Ala Glu Cys Glu Ile Asn Val Ile Ser Asn
                820                 825                 830

Ile Glu Thr Gln Val Val Glu Glu Arg Ile Glu Glu Ala Lys Ser Leu
            835                 840                 845

Thr Ser Asp Ser Ile Asn Tyr Ile Lys Asn Glu Phe Lys Leu Ile Glu
850                 855                 860

Ser Ile Ser Glu Ala Leu Cys Asp Leu Lys Gln Gln Asn Glu Leu Glu
865                 870                 875                 880

Asp Ser His Phe Ile Ser Phe Glu Asp Ile Ser Glu Thr Asp Glu Gly
                    885                 890                 895

Phe Ser Ile Arg Phe Ile Asn Lys Glu Thr Gly Glu Ser Ile Phe Val
                900                 905                 910

Glu Thr Glu Lys Thr Ile Phe Ser Glu Tyr Ala Asn His Ile Thr Glu
            915                 920                 925

Glu Ile Ser Lys Ile Lys Gly Thr Ile Phe Asp Thr Val Asn Gly Lys
            930                 935                 940

Leu Val Lys Lys Val Asn Leu Asp Thr Thr His Glu Val Asn Thr Leu
945                 950                 955                 960

Asn Ala Ala Phe Phe Ile Gln Ser Leu Ile Glu Tyr Asn Ser Ser Lys
                    965                 970                 975

Glu Ser Leu Ser Asn Leu Ser Val Ala Met Lys Val Gln Val Tyr Ala
                980                 985                 990

Gln Leu Phe Ser Thr Gly Leu Asn Thr Ile Thr Asp Ala Ala Lys Val
            995                 1000                1005

Val Glu Leu Val Ser Thr Ala Leu Asp Glu Thr Ile Asp Leu Leu Pro
   1010                1015                1020

Thr Leu Ser Glu Gly Leu Pro Ile Ile Ala Thr Ile Ile Asp Gly Val
   1025                1030                1035                1040

Ser Leu Gly Ala Ala Ile Lys Glu Leu Ser Glu Thr Ser Asp Pro Leu
                1045                1050                1055

Leu Arg Gln Glu Ile Glu Ala Lys Ile Gly Ile Met Ala Val Asn Leu
            1060                1065                1070

Thr Thr Ala Thr Thr Ala Ile Ile Thr Ser Ser Leu Gly Ile Ala Ser
            1075                1080                1085

Gly Phe Ser Ile Leu Leu Val Pro Leu Ala Gly Ile Ser Ala Gly Ile
   1090                1095                1100
```

-continued

```
Pro Ser Leu Val Asn Asn Glu Leu Val Leu Arg Asp Lys Ala Thr Lys
1105                1110                1115                1120

Val Val Asp Tyr Phe Lys His Val Ser Leu Val Glu Thr Glu Gly Val
        1125                1130                1135

Phe Thr Leu Leu Asp Asp Lys Val Met Met Gln Gln Asp Asp Leu Val
        1140                1145                1150

Ile Ser Glu Ile Asp Phe Asn Asn Ser Ile Val Leu Gly Lys Cys
        1155                1160                1165

Glu Ile Trp Arg Met Glu Gly Gly Ser Gly His Thr Val Thr Asp Asp
    1170                1175                1180

Ile Asp His Phe Ser Ala Pro Ser Ile Thr Tyr Arg Glu Pro His
1185                1190                1195                1200

Leu Ser Ile Tyr Asp Val Leu Glu Val Gln Lys Glu Glu Leu Asp Leu
        1205                1210                1215

Ser Lys Asp Leu Met Val Leu Pro Asn Ala Pro Asn Arg Val Phe Ala
        1220                1225                1230

Trp Glu Thr Gly Trp Thr Pro Gly Leu Arg Ser Leu Glu Asn Asp Gly
        1235                1240                1245

Thr Lys Leu Leu Asp Arg Ile Arg Asp Asn Tyr Glu Gly Glu Phe Tyr
        1250                1255                1260

Trp Arg Tyr Phe Ala Phe Ile Ala Asp Ala Leu Ile Thr Thr Leu Lys
1265                1270                1275                1280

Pro Arg Tyr Glu Asp Thr Asn Ile Arg Ile Asn Leu Asp Ser Asn Thr
        1285                1290                1295

Arg Ser Phe Ile Val Pro Ile Ile Thr Thr Glu Tyr Ile Arg Glu Lys
        1300                1305                1310

Leu Ser Tyr Ser Phe Tyr Gly Ser Gly Gly Thr Tyr Ala Leu Pro Leu
        1315                1320                1325

Ser Gln Tyr Asn Met Gly Ile Asn Ile Glu Leu Ser Glu Ser Asp Val
        1330                1335                1340

Trp Ile Ile Asp Val Asp Asn Val Val Arg Asp Val Thr Ile Glu Ser
1345                1350                1355                1360

Asp Lys Ile Lys Lys Gly Asp Leu Ile Glu Gly Ile Leu Ser Thr Leu
        1365                1370                1375

Ser Ile Glu Glu Asn Lys Ile Ile Leu Asn Ser His Glu Ile Asn Phe
        1380                1385                1390

Ser Gly Glu Val Asn Gly Ser Asn Gly Phe Val Ser Leu Thr Phe Ser
        1395                1400                1405

Ile Leu Glu Gly Ile Asn Ala Ile Ile Glu Val Asp Leu Leu Ser Lys
    1410                1415                1420

Ser Tyr Lys Leu Leu Ile Ser Gly Glu Leu Lys Ile Leu Met Leu Asn
1425                1430                1435                1440

Ser Asn His Ile Gln Gln Lys Ile Asp Tyr Ile Gly Phe Asn Ser Glu
        1445                1450                1455

Leu Gln Lys Asn Ile Pro Tyr Ser Phe Val Asp Ser Glu Gly Lys Glu
        1460                1465                1470

Asn Gly Phe Ile Asn Gly Ser Thr Lys Glu Gly Leu Phe Val Ser Glu
        1475                1480                1485

Leu Pro Asp Val Val Leu Ile Ser Lys Val Tyr Met Asp Asp Ser Lys
        1490                1495                1500

Pro Ser Phe Gly Tyr Tyr Ser Asn Asn Leu Lys Asp Val Lys Val Ile
1505                1510                1515                1520

Thr Lys Asp Asn Val Asn Ile Leu Thr Gly Tyr Tyr Leu Lys Asp Asp
        1525                1530                1535
```

```
Ile Lys Ile Ser Leu Ser Leu Thr Leu Gln Asp Glu Lys Thr Ile Lys
        1540                1545                1550

Leu Asn Ser Val His Leu Asp Glu Ser Gly Val Ala Glu Ile Leu Lys
        1555                1560                1565

Phe Met Asn Arg Lys Gly Ser Thr Asn Thr Ser Asp Ser Leu Met Ser
    1570                1575                1580

Phe Leu Glu Ser Met Asn Ile Lys Ser Ile Phe Val Asn Phe Leu Gln
1585                1590                1595                1600

Ser Asn Ile Lys Phe Ile Leu Asp Ala Asn Phe Ile Ile Ser Gly Thr
            1605                1610                1615

Thr Ser Ile Gly Gln Phe Glu Phe Ile Cys Asp Glu Asn Asn Asn Ile
        1620                1625                1630

Gln Pro Tyr Phe Ile Lys Phe Asn Thr Leu Glu Thr Asn Tyr Thr Leu
        1635                1640                1645

Tyr Val Gly Asn Arg Gln Asn Met Ile Val Glu Pro Asn Tyr Asp Leu
        1650                1655                1660

Asp Asp Ser Gly Asp Ile Ser Ser Thr Val Ile Asn Phe Ser Gln Lys
1665                1670                1675                1680

Tyr Leu Tyr Gly Ile Asp Ser Cys Val Asn Lys Val Val Ile Ser Pro
            1685                1690                1695

Asn Ile Tyr Thr Asp Glu Ile Asn Ile Thr Pro Val Tyr Glu Thr Asn
        1700                1705                1710

Asn Thr Tyr Pro Glu Val Ile Val Leu Asp Ala Asn Tyr Ile Asn Glu
        1715                1720                1725

Lys Ile Asn Val Asn Ile Asn Asp Leu Ser Ile Arg Tyr Val Trp Ser
        1730                1735                1740

Asn Asp Gly Asn Asp Phe Ile Leu Met Ser Thr Ser Glu Glu Asn Lys
1745                1750                1755                1760

Val Ser Gln Val Lys Ile Arg Phe Val Asn Val Phe Lys Asp Lys Thr
            1765                1770                1775

Leu Ala Asn Lys Leu Ser Phe Asn Phe Ser Asp Lys Gln Asp Val Pro
        1780                1785                1790

Val Ser Glu Ile Ile Leu Ser Phe Thr Pro Ser Tyr Tyr Glu Asp Gly
        1795                1800                1805

Leu Ile Gly Tyr Asp Leu Gly Leu Val Ser Leu Tyr Asn Glu Lys Phe
        1810                1815                1820

Tyr Ile Asn Asn Phe Gly Met Met Val Ser Gly Leu Ile Tyr Ile Asn
1825                1830                1835                1840

Asp Ser Leu Tyr Tyr Phe Lys Pro Pro Val Asn Asn Leu Ile Thr Gly
            1845                1850                1855

Phe Val Thr Val Gly Asp Asp Lys Tyr Tyr Phe Asn Pro Ile Asn Gly
        1860                1865                1870

Gly Ala Ala Ser Ile Gly Glu Thr Ile Ile Asp Asp Lys Asn Tyr Tyr
        1875                1880                1885

Phe Asn Gln Ser Gly Val Leu Gln Thr Gly Val Phe Ser Thr Glu Asp
        1890                1895                1900

Gly Phe Lys Tyr Phe Ala Pro Ala Asn Thr Leu Asp Glu Asn Leu Glu
1905                1910                1915                1920

Gly Glu Ala Ile Asp Phe Thr Gly Lys Leu Ile Ile Asp Glu Asn Ile
            1925                1930                1935

Tyr Tyr Phe Glu Asp Asn Tyr Arg Gly Ala Val Glu Trp Lys Glu Leu
        1940                1945                1950

Asp Gly Glu Met His Tyr Phe Ser Pro Glu Thr Gly Lys Ala Phe Lys
```

-continued

```
                1955                1960                1965
Gly Leu Asn Gln Ile Gly Asp Asp Lys Tyr Tyr Phe Asn Ser Asp Gly
    1970                1975                1980

Val Met Gln Lys Gly Phe Val Ser Ile Asn Asp Asn Lys His Tyr Phe
1985                1990                1995                2000

Asp Asp Ser Gly Val Met Lys Val Gly Tyr Thr Glu Ile Asp Gly Lys
        2005                2010                2015

His Phe Tyr Phe Ala Glu Asn Gly Glu Met Gln Ile Gly Val Phe Asn
            2020                2025                2030

Thr Glu Asp Gly Phe Lys Tyr Phe Ala His His Asn Glu Asp Leu Gly
                2035                2040                2045

Asn Glu Glu Gly Glu Glu Ile Ser Tyr Ser Gly Ile Leu Asn Phe Asn
    2050                2055                2060

Asn Lys Ile Tyr Tyr Phe Asp Asp Ser Phe Thr Ala Val Val Gly Trp
2065                2070                2075                2080

Lys Asp Leu Glu Asp Gly Ser Lys Tyr Tyr Phe Asp Glu Asp Thr Ala
        2085                2090                2095

Glu Ala Tyr Ile Gly Leu Ser Leu Ile Asn Asp Gly Gln Tyr Tyr Phe
            2100                2105                2110

Asn Asp Asp Gly Ile Met Gln Val Gly Phe Val Thr Ile Asn Asp Lys
                2115                2120                2125

Val Phe Tyr Phe Ser Asp Ser Gly Ile Ile Glu Ser Gly Val Gln Asn
    2130                2135                2140

Ile Asp Asp Asn Tyr Phe Tyr Ile Asp Asp Asn Gly Ile Val Gln Ile
2145                2150                2155                2160

Gly Val Phe Asp Thr Ser Asp Gly Tyr Lys Tyr Phe Ala Pro Ala Asn
        2165                2170                2175

Thr Val Asn Asp Asn Ile Tyr Gly Gln Ala Val Glu Tyr Ser Gly Leu
            2180                2185                2190

Val Arg Val Gly Glu Asp Val Tyr Tyr Phe Gly Glu Thr Tyr Thr Ile
                2195                2200                2205

Glu Thr Gly Trp Ile Tyr Asp Met Glu Asn Glu Ser Asp Lys Tyr Tyr
    2210                2215                2220

Phe Val Pro Glu Thr Lys Lys Ala Cys Lys Gly Ile Asn Leu Ile Asp
2225                2230                2235                2240

Asp Ile Lys Tyr Tyr Phe Asp Glu Lys Gly Ile Met Arg Thr Gly Leu
        2245                2250                2255

Ile Ser Phe Glu Asn Asn Asn Tyr Tyr Phe Asn Glu Asn Gly Glu Ile
            2260                2265                2270

Gln Phe Gly Tyr Ile Asn Ile Glu Asp Lys Met Phe Tyr Phe Gly Glu
                2275                2280                2285

Asp Gly Val Met Gln Ile Gly Val Phe Asn Thr Pro Asp Gly Phe Lys
    2290                2295                2300

Tyr Phe Ala His Gln Asn Thr Leu Asp Glu Asn Phe Glu Gly Glu Ser
2305                2310                2315                2320

Ile Asn Tyr Thr Gly Trp Leu Gly Leu Asp Glu Lys Arg Tyr Tyr Phe
        2325                2330                2335

Thr Asp Glu Tyr Ile Ala Ala Thr Gly Ser Val Ile Ile Asp Gly Glu
            2340                2345                2350

Glu Tyr Tyr Phe Asp Pro Asp Thr Ala Gln Leu Val Ile Ser Glu
                2355                2360                2365

<210> SEQ ID NO 43
<211> LENGTH: 129
```

```
<212> TYPE: PRT
<213> ORGANISM: Homo sapiens

<400> SEQUENCE: 43

Met Asp Met Met Val Pro Ala Gln Leu Leu Gly Leu Leu Leu Trp
1               5                   10                  15

Phe Pro Gly Ser Arg Cys Asp Ile Gln Met Thr Gln Ser Pro Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln His Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Trp Thr Phe Gly Gln Gly Thr Lys Val Glu Ile
        115                 120                 125

Lys

<210> SEQ ID NO 44
<211> LENGTH: 129
<212> TYPE: PRT
<213> ORGANISM: Homo sapiens

<400> SEQUENCE: 44

Met Asp Met Arg Val Leu Ala Gln Leu Leu Gly Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Trp Thr Phe Gly Gln Gly Thr Lys Val Glu Ile
        115                 120                 125

Lys

<210> SEQ ID NO 45
<211> LENGTH: 129
<212> TYPE: PRT
<213> ORGANISM: Homo sapiens

<400> SEQUENCE: 45

Met Asp Met Arg Val Pro Ala Gln Leu Leu Gly Leu Leu Leu Leu Trp
1               5                   10                  15

Leu Pro Gly Ala Arg Cys Val Ile Trp Met Thr Gln Ser Pro Ser Leu
            20                  25                  30

Leu Ser Ala Ser Thr Gly Asp Arg Val Thr Ile Ser Cys Arg Met Ser
```

```
            35                  40                  45
Gln Gly Ile Ser Ser Tyr Leu Ala Trp Tyr Gln Gln Lys Pro Gly Lys
 50                  55                  60

Ala Pro Glu Leu Leu Ile Tyr Ala Ala Ser Thr Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Tyr Asn Ser Tyr Pro Trp Thr Phe Gly Gln Gly Thr Lys Val Glu Ile
            115                 120                 125

Lys

<210> SEQ ID NO 46
<211> LENGTH: 129
<212> TYPE: PRT
<213> ORGANISM: Homo sapiens

<400> SEQUENCE: 46

Met Asp Met Met Val Pro Ala Gln Leu Leu Gly Leu Leu Leu Leu Trp
 1               5                  10                  15

Phe Pro Gly Ser Arg Cys Asp Ile Gln Met Thr Gln Ser Pro Ser Ser
                 20                  25                  30

Val Ser Ala Ser Val Gly Asp Arg Val Thr Ile Thr Cys Arg Ala Ser
             35                  40                  45

Gln Gly Ile Ser Ser Trp Leu Ala Trp Tyr Gln His Lys Pro Gly Lys
 50                  55                  60

Ala Pro Lys Leu Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Tyr Asn Ser Tyr Pro Trp Thr Phe Gly Gln Gly Thr Lys Val Glu Ile
            115                 120                 125

Lys

<210> SEQ ID NO 47
<211> LENGTH: 129
<212> TYPE: PRT
<213> ORGANISM: Homo sapiens

<400> SEQUENCE: 47

Met Asp Met Arg Val Pro Ala Gln Leu Leu Gly Leu Leu Leu Leu Cys
 1               5                  10                  15

Phe Pro Gly Ala Arg Cys Asp Ile Gln Met Thr Gln Ser Pro Ser Ser
                 20                  25                  30

Val Ser Ala Ser Val Gly Asp Arg Val Thr Ile Thr Cys Arg Ala Ser
             35                  40                  45

Gln Gly Ile Ser Ser Trp Leu Ala Trp Tyr Gln Gln Lys Pro Glu Lys
 50                  55                  60

Ala Pro Lys Ser Leu Ile Tyr Ala Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
```

```
                        100                 105                 110
Tyr Asn Ser Tyr Pro Trp Thr Phe Gly Gln Gly Thr Lys Val Glu Ile
                115                 120                 125
Lys

<210> SEQ ID NO 48
<211> LENGTH: 129
<212> TYPE: PRT
<213> ORGANISM: Homo sapiens

<400> SEQUENCE: 48

Met Asp Met Arg Val Leu Ala Gln Leu Leu Gly Leu Leu Leu Leu Cys
 1               5                  10                  15

Phe Pro Gly Ala Arg Cys Asp Ile Gln Met Thr Gln Ser Leu Ser Ser
                20                  25                  30

Leu Ser Ala Ser Val Gly Asp Arg Val Thr Ile Thr Cys Arg Ala Ser
            35                  40                  45

Gln Gly Ile Ser Ser Trp Leu Ala Trp Tyr Gln Gln Lys Pro Glu Lys
        50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Ala Asn Ser Phe Pro Trp Thr Phe Gly Gln Gly Thr Lys Val Glu Ile
                115                 120                 125

Lys

<210> SEQ ID NO 49
<211> LENGTH: 141
<212> TYPE: PRT
<213> ORGANISM: Homo sapiens

<400> SEQUENCE: 49

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Ser Phe
            35                  40                  45

Ser Asn Tyr Gly Met His Trp Val Arg Gln Ala Pro Gly Lys Gly Leu
        50                  55                  60

Glu Trp Val Ala Leu Ile Trp Tyr Asp Gly Ser Asn Glu Asp Tyr Thr
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Arg Trp Gly Met Val Arg Gly Val Ile Asp Val Phe
                115                 120                 125

Asp Ile Trp Gly Gln Gly Thr Val Val Thr Val Ser Ser
            130                 135                 140

<210> SEQ ID NO 50
<211> LENGTH: 128
<212> TYPE: PRT
```

<213> ORGANISM: Homo sapiens

<400> SEQUENCE: 50

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Ser Gln Phe Thr Phe Gly Pro Gly Thr Lys Val Asp Ile Lys
        115                 120                 125

<210> SEQ ID NO 51
<211> LENGTH: 133
<212> TYPE: PRT
<213> ORGANISM: Homo sapiens

<400> SEQUENCE: 51

Met Glu Phe Gly Leu Ser Trp Val Phe Leu Val Ala Leu Leu Arg Gly
1               5                   10                  15

Val Gln Cys Gln Met Gln Leu Val Glu Ser Gly Gly Gly Val Val Gln
            20                  25                  30

Pro Gly Arg Ser Leu Arg Leu Ser Cys Glu Ala Ser Gly Phe Ser Phe
        35                  40                  45

Asn Ser Tyr Gly Met His Trp Val Arg Gln Ala Pro Gly Lys Gly Leu
    50                  55                  60

Glu Trp Val Ser Val Ile Trp Ala Ser Gly Asn Lys Lys Tyr Tyr Ile
65                  70                  75                  80

Glu Ser Val Glu Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Asn Phe Asp Tyr Trp Gly Gln Gly Thr Leu
        115                 120                 125

Val Thr Val Ser Ser
    130

<210> SEQ ID NO 52
<211> LENGTH: 129
<212> TYPE: PRT
<213> ORGANISM: Homo sapiens

<400> SEQUENCE: 52

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

```
Gln Gly Ile Ser Ser Trp Leu Ala Trp Tyr Gln Gln Lys Pro Glu Lys
         50                  55                  60
Ala Pro Lys Ser Leu Ile Tyr Ala Ala Ser Ser Leu Gln Ser Gly Val
 65                  70                  75                  80
Pro Ser Arg Phe Ser Gly Ser Gly Ser Gly Thr Asp Phe Thr Leu Thr
                 85                  90                  95
Ile Ser Ser Leu Gln Pro Glu Asp Phe Ala Thr Tyr Tyr Cys Gln Gln
            100                 105                 110
Tyr Lys Ser Tyr Pro Val Thr Phe Gly Gly Gly Thr Lys Val Glu Ile
        115                 120                 125
Lys

<210> SEQ ID NO 53
<211> LENGTH: 135
<212> TYPE: PRT
<213> ORGANISM: Homo sapiens

<400> SEQUENCE: 53

Met Glu Phe Gly Leu Ser Trp Val Phe Leu Val Ala Leu Leu Arg Gly
 1               5                  10                  15
Val Gln Cys Gln Val Gln Leu Val Glu Ser Gly Gly Gly Val Val Gln
             20                  25                  30
Pro Gly Arg Ser Leu Arg Leu Ser Cys Ala Ala Ser Gly Phe Thr Phe
         35                  40                  45
Asn Lys Tyr Gly Met His Trp Val Arg Gln Ala Pro Gly Lys Gly Leu
     50                  55                  60
Glu Trp Val Ala Val Ile Trp Tyr Asp Gly Thr Asn Lys Tyr Tyr Ala
 65                  70                  75                  80
Asp Ser Met Lys Gly Arg Phe Thr Ile Ser Arg Asp Asn Ser Lys Asn
                 85                  90                  95
Met Leu Tyr Leu Gln Met Asn Ser Leu Arg Ala Glu Asp Thr Ala Val
            100                 105                 110
Tyr Tyr Cys Ala Arg Asp Pro Pro Thr Ala Asn Tyr Trp Gly Gln Gly
        115                 120                 125
Thr Leu Val Thr Val Ser Ser
    130                 135

<210> SEQ ID NO 54
<211> LENGTH: 119
<212> TYPE: PRT
<213> ORGANISM: Homo sapiens

<400> SEQUENCE: 54

Glu Val Gln Leu Val Gln Ser Gly Ala Glu Val Lys Lys Ser Gly Glu
 1               5                  10                  15
Ser Leu Lys Ile Ser Cys Lys Gly Ser Gly Tyr Ser Phe Thr Ser Tyr
             20                  25                  30
Trp Ile Gly Trp Val Arg Gln Met Pro Gly Lys Gly Leu Glu Trp Met
         35                  40                  45
Gly Ile Phe Tyr Pro Gly Asp Ser Ser Thr Arg Tyr Ser Pro Ser Phe
     50                  55                  60
Gln Gly Gln Val Thr Ile Ser Ala Asp Lys Ser Val Asn Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Arg Arg Asn Trp Gly Asn Ala Phe Asp Ile Trp Gly Gln Gly
            100                 105                 110
```

Thr Met Val Thr Val Ser Ser
        115

<210> SEQ ID NO 55
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 55

| | | | | | | | | | | | | | | | | |
|---|---|---|---|---|---|---|---|---|---|---|---|---|---|---|---|---|
| gag | gtg | cag | ctg | gtg | cag | tct | gga | gca | gag | gtg | aaa | aag | tcc | ggg | gag | 48 |
| Glu | Val | Gln | Leu | Val | Gln | Ser | Gly | Ala | Glu | Val | Lys | Lys | Ser | Gly | Glu | |
| 1 | | | | 5 | | | | | 10 | | | | | 15 | | |
| tct | ctg | aag | atc | tcc | tgt | aag | ggt | tct | gga | tac | agc | ttt | acc | agc | tac | 96 |
| Ser | Leu | Lys | Ile | Ser | Cys | Lys | Gly | Ser | Gly | Tyr | Ser | Phe | Thr | Ser | Tyr | |
| | | | 20 | | | | | 25 | | | | | 30 | | | |
| tgg | atc | ggc | tgg | gtg | cgc | cag | atg | ccc | ggg | aag | ggc | ctg | gag | tgg | atg | 144 |
| Trp | Ile | Gly | Trp | Val | Arg | Gln | Met | Pro | Gly | Lys | Gly | Leu | Glu | Trp | Met | |
| | | 35 | | | | | 40 | | | | | 45 | | | | |
| ggg | atc | ttc | tat | cct | ggt | gac | tct | agt | acc | aga | tac | agc | ccg | tcc | ttc | 192 |
| Gly | Ile | Phe | Tyr | Pro | Gly | Asp | Ser | Ser | Thr | Arg | Tyr | Ser | Pro | Ser | Phe | |
| | 50 | | | | | 55 | | | | | 60 | | | | | |
| caa | ggc | cag | gtc | acc | atc | tca | gcc | gac | aag | tcc | gtc | aac | acc | gcc | tac | 240 |
| Gln | Gly | Gln | Val | Thr | Ile | Ser | Ala | Asp | Lys | Ser | Val | Asn | Thr | Ala | Tyr | |
| 65 | | | | | 70 | | | | | 75 | | | | | 80 | |
| ctg | cag | tgg | agc | agc | ctg | aag | gcc | tcg | gac | acc | gcc | atg | tat | tac | tgt | 288 |
| Leu | Gln | Trp | Ser | Ser | Leu | Lys | Ala | Ser | Asp | Thr | Ala | Met | Tyr | Tyr | Cys | |
| | | | | 85 | | | | | 90 | | | | | 95 | | |
| gcg | aga | cgt | cga | aac | tgg | gga | aat | gct | ttt | gat | atc | tgg | ggc | caa | ggg | 336 |
| Ala | Arg | Arg | Arg | Asn | Trp | Gly | Asn | Ala | Phe | Asp | Ile | Trp | Gly | Gln | Gly | |
| | | | 100 | | | | | 105 | | | | | 110 | | | |
| aca | atg | gtc | acc | gtc | tct | tca | | | | | | | | | | 357 |
| Thr | Met | Val | Thr | Val | Ser | Ser | | | | | | | | | | |
| | | | 115 | | | | | | | | | | | | | |

<210> SEQ ID NO 56
<211> LENGTH: 138
<212> TYPE: PRT
<213> ORGANISM: Homo sapiens

<400> SEQUENCE: 56

Met Gly Ser Thr Ala Ile Leu Ala Leu Leu Ala Val Leu Gln Gly
1               5                   10                  15

Val Cys Ala Glu Val Gln Leu Val Gln Ser Gly Ala Glu Val Lys Lys
            20                  25                  30

Ser Gly Glu Ser Leu Lys Ile Ser Cys Lys Gly Ser Gly Tyr Ser Phe
        35                  40                  45

Thr Ser Tyr Trp Ile Gly Trp Val Arg Gln Met Pro Gly Lys Gly Leu
    50                  55                  60

Glu Trp Met Gly Ile Phe Tyr Pro Gly Asp Ser Ser Thr Arg Tyr Ser
65                  70                  75                  80

Pro Ser Phe Gln Gly Gln Val Thr Ile Ser Ala Asp Lys Ser Val Asn
                85                  90                  95

Thr Ala Tyr Leu Gln Trp Ser Ser Leu Lys Ala Ser Asp Thr Ala Met
            100                 105                 110

Tyr Tyr Cys Ala Arg Arg Arg Asn Trp Gly Asn Ala Phe Asp Ile Trp
        115                 120                 125

Gly Gln Gly Thr Met Val Thr Val Ser Ser

<210> SEQ ID NO 57
<211> LENGTH: 414
<212> TYPE: DNA
<213> ORGANISM: Homo sapiens

<400> SEQUENCE: 57

```
atggggtcaa ccgccatcct cgccctcctc ctggctgttc tccaaggagt ctgtgccgag      60
gtgcagctgg tgcagtctgg agcagaggtg aaaaagtccg gggagtctct gaagatctcc     120
tgtaagggtt ctggatacag ctttaccagc tactggatcg gctgggtgcg ccagatgccc     180
gggaagggcc tggagtggat ggggatcttc tatcctggtg actctagtac cagatacagc     240
ccgtccttcc aaggccaggt caccatctca gccgacaagt ccgtcaacac cgcctacctg     300
cagtggagca gcctgaaggc ctcggacacc gccatgtatt actgtgcgag acgtcgaaac     360
tggggaaatg cttttgatat ctggggccaa gggacaatgg tcaccgtctc ttca           414
```

<210> SEQ ID NO 58
<211> LENGTH: 108
<212> TYPE: PRT
<213> ORGANISM: Homo sapiens

<400> SEQUENCE: 58

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Thr
                 85                  90                  95

Trp Thr Phe Gly Gln Gly Thr Lys Val Glu Ile Lys
            100                 105
```

<210> SEQ ID NO 59
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 59

```
gaa att gtg ttg acg cag tct cca ggc acc ctg tct ttg tct cca ggg       48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc       96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc ctc      144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt      192
Ile Tyr Gly Ala Ser Ser Arg Ala Thr Gly Ile Pro Asp Arg Phe Ser
     50                  55                  60
```

```
ggc agt ggg tct ggg aca gac ttc act ctc acc atc agc aga ctg gag      240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca acg      288
Pro Glu Asp Phe Ala Val Tyr Tyr Cys Gln Gln Tyr Gly Ser Ser Thr
                 85                  90                  95 tgg acg ttc ggc caa ggg acc aag gtg gaa atc aaa                      324
Trp Thr Phe Gly Gln Gly Thr Lys Val Glu Ile Lys
            100                 105

<210> SEQ ID NO 60
<211> LENGTH: 128
<212> TYPE: PRT
<213> ORGANISM: Homo sapiens

<400> SEQUENCE: 60

Met Glu Thr Pro Ala Gln Leu Leu Phe Leu Leu Leu Leu Trp Leu Pro
  1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Val Ser Ser Ser Tyr Leu Ala Trp Tyr Gln Gln Lys Pro Gly Gln Ala
     50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
            100                 105                 110

Gly Ser Ser Thr Trp Thr Phe Gly Gln Gly Thr Lys Val Glu Ile Lys
        115                 120                 125

<210> SEQ ID NO 61
<211> LENGTH: 384
<212> TYPE: DNA
<213> ORGANISM: Homo sapiens

<400> SEQUENCE: 61
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact tagcctggta ccagcagaaa     180
cctggccagg ctcccaggct cctcatctat ggtgcatcca gcagggccac tggcatccca     240
gacaggttca gtggcagtgg gtctgggaca gacttcactc tcaccatcag cagactggag     300
cctgaagatt ttgcagtgta ttactgtcag cagtatggta gctcaacgtg gacgttcggc     360
caagggacca aggtggaaat caaa                                            384

<210> SEQ ID NO 62
<211> LENGTH: 5
<212> TYPE: PRT
<213> ORGANISM: Homo sapiens

<400> SEQUENCE: 62

Ser Tyr Trp Ile Gly
  1               5

<210> SEQ ID NO 63
<211> LENGTH: 15
```

```
<212> TYPE: DNA
<213> ORGANISM: Homo sapiens
<220> FEATURE:
<221> NAME/KEY: CDS
<222> LOCATION: (1)..(15)

<400> SEQUENCE: 63 agc tac tgg atc ggc                                                       15
Ser Tyr Trp Ile Gly
 1               5

<210> SEQ ID NO 64
<211> LENGTH: 17
<212> TYPE: PRT
<213> ORGANISM: Homo sapiens

<400> SEQUENCE: 64

Ile Phe Tyr Pro Gly Asp Ser Ser Thr Arg Tyr Ser Pro Ser Phe Gln
 1               5                  10                  15
Gly

<210> SEQ ID NO 65
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 65 atc ttc tat cct ggt gac tct agt acc aga tac agc ccg tcc ttc caa         48
Ile Phe Tyr Pro Gly Asp Ser Ser Thr Arg Tyr Ser Pro Ser Phe Gln
 1               5                  10                  15 ggc                                                                      51
Gly

<210> SEQ ID NO 66
<211> LENGTH: 10
<212> TYPE: PRT
<213> ORGANISM: Homo sapiens

<400> SEQUENCE: 66

Arg Arg Asn Trp Gly Asn Ala Phe Asp Ile
 1               5                  10

<210> SEQ ID NO 67
<211> LENGTH: 30
<212> TYPE: DNA
<213> ORGANISM: Homo sapiens
<220> FEATURE:
<221> NAME/KEY: CDS
<222> LOCATION: (1)..(30)

<400> SEQUENCE: 67 cgt cga aac tgg gga aat gct ttt gat atc                                  30
Arg Arg Asn Trp Gly Asn Ala Phe Asp Ile
 1               5                  10

<210> SEQ ID NO 68
<211> LENGTH: 12
<212> TYPE: PRT
<213> ORGANISM: Homo sapiens

<400> SEQUENCE: 68

Arg Ala Ser Gln Ser Val Ser Ser Tyr Leu Ala
 1               5                  10
```

<210> SEQ ID NO 69
<211> LENGTH: 36
<212> TYPE: DNA
<213> ORGANISM: Homo sapiens
<220> FEATURE:
<221> NAME/KEY: CDS
<222> LOCATION: (1)..(36)

<400> SEQUENCE: 69 agg gcc agt cag agt gtt agc agc agc tac tta gcc                36
Arg Ala Ser Gln Ser Val Ser Ser Ser Tyr Leu Ala
 1               5                  10

<210> SEQ ID NO 70
<211> LENGTH: 7
<212> TYPE: PRT
<213> ORGANISM: Homo sapiens

<400> SEQUENCE: 70

Gly Ala Ser Ser Arg Ala Thr
 1               5

<210> SEQ ID NO 71
<211> LENGTH: 21
<212> TYPE: DNA
<213> ORGANISM: Homo sapiens
<220> FEATURE:
<221> NAME/KEY: CDS
<222> LOCATION: (1)..(21)

<400> SEQUENCE: 71 ggt gca tcc agc agg gcc act                                    21
Gly Ala Ser Ser Arg Ala Thr
 1               5

<210> SEQ ID NO 72
<211> LENGTH: 9
<212> TYPE: PRT
<213> ORGANISM: Homo sapiens

<400> SEQUENCE: 72

Gln Gln Tyr Gly Ser Ser Thr Trp Thr
 1               5

<210> SEQ ID NO 73
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 73 cag cag tat ggt agc tca acg tgg acg                            27
Gln Gln Tyr Gly Ser Ser Thr Trp Thr
 1               5

<210> SEQ ID NO 74
<211> LENGTH: 15
<212> TYPE: PRT
<213> ORGANISM: Homo sapiens

<400> SEQUENCE: 74

Ala Phe Asp Ile Trp Gly Gln Gly Thr Met Val Thr Val Ser Ser
 1               5                  10                  15

<210> SEQ ID NO 75

```
<211> LENGTH: 5
<212> TYPE: PRT
<213> ORGANISM: Homo sapiens

<400> SEQUENCE: 75

Ser Tyr Trp Ile Gly
  1               5

<210> SEQ ID NO 76
<211> LENGTH: 17
<212> TYPE: PRT
<213> ORGANISM: Homo sapiens

<400> SEQUENCE: 76

Ile Ile Tyr Pro Gly Asp Ser Asp Thr Arg Tyr Ser Pro Ser Phe Gln
  1               5                  10                  15

Gly

<210> SEQ ID NO 77
<211> LENGTH: 10
<212> TYPE: PRT
<213> ORGANISM: Homo sapiens

<400> SEQUENCE: 77

Ala Arg Arg Arg Asn Trp Gly Asn Ala Phe
  1               5                  10

<210> SEQ ID NO 78
<211> LENGTH: 11
<212> TYPE: PRT
<213> ORGANISM: Homo sapiens

<400> SEQUENCE: 78

Ala Ser Gln Ser Val Ser Ser Ser Tyr Leu Ala
  1               5                  10

<210> SEQ ID NO 79
<211> LENGTH: 12
<212> TYPE: PRT
<213> ORGANISM: Homo sapiens

<400> SEQUENCE: 79

Trp Thr Phe Gly Gln Gly Thr Lys Val Glu Ile Lys
  1               5                  10

<210> SEQ ID NO 80
<211> LENGTH: 9
<212> TYPE: PRT
<213> ORGANISM: Homo sapiens

<400> SEQUENCE: 80

Gln Gln Tyr Gly Ser Ser Pro Trp Thr
  1               5

<210> SEQ ID NO 81
<211> LENGTH: 98
<212> TYPE: PRT
<213> ORGANISM: Homo sapiens

<400> SEQUENCE: 81

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30
```

```
                               -continued

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg

<210> SEQ ID NO 82
<211> LENGTH: 96
<212> TYPE: PRT
<213> ORGANISM: Homo sapiens

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```